US010039970B2

(12) United States Patent
Lee et al.

(10) Patent No.: US 10,039,970 B2
(45) Date of Patent: Aug. 7, 2018

(54) LOCATION-AWARE FITNESS MONITORING METHODS, SYSTEMS, AND PROGRAM PRODUCTS, AND APPLICATIONS THEREOF

(75) Inventors: Alan Russell Lee, Montara, CA (US); Andrew Leonard Axelrod, West Linn, OR (US); Stephen John Black, Portland, OR (US); Mark Arthur Oleson, Portland, OR (US); Jon H. Werner, Austin, TX (US); Christian Dibenedetto, North Plains, OR (US)

(73) Assignee: adidas AG, Herzogenaurach (DE)

( * ) Notice: Subject to any disclaimer, the term of this patent is extended or adjusted under 35 U.S.C. 154(b) by 379 days.

(21) Appl. No.: 12/836,416

(22) Filed: Jul. 14, 2010

(65) Prior Publication Data

US 2012/0015778 A1 Jan. 19, 2012

(51) Int. Cl.
  *A63B 71/06* (2006.01)
  *G16H 20/30* (2018.01)
  (Continued)

(52) U.S. Cl.
  CPC ...... *A63B 71/0686* (2013.01); *A63B 71/0622* (2013.01); *G06F 19/3481* (2013.01);
  (Continued)

(58) Field of Classification Search
  CPC ............ A63B 71/0686; A63B 71/0622; A63B 2220/30; A63B 2220/17; A63B 2220/13;
  (Continued)

(56) References Cited

U.S. PATENT DOCUMENTS 4,867,442 A 9/1989 Matthews
5,043,736 A 8/1991 Darnell et al.
(Continued)

FOREIGN PATENT DOCUMENTS

CN 101031101 A 9/2007
DE 3320502 A1 12/1983
(Continued)

OTHER PUBLICATIONS

GPSII, Garmin Owner's Manual & Reference, 108 pages, Aug. 1996, Garmin Corp., Kansas, USA.
(Continued)

*Primary Examiner* — Sundhara Ganesan
(74) *Attorney, Agent, or Firm* — Sterne, Kessler, Goldstein & Fox P.L.L.C.

(57) ABSTRACT

Location-aware fitness monitoring program products, systems, and methods, and applications thereof, are disclosed. In an embodiment, a method for providing feedback to an athlete via a portable fitness monitoring device includes the steps of calculating a plurality of speed points from a plurality of time-stamped position points, calculating an output speed based on at least some of the plurality of speed points, determining that the output speed is outside of a predetermined speed range, receiving acceleration data from an accelerometer, determining that a recent speed change has occurred based on the acceleration data, providing feedback to the athlete via the portable fitness monitoring device, wherein the feedback is provided in response to the determination that the output speed is outside of the predetermined speed range, and in response to the determination that the recent speed change has occurred.

26 Claims, 55 Drawing Sheets

(51) Int. Cl.
*G06F 19/00* (2018.01)
*A63B 24/00* (2006.01)

(52) U.S. Cl.
CPC ...... *G16H 20/30* (2018.01); *A63B 2024/0068* (2013.01); *A63B 2071/0625* (2013.01); *A63B 2071/0661* (2013.01); *A63B 2071/0694* (2013.01); *A63B 2220/12* (2013.01); *A63B 2220/13* (2013.01); *A63B 2220/17* (2013.01); *A63B 2220/30* (2013.01); *A63B 2220/40* (2013.01); *A63B 2220/62* (2013.01)

(58) Field of Classification Search
CPC ........ A63B 2220/62; A63B 2071/0694; A63B 2071/0661; A63B 2071/0625; A63B 2024/0068; A63B 2220/40; A63B 2220/12; G16H 20/30; G06F 19/3481
USPC .......................................................... 482/8
See application file for complete search history.

(56) References Cited

U.S. PATENT DOCUMENTS

| | | |
|---|---|---|
| 5,291,301 A | 3/1994 | Lee |
| 5,334,974 A | 8/1994 | Simms et al. |
| 5,335,188 A | 8/1994 | Brisson |
| 5,400,254 A | 3/1995 | Fujita |
| 5,470,233 A | 11/1995 | Fruchterman et al. |
| 5,598,849 A | 2/1997 | Browne |
| 5,627,548 A | 5/1997 | Woo et al. |
| 5,702,323 A | 12/1997 | Poulton |
| 5,724,265 A | 3/1998 | Hutchings |
| 5,742,509 A | 4/1998 | Goldberg et al. |
| 5,751,245 A | 5/1998 | Janky et al. |
| 5,758,313 A | 5/1998 | Shah et al. |
| 5,767,795 A | 6/1998 | Schaphorst |
| 5,802,492 A | 9/1998 | DeLorme et al. |
| 5,825,327 A | 10/1998 | Krasner |
| 5,857,066 A | 1/1999 | Wyche et al. |
| 5,908,464 A | 6/1999 | Kishigami et al. |
| 5,910,799 A | 6/1999 | Carpenter et al. |
| 5,919,239 A | 7/1999 | Fraker et al. |
| 5,938,721 A | 8/1999 | Dussell et al. |
| 5,948,040 A | 9/1999 | DeLorme et al. |
| 5,976,083 A | 11/1999 | Richardson et al. |
| 6,002,982 A | 12/1999 | Fry |
| 6,009,138 A | 12/1999 | Slusky |
| 6,011,494 A | 1/2000 | Watanabe et al. |
| 6,013,007 A * | 1/2000 | Root et al. ........................ 482/8 |
| 6,032,108 A | 2/2000 | Seiple et al. |
| 6,135,951 A | 10/2000 | Richardson et al. |
| 6,198,431 B1 | 3/2001 | Gibson |
| 6,212,469 B1 | 4/2001 | Knepper |
| 6,246,362 B1 | 6/2001 | Tsubata et al. |
| 6,251,048 B1 | 6/2001 | Kaufman |
| 6,463,385 B1 | 10/2002 | Fry |
| 6,513,532 B2 | 2/2003 | Mault et al. |
| 6,582,342 B2 | 6/2003 | Kaufman |
| 6,585,622 B1 | 7/2003 | Shum et al. |
| 6,601,016 B1 | 7/2003 | Brown et al. |
| 6,605,038 B1 | 8/2003 | Teller et al. |
| 6,611,789 B1 | 8/2003 | Darley |
| 6,716,139 B1 | 4/2004 | Hosseinzadeh-Dolkhani et al. |
| 6,736,759 B1 | 5/2004 | Stubbs et al. |
| 6,741,927 B2 | 5/2004 | Jones |
| 6,746,370 B1 | 6/2004 | Fleming et al. |
| 6,746,371 B1 | 6/2004 | Brown et al. |
| 6,790,178 B1 | 9/2004 | Mault et al. |
| 6,798,378 B1 | 9/2004 | Walters |
| 6,823,036 B1 | 11/2004 | Chen |
| 6,837,827 B1 | 1/2005 | Lee et al. |
| 6,845,321 B1 | 1/2005 | Kerns |
| 6,853,955 B1 | 2/2005 | Burrell et al. |
| 6,872,077 B2 | 3/2005 | Yeager |
| 6,879,285 B2 | 4/2005 | Nobukiyo |
| 6,882,955 B1 | 4/2005 | Ohlenbusch et al. |
| 6,918,858 B2 | 7/2005 | Watterson et al. |
| 6,921,351 B1 | 7/2005 | Hickman et al. |
| 7,062,225 B2 | 6/2006 | White |
| 7,070,539 B2 | 7/2006 | Brown et al. |
| 7,172,530 B1 | 2/2007 | Hercules |
| 7,216,034 B2 | 5/2007 | Vitikainen et al. |
| 7,217,224 B2 | 5/2007 | Thomas |
| 7,220,220 B2 | 5/2007 | Stubbs et al. |
| 7,251,454 B2 | 7/2007 | White |
| 7,254,516 B2 | 8/2007 | Case, Jr. et al. |
| 7,257,517 B2 | 8/2007 | Shitan |
| 7,292,867 B2 | 11/2007 | Werner et al. |
| 7,428,471 B2 | 9/2008 | Darley et al. |
| 7,428,472 B2 | 9/2008 | Darley et al. |
| 7,466,992 B1 | 12/2008 | Fujisaki |
| 7,480,512 B2 | 1/2009 | Graham et al. |
| 7,518,054 B2 | 4/2009 | McKinney et al. |
| 7,519,327 B2 | 4/2009 | White |
| 7,603,255 B2 | 10/2009 | Case, Jr. et al. |
| 7,643,895 B2 | 1/2010 | Gupta et al. |
| 7,648,463 B1 | 1/2010 | Elhag et al. |
| 7,670,263 B2 | 3/2010 | Ellis et al. |
| 7,706,815 B2 | 4/2010 | Graham et al. |
| 7,717,827 B2 | 5/2010 | Kurunmäki et al. |
| 7,766,794 B2 | 8/2010 | Oliver et al. |
| 7,771,320 B2 | 8/2010 | Riley et al. |
| 7,805,149 B2 | 9/2010 | Werner et al. |
| 7,805,150 B2 | 9/2010 | Graham et al. |
| 7,921,163 B1 | 4/2011 | Odell et al. |
| 7,951,046 B1 | 5/2011 | Barber, Jr. |
| 7,985,164 B2 | 7/2011 | Ashby |
| 8,001,472 B2 | 8/2011 | Gilley et al. |
| 8,112,226 B2 * | 2/2012 | Soehren ........................ 701/487 |
| 2001/0027375 A1 | 10/2001 | Machida et al. |
| 2002/0049535 A1 | 4/2002 | Rigo et al. |
| 2002/0094776 A1 | 7/2002 | Pulver |
| 2002/0102988 A1 | 8/2002 | Myllymaki |
| 2002/0107433 A1 | 8/2002 | Mault |
| 2002/0166437 A1 * | 11/2002 | Nishitani ............. G10H 1/0008 84/600 |
| 2003/0091964 A1 | 5/2003 | Yeager |
| 2003/0100315 A1 | 5/2003 | Rankin |
| 2003/0171189 A1 | 9/2003 | Kaufman |
| 2003/0191578 A1 | 10/2003 | Paulauskas et al. |
| 2003/0208409 A1 | 11/2003 | Mault |
| 2003/0224337 A1 | 12/2003 | Shum et al. |
| 2003/0229446 A1 | 12/2003 | Boscamp et al. |
| 2004/0046692 A1 | 3/2004 | Robson et al. |
| 2004/0102931 A1 | 5/2004 | Ellis et al. |
| 2004/0116784 A1 | 6/2004 | Gavish |
| 2004/0199056 A1 | 10/2004 | Husemann et al. |
| 2004/0203789 A1 | 10/2004 | Hammond et al. |
| 2004/0203873 A1 | 10/2004 | Gray |
| 2004/0240946 A1 | 12/2004 | Haun |
| 2004/0249846 A1 | 12/2004 | Randall et al. |
| 2005/0075214 A1 | 4/2005 | Brown et al. |
| 2005/0079905 A1 | 4/2005 | Martens |
| 2005/0096933 A1 | 5/2005 | Collins, III et al. |
| 2005/0121504 A1 | 6/2005 | Sanders et al. |
| 2005/0124463 A1 | 6/2005 | Yeo et al. |
| 2005/0172311 A1 | 8/2005 | Hjelt et al. |
| 2005/0177059 A1 | 8/2005 | Koivumaa et al. |
| 2005/0195094 A1 | 9/2005 | White |
| 2005/0197063 A1 | 9/2005 | White |
| 2005/0209050 A1 | 9/2005 | Bartels |
| 2005/0209887 A1 | 9/2005 | Pollner |
| 2005/0266961 A1 | 12/2005 | Shum et al. |
| 2005/0287499 A1 | 12/2005 | Yeager |
| 2006/0025282 A1 * | 2/2006 | Redmann ........................ 482/8 |
| 2006/0060068 A1 * | 3/2006 | Hwang et al. .................. 84/615 |
| 2006/0063980 A1 | 3/2006 | Hwang et al. |
| 2006/0082472 A1 | 4/2006 | Adachi et al. |
| 2006/0136173 A1 | 6/2006 | Case, Jr. et al. |
| 2006/0156356 A1 | 7/2006 | Sato et al. |
| 2006/0189360 A1 | 8/2006 | White |
| 2006/0240865 A1 | 10/2006 | White |
| 2006/0252602 A1 | 11/2006 | Brown et al. |
| 2007/0135225 A1 | 6/2007 | Nieminen et al. |

(56) References Cited

U.S. PATENT DOCUMENTS

| | | | |
|---|---|---|---|
| 2007/0156364 A1* | 7/2007 | Rothkopf | G06F 1/1626 702/117 |
| 2007/0159926 A1* | 7/2007 | Prstojevich | G04G 19/12 368/10 |
| 2007/0208531 A1 | 9/2007 | Darley et al. | |
| 2007/0219059 A1 | 9/2007 | Schwartz et al. | |
| 2007/0232455 A1 | 10/2007 | Hanoun | |
| 2007/0265138 A1 | 11/2007 | Ashby | |
| 2007/0275825 A1* | 11/2007 | O'Brien | A61B 5/1112 482/8 |
| 2007/0287596 A1 | 12/2007 | Case, Jr. et al. | |
| 2008/0051201 A1 | 2/2008 | Lore | |
| 2008/0051993 A1* | 2/2008 | Graham et al. | 701/209 |
| 2008/0058971 A1* | 3/2008 | Graham et al. | 700/90 |
| 2008/0059064 A1 | 3/2008 | Werner et al. | |
| 2008/0076637 A1 | 3/2008 | Gilley et al. | |
| 2008/0096726 A1 | 4/2008 | Riley et al. | |
| 2008/0200310 A1 | 8/2008 | Tagliabue | |
| 2008/0207115 A1* | 8/2008 | Lee et al. | 455/3.06 |
| 2008/0319661 A1 | 12/2008 | Werner et al. | |
| 2009/0047645 A1 | 2/2009 | Dibenedetto et al. | |
| 2009/0048044 A1 | 2/2009 | Oleson et al. | |
| 2009/0048070 A1 | 2/2009 | Vincent et al. | |
| 2009/0069156 A1 | 3/2009 | Kurunmäki et al. | |
| 2009/0233770 A1* | 9/2009 | Vincent et al. | 482/8 |
| 2009/0262088 A1 | 10/2009 | Moll-Carrillo et al. | |
| 2009/0292178 A1 | 11/2009 | Ellis et al. | |
| 2010/0042427 A1 | 2/2010 | Graham et al. | |
| 2010/0045463 A1 | 2/2010 | Bradley et al. | |
| 2010/0062818 A1 | 3/2010 | Haughay, Jr. et al. | |
| 2010/0088023 A1 | 4/2010 | Werner | |
| 2010/0122208 A1 | 5/2010 | Herr et al. | |
| 2010/0129780 A1 | 5/2010 | Homsi et al. | |
| 2010/0184563 A1 | 7/2010 | Molyneux et al. | |
| 2010/0184564 A1 | 7/2010 | Molyneux et al. | |
| 2010/0216601 A1 | 8/2010 | Saalasti et al. | |
| 2010/0292050 A1 | 11/2010 | DiBenedetto et al. | |
| 2010/0292599 A1 | 11/2010 | Oleson et al. | |
| 2010/0292600 A1 | 11/2010 | Dibenedetto et al. | |
| 2010/0311544 A1 | 12/2010 | Robinette et al. | |
| 2011/0003665 A1* | 1/2011 | Burton | G04F 10/00 482/9 |
| 2011/0082641 A1 | 4/2011 | Werner et al. | |
| 2011/0087137 A1 | 4/2011 | Hanoun | |
| 2011/0098156 A1 | 4/2011 | Ng et al. | |
| 2011/0130916 A1* | 6/2011 | Mayer | G07C 5/008 701/31.4 |
| 2011/0170005 A1* | 7/2011 | Bornstein et al. | 348/555 |

FOREIGN PATENT DOCUMENTS

| | | |
|---|---|---|
| GB | 2257558 A | 1/1993 |
| JP | 63-144286 | 6/1988 |
| JP | 10-329452 | 12/1998 |
| JP | 2002-248187 | 9/2002 |
| JP | 2002-288381 | 10/2002 |
| JP | 2004-247954 | 9/2004 |
| JP | 2007312246 | 11/2007 |
| WO | WO 2007/069014 A1 | 6/2007 |
| WO | WO 2008/119266 A1 | 10/2008 |

OTHER PUBLICATIONS

GPSIII, Garmin Owner's Manual & Reference, 100 pages, Aug. 1997, Garmin Corp., Kansas, USA.
Garmin International, Inc., "NAVTALK; Cellular Phone/GPS Receiver; Owner's Manual and Reference Guide," 1999-2000, Garmin Corporation, 128 pages.
Baca et al., "Rapid Feedback Systems for Elite Sports Training," Pervasive Computing, IEEE vol. 5, Issue: 4, 2006, pp. 70-76.
Basari et al., "Field Measurement on Simple Vehicle-Mounted Antenna System Using a Geostationary Satellite," Vehicular Technology, IEEE Transactions vol. 59, Issue: 9, 2010, pp. 4248-4255.
Cavallo et al., "A step toward GPS/INS personal navigation systems: real-time assessment of gait by foot inertial sensing," Intelligent Robots and Systems, 2005, pp. 1187-1191.
Garmin International, Inc., "GPSII, Garmin Owner's Manual 7 Reference," Garmin Corp., Kansas, USA, Aug. 1996, 50 pages.
Garmin International, Inc., "GPSIII, Garmin Owner's Manual 7 Reference," Garmin Corp., Kansas, USA, Aug. 1997, 100 pgs.
Garmin International, Inc., "NAVTALK Cellular Phone/GPS Receiver Owner's Manual and Reference Guide," Garmin Corporation, 1999-2000, 64 pages.
Garmin LTD, NAVTALK, Product Information, 2002, 6 pages.
Li et al., "Hierarchical Cluster Analysis on Coolmax/Cotton Double-laced Effect Knitted Fabric's Subjective Sensations in Different Sports Conditions," Information Science and Engineering, ISISE '08, International Symposium, vol. 1, 2008, pp. 622-625.
Llosa et al., "Design of a Motion Detector to Monitor Rowing Performance Based on Wireless Sensor Networks," Intelligent Networking and Collaborative Systems, 2009, pp. 397-400.
Lodha et al., "Consistent visualization and querying of GIS databases by a location-aware mobile agent," Computer Graphics International, Jul. 2003, pp. 248-253.
Losada et al., "OISTI (an Oral-Interface System to provide Tourist-Information inside a car)," Proceedings of the International Conference on Information Technology: Coding and Computing, Apr. 2001, pp. 373-377.
Magellan Systems Corporation, "Magellan GPS, NAVDLX-10 User Guide," 1995, pp. 1-91.
Magellan Systems Corporation, "Magellen GPS Satellite Navigator Reference Guide Trailblazer XL," 1995, pp. 1-78.
Malkinson, T., "Current and emerging technologies in endurance athletic training and race monitoring," Science and Technology for Humanity (TIC-STH), 2009 IEEE Toronto International Conference, 2009, pp. 581-586.
Mann, S., "WearCam (The wearable camera): personal imaging systems for long-term use in wearable tetherless computer-mediated reality and personal photo/videographic memory prosthesis," Wearable Computers, Digest of Papers, Second International Symposium, Oct. 19-20, 1998, 8 pages.
Mehaffey et al., "Garmin's NavTalk Cell Phone and Road Map GPS Product Review" Revision 2, Nov. 2, 1999, 5 pgs.
Sawhney et al., "Speaking and Listening on the Run: Design for Wearable Audio Computing," Speech Interface Group, MIT Media Laboratory, Oct. 19-20, 1998, 11 pages.
Silva et al., "Homogeneous access to temporal data and interaction histories in visual interface for databases," User Interfaces to Data Intensive Systems, 1999, pp. 108-117.
Svendsen et al., "Adaptive antenna for handheld GPS receivers," Position Location and Navigation Symposium (PLANS), 2010, pp. 436-442.
Waegli et al., "Redundant MEMS-IMU integrated with GPS for performance assessment in sports," Position, Location and Navigation Symposium, 2008, pp. 1260-1268.
Wei et al., "A self-coherence anti-jamming GPS receiver," Signal Processing vol. 53, Issue 10, Part 1, Oct. 2005, pp. 3910-3915.
English Language Abstract of German Patent Publication No. DE 3320502 A1, European Patent Office, espacenet database Worldwide, (1983) (listed as document FP1 on the accompanying for PTO/SB08A).
English Language Abstract of Japanese Patent Publication No. JP 63144286 A, European Patent Office, espacenet database—Worldwide, (1986) (listed as document FP2 on the accompanying for PTO/SB08A).
English Language Abstract of Japanese Patent Publication No. JP 10329452 A, European Patent Office, espacenet database—Worldwide, (1998) (listed as document FP5 on the accompanying for PTO/SB08A).
English Language Abstract of Japanese Patent Publication No. JP 2002248187, European Patent Office, espacenet database—Worldwide, (2002) (listed as document FP6 on the accompanying for PTO/SB08A).

(56) References Cited

OTHER PUBLICATIONS

English Language Abstract of Japanese Patent Publication No. JP 2002288381, European Patent Office, espacenet database—Worldwide, (2002) (listed as document FP7 on the accompanying for PTO/SB08A).

English Language Abstract of Japanese Patent Publication No. JP 2004247954, European Patent Office, espacenet database—Worldwide, (2004) (listed as document FP8 on the accompanying for PTO/SB08A).

English Language Abstract of Japanese Patent Publication No. JP 2007312246, European Patent Office, espacenet database—Worldwide, (2007) (listed as document FP11 on the accompanying for PTO/SB08A).

* cited by examiner

| ZONE | COLOR | % OF MAX HR |
|---|---|---|
| ENERGY | BLUE | 65–75% |
| ENDURANCE | GREEN | 75–85% |
| STRENGTH | YELLOW | 85–90% |
| POWER | RED | 90–95% |

FIG. 10

| ZONE | COLOR | PACE |
|---|---|---|
| ENERGY | BLUE | 12-10 min./mi. |
| ENDURANCE | GREEN | 10-8 min./mi. |
| STRENGTH | YELLOW | 8-7 min./mi. |
| POWER | RED | 7-6 min./mi. |

RUN A RACE—10K RACE

READY FOR A LONGER RACE? CAPITALIZE ON SPEEDWORK, INTERVALS, RECOVERY WORKOUTS AND LONG RUNS TO BUILD THE ENDURANCE AND AEROBIC CAPACITY TO FINISH THE 10K.

CHOOSE THE LEVEL OF DIFFICULTY

| 1 | 2 | 3 | 4 | 5 | 6 | 7 |

314

LEVEL 4 - YOU CAN RUN FOR 30 MINUTES AND WANT TO FINISH IN THE MIDDLE OF THE 10K PACK. — 316

WHAT TO EXPECT
TEACH YOUR BODY TO WORK HARD WITH TOUGH YELLOW ZONE SPRINTS. GAUGE YOUR RACE EFFORT BY UNDERSTANDING YOUR SPEED FOR THE GREEN ZONE.

BENEFITS
FINISH A 10K IN UNDER 65 MINUTES. IMPROVE YOUR RUNNING SPEED AND FINISH THE RACE FEELING GREAT.

PLAN AT A GLANCE

◎ GO BACK

◎ PREVIEW WORKOUT LIST

RECOMMENDED SCHEDULE

| WORKOUTS | PER WEEK | WEEKS |
|---|---|---|
| 51 | 4 | 13 |

NEXT STEP–PERSONALIZE

| PERSONAL INFO | WORKOUT SETTINGS | DEVICE SETTINGS | PRIVACY AND SHARING |

DEVICES

① ☐ I HAVE A _____ PHONE (MODEL NNN-NNNN)

② NARRATION VOICE OPTIONS (CHOOSE UP TO 5)

```
CHINESE-CANTONESE: MALE          ENGLISH-UK: FEMALE
CHINESE-MANDARIN: FEMALE         ENGLISH-UK: MALE
FRENCH: FEMALE          ADD >    ENGLISH-US: FEMALE
GERMAN: MALE                     ENGLISH-US: MALE
ITALIAN: FEMALE       < REMOVE
JAPANESE: FEMALE
KOREAN: FEMALE
PORTUGESE-BRAZIL: FEMALE
RUSSIAN: MALE
SPANISH: FEMALE
```

③ ☐ SKIP WARM UP/COOL DOWN EXERCISES ON ALL WORKOUTS ⓘ

④ ☑ I HAVE _____ (MODEL NNN-NNNN)

NARRATION VOICE OPTIONS

[ ENGLISH – UK ▽ ]

⑤ STATS UPDATE ANNOUNCEMENTS DURING WORKOUT

DURING YOUR WORKOUT, YOUR VITALS WILL BE ANNOUNCED WHEN YOU CHOOSE TO HEAR AN UPDATE AND AUTOMATICALLY AFTER REACHING 25%, 50%, 75%, AND COMPLETION OF YOUR WORKOUT. CHOOSE WHICH STATS ARE ANNOUNCED DURING THESE UPDATES.

☐ REPEAT THE LATEST COACHING INSTRUCTION
☑ TIME ELAPSED
☑ CALORIES BURNED
☑ DISTANCE TRAVELED
☐ HEART RATE ZONE AT THE TIME
☐ HEART RATE VALUE AT THE TIME
☐ PACE AT THE TIME
☐ STRIDE RATE AT THE TIME

⑥ ACCESSORIES

SELECT THE ACCESSORIES YOU WILL BE WORKING OUT WITH SO KNOWS TO CONNECT TO THEM DURING YOUR WORKOUT.

☐ STRIDE RATE MONITOR (MODEL NNN-NNNN)

☐ HEART RATE MONITOR (MODEL NNN-NNNN)

FIG. 19

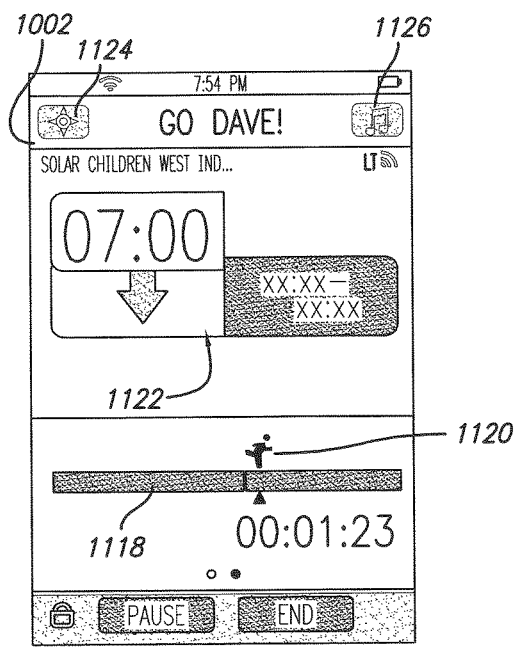
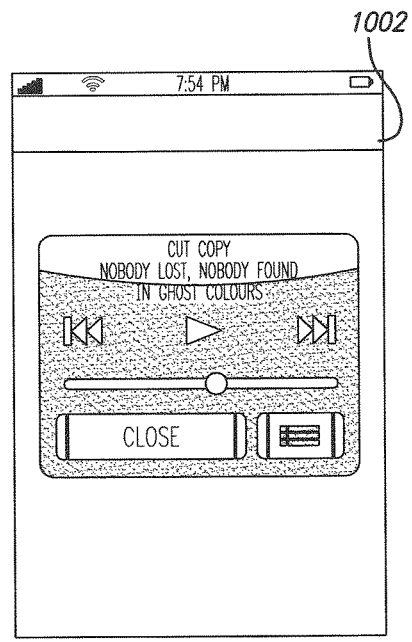
FIG. 32A
FIG. 32B

LOCATION-AWARE FITNESS MONITORING METHODS, SYSTEMS, AND PROGRAM PRODUCTS, AND APPLICATIONS THEREOF

CROSS-REFERENCE TO RELATED APPLICATIONS

This application is related to commonly owned U.S. patent application Ser. No. 12/836,421, titled "Fitness Monitoring Methods, Systems, and Program Products, and Applications Thereof," and U.S. patent application Ser. No. 12/836,401, now U.S. Pat. No. 8,493,882, titled "Methods, Systems, and Program Products for Controlling the Playback of Music," filed on the same day herewith, each of which is incorporated herein by reference in its entirety.

FIELD OF THE INVENTION

The present invention generally relates to fitness monitoring. More particularly, the present invention relates to location-aware fitness monitoring methods, systems, and program products, and applications thereof.

BACKGROUND OF THE INVENTION

Exercise is important to maintaining a healthy lifestyle and individual well-being. Accordingly, many individuals want to participate in an exercise program. The most successful exercise programs are ones tailored to a fitness level of an individual and aimed at assisting the individual to achieve one or more specific fitness or exercise goals.

Sports trainers, as well as other exercise and fitness professionals, are available to assist individuals in developing exercise programs appropriate for their individual fitness levels and their specific fitness or exercise goals. Hiring such professionals, however, can be expensive. Furthermore, the busy schedules of many individuals make it difficult for these individuals to set aside time to meet with an exercise and fitness professional on a routine basis. Thus, many individuals forego using the services of exercise and fitness professionals, and they never achieve the benefits that can be obtained from an exercise program tailored, for example, to one's fitness level.

Technology has resulted in the development of portable devices that are capable of monitoring the performance of an individual supporting a portable device during a workout. These portable fitness monitoring devices may transmit and receive a variety of information to and from remote server computers via networks in order to assist the individual in their fitness or exercise goals.

Satellite navigation systems, such as the GPS, GLONASS, and Galileo systems, allow a device having a suitable receiver to determine the device's geographical location within a few meters, using time signals transmitted by radio from satellites. Portable devices including satellite navigation system receivers may use this information to measure or calculate the location, distance traveled, and/or speed of the portable device as it moves.

What is needed are improved fitness monitoring methods, systems, and program products for use with satellite navigation system-enabled portable fitness monitoring devices that will allow individuals to use satellite navigation system data, among other things, to aid in the execution of athletic workouts, to aid in the collection of athletic performance parameters, to more accurately determine athletic performance parameters, to provide location and/or movement based feedback, to better use data generated from past performances to gauge their improvement, to create visualizations of their past performances, and/or to stay motivated.

BRIEF SUMMARY OF THE INVENTION

The present invention relates to a method for providing feedback to an athlete via a portable fitness monitoring device, the method including the steps of calculating a plurality of speed points from a plurality of time-stamped position points, calculating an output speed based on at least some of the plurality of speed points, determining that the output speed is outside of a predetermined speed range, receiving acceleration data from an accelerometer, determining that a recent speed change has occurred based on the acceleration data, providing feedback to the athlete via the portable fitness monitoring device, wherein the feedback is provided in response to the determination that the output speed is outside of the predetermined speed range, and in response to the determination that the recent speed change has occurred.

The present invention may also relate to a method for execution by a portable fitness monitoring device, the method including the steps of launching a portable fitness monitoring application on the portable fitness monitoring device, receiving position data from a satellite positioning system receiver of the portable fitness monitoring device, determining that the position data indicates that the portable fitness monitoring device is moving, beginning execution of a workout routine in response to the determination that the portable fitness monitoring device is moving, determining that the position data indicates that the portable fitness monitoring device is not moving, and ending execution of a workout routine in response to the determination that the portable fitness monitoring device is not moving.

The present invention may further relate to a method for execution by a portable fitness monitoring device, the method including the steps of launching a portable fitness monitoring application on the portable fitness monitoring device, receiving position data from a satellite positioning system receiver of the portable fitness monitoring device, determining that the position data indicates that the portable fitness monitoring device is moving, beginning music playback in response to the determination that the portable fitness monitoring device is moving, determining that the position data indicates that the portable fitness monitoring device is not moving, and ending music playback in response to the determination that the portable fitness monitoring device is not moving.

The present invention may also relate to a tangible computer program product comprising a non-transitory computer readable medium having computer program logic recorded thereon for enabling at least one processor to cause the graphical display of performance parameter information regarding an athlete's performance during a workout as a function of time to a user at a computer, and cause the graphical display of the title of a music track that was played for the athlete by a portable fitness monitoring device during the workout, wherein the graphical display of the title of a music track occurs in response to the user specifying a particular point in time during the workout.

Further aspects, features, and advantages of the present invention, as well as the structure and operation of the various embodiments of the present invention, are described in detail below with reference to the accompanying drawings.

BRIEF DESCRIPTION OF THE DRAWINGS/FIGURES

The accompanying drawings, which are incorporated herein and form a part of the specification, illustrate the present invention by way of example, and not by way of limitation, and, together with the description, further serve to explain the principles of the invention and to enable a person skilled in the pertinent art to make and use the invention.

FIG. 10 is a table that illustrates heart rate zone ranges according to an embodiment of the present invention.

FIG. 11 is a table that illustrates pace zone ranges according to an embodiment of the present invention.

FIG. 12 is an exemplary GUI window according to an embodiment of the present invention.

FIG. 13 is an exemplary GUI window according to an embodiment of the present invention.

FIG. 14 is an exemplary GUI window according to an embodiment of the present invention.

FIG. 15 is an exemplary GUI window according to an embodiment of the present invention.

FIG. 19 is an exemplary GUI window according to an embodiment of the present invention.

FIGS. 32A and 32B are exemplary GUI windows according to an embodiment of the present invention.

FIG. 49 is an exemplary GUI window according to an embodiment of the present invention.

FIG. 51 is an exemplary GUI window according to an embodiment of the present invention.

DETAILED DESCRIPTION OF THE INVENTION

Figure 1:
FIG. 1 is an illustration of an athlete engaged in an activity according to an embodiment of the present invention.

The present invention will now be described in detail with reference to embodiments thereof as illustrated in the accompanying drawings. References to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

To assist the reader, the Detailed Description has been broken into various subsections, as follows: A. General Description of Features of the Methods, Systems, and Program Products; B. Portable Fitness Monitoring Devices and Server Systems; C. Exemplary Pre-Activity Data Processing and Feedback Aspects; D. Exemplary Data Processing and Feedback Aspects During an Activity; E. Exemplary Post-Activity Data Processing and Feedback Aspects; F. Other Features; and G. Conclusion.

A. GENERAL DESCRIPTION OF FEATURES OF THE METHODS, SYSTEMS, AND PROGRAM PRODUCTS

In general, the methods, systems, and program products of the present invention may be used to provide fitness monitoring services to athletes. In at least some embodiments of the present invention, a portable fitness monitoring device and a computer server system may interact with one another to provide the fitness monitoring services.

In one embodiment, the athlete may utilize the portable fitness monitoring device during a physical activity. In another embodiment, the athlete may interact with the computer server system before, during, and/or after the physical activity.

The portable fitness monitoring device may be adapted to measure various performance parameters associated with the athlete's physical activities, to provide feedback to the athlete during the activities, to send information to the server system, and/or to receive information from the server system. The server system may be adapted to process performance information associated with the athlete's activities, to provide feedback to the athlete before, during, and/or after the physical activities, to send information to the portable fitness monitoring device, and/or to receive information from the portable fitness monitoring device.

In one embodiment, portable fitness monitoring device and a computer server system may interact with one another via a wireless wide area network. In another embodiment, the server system may present information to the athlete via the athlete's portable fitness monitoring device. In a further embodiment, the server system may present information to a user (who may or may not be the athlete) via a remote computer (which may or may not be the portable fitness monitoring device).

In one exemplary embodiment of the present invention, the athlete may interact with the portable fitness monitoring device and the server system in various ways at various times as follows.

First, prior to engaging in a physical activity, the athlete may access a website provided by the server from a remotely located personal computer. The athlete stationed at the remotely located personal computer may use the website to plan and schedule a prospective physical activity. Alternatively, the athlete may plan and schedule a prospective physical activity by accessing the website from the athlete's portable fitness monitoring device. In one embodiment, the version of the accessible from the athlete's portable fitness monitoring device may be simplified or otherwise modified to optimize it for display on a relatively small screen.

Next, the athlete may engage in the planned scheduled activity while utilizing the portable fitness monitoring device. Alternatively, the athlete may engage in an unplanned, unscheduled activity. During the activity, the portable fitness monitoring device may measure various performance parameters associated with the athlete's physical activity and provide feedback to the athlete during the activity. Some of the feedback provided to the athlete during the activity may depend on information received from the server before or during the activity. The portable fitness monitoring device may also send information to the server about the athlete's performance before, during, or after the activity.

Finally, after completing the activity, the athlete may again access the website provided by the server from the remotely located personal computer. The athlete stationed at the remotely located personal computer may use the website to review and analyze performance information associated with the activity. Alternatively, the athlete may review and analyze performance information associated with the activity by accessing the website from the athlete's portable fitness monitoring device. In one embodiment, the version of the accessible from the athlete's portable fitness monitoring device may be simplified or otherwise modified to optimize it for display on a relatively small screen.

At various points before, during, or after the activity, processors of the portable fitness monitoring device and/or the server may receive, process, send and/or display a variety of data relating to the athlete's performance.

Athletes who utilize embodiments of the present invention may actively participate in a variety of physical activities including, but not limited to, running, walking, biking, skating, swimming, skiing, performing aerobic exercises, weight lifting, or participating in various individual or team sports. Accordingly, terms such as, for example, "athlete," "runner," and "individual" may be referred to herein interchangeably, and may generally refer to any person who conducts a physical activity in accordance with embodiments of the present invention.

Furthermore, while the term "user" may include the athlete who conducts a physical activity, the term "user" may also be used herein to refer to a user other than the athlete conducting the physical activities of interest. In other words, as described in further detail below, other users in addition to the athlete-user, such as coaches or friends, may be able to interact with the system of the present invention.

More detailed examples of embodiments of the present invention that may utilize a portable fitness monitoring device and/or a computer server system to provide fitness monitoring services to athletes are provided below.

B. PORTABLE FITNESS MONITORING DEVICES AND SERVER SYSTEMS

Figure 2:
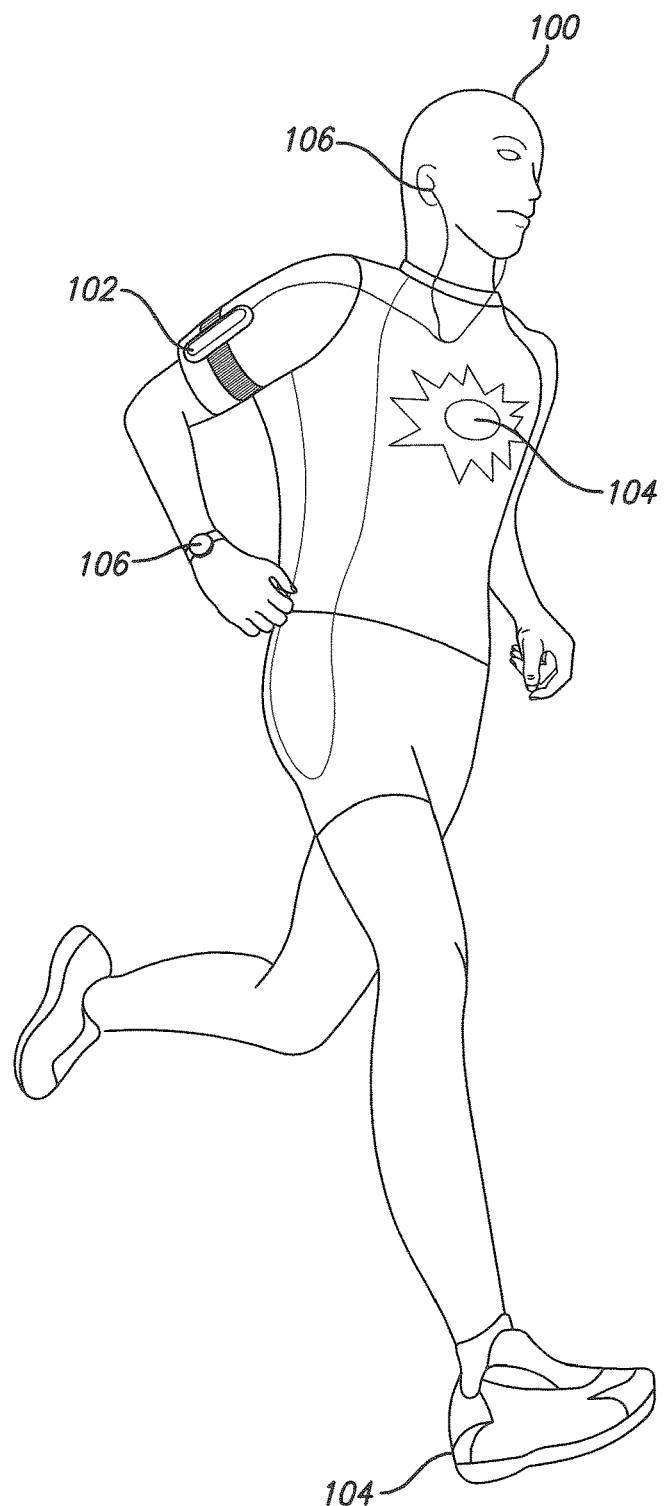
FIG. 2 is an illustration of an athlete engaged in an activity according to an embodiment of the present invention.

As illustrated in FIGS. 1 and 2, an athlete 100 engaged in physical activity may be equipped with a portable fitness monitoring device 102. The portable fitness monitoring device 102 may be worn, carried, or otherwise supported by the athlete 100 during the physical activity. The portable fitness monitoring device 102 may be adapted to measure and/or calculate various performance parameters associated with the athlete's 100 physical activity, as explained in further detail below. The term "performance parameters" may include both physical parameters and physiological parameters associated with the athlete's 100 physical activity. Physical parameters measured and/or calculated may include, for example, time, location, distance, speed, pace, stride count, stride length, stride rate, and/or elevation. Physiological parameters measured and/or calculated may include, for example, heart rate, respiration rate, blood oxygen level, blood flow, hydration status, calories burned, muscle fatigue, and/or body temperature.

In an embodiment, performance parameters may also include mental or emotional parameters such as, for example, stress level or motivation level. Mental and emotional parameters may be measured and/or calculated directly or indirectly either through posing questions to the athlete 100 or by measuring things such as, for example, trunk angle or foot strike characteristics while running.

The portable fitness monitoring device 102 may be a device such as, for example, a mobile phone, a personal digital assistant, a music file player (e.g. and MP3 player), a tablet computer, an intelligent article for wearing (e.g. a fitness monitoring garment, wrist band, or watch), a dongle (e.g. a small hardware device that is capable of physically coupling to a first electronic device and/or wirelessly coupling to additional electronic devices), or any other suitable dedicated or non-dedicated portable fitness monitoring device 102. Suitable devices may include, for example, the devices disclosed in commonly owned U.S. patent application Ser. No. 11/892,023, titled "Sports Electronic Training System, and Applications Thereof," and commonly owned U.S. patent application Ser. No. 12/467,944, titled "Portable Fitness Monitoring Systems, and Applications Thereof," each of which is incorporated herein by reference in its entirety.

The portable fitness monitoring device 102 may include or communicate with one or more sensors 104 for detecting information used to measure and/or calculate performance parameters. In one embodiment of the present invention, as shown in FIG. 1, the portable fitness monitoring device 102 itself may include a sensor 104. In other words, the sensor 104 may be integrally coupled to and/or included within the same housing as the portable fitness monitoring device 102. Such a sensor 104 may be, for example, a sensor 104 for detecting information that may be used to measure and/or calculate the athlete's 100 location, distance traveled, and/or speed.

In another embodiment, sensors 104 may be physically separate from the portable fitness monitoring device 102. In other words, these sensors 104 may not be integrally coupled to or included within the same housing as the portable fitness monitoring device 102. In contrast, in such an embodiment, these sensors 104 may be in wired or wireless communication with the portable fitness monitoring device 102. For example, in the embodiment of FIG. 2, a sensor 104 for detecting information that may be used to measure and/or calculate the athlete's 100 heart rate is coupled to the athlete's 100 chest, while a sensor 104 for detecting information that may be used to measure and/or calculate the athlete's 100 distance traveled and/or speed is coupled to the athlete's 100 shoe.

Suitable sensors 104 may include, but not be limited to, positioning system receivers (e.g. GPS receivers), accelerometers, pedometers, pulsimeters, thermometers, or other sensors 104 for detecting information that may be used to measure and/or calculate performance parameters.

The portable fitness monitoring device 102 may include or communicate with one or more portable output devices 106. The portable output devices 106 may be adapted to convey information to the athlete 100 in a variety of ways such as, for example, visually, audibly, and/or tactilely (e.g. via a vibrating element), either alone or in combination.

In some embodiments of the present invention, the portable fitness monitoring device 102 itself may include output device 106. In other words, the output device 106 may be integrally coupled to and/or included within the same housing as the portable fitness monitoring device 102. In other embodiments, the output device 106 may be physically separate from the portable fitness monitoring device 102. In other words, the output device 106 may not be integrally coupled to or included within the same housing as the portable fitness monitoring device 102. In contrast, in such embodiments, the output device 106 may be in wired or wireless communication with the portable fitness monitoring device 102. In still further embodiments, the portable fitness monitoring system may include multiple portable output devices 106.

In one embodiment of the present invention, as shown in FIG. 1, the portable fitness monitoring device 102 itself may include a visual display output device 106, while a separate audible output device 106 (e.g. headphones or a speaker) may be in wired or wireless communication with the portable fitness monitoring device 102.

In another embodiment, as shown in FIG. 2, while the portable fitness monitoring device 102 itself does include a output device 106, a separate output device 106 (e.g. a wrist band having a visual display) may be in wireless communication with the portable fitness monitoring device 102. In addition, a separate audible output device 106 (e.g. headphones) may be in wired or wireless communication with the portable fitness monitoring device 102.

In embodiments where a separate visual display output device 106 is provided, the separate visual display output device 106 may take many different forms. For example, the separate portable visual display output device 106 may be a wrist watch. As a further example, in one embodiment, the separate portable visual display output device 106 may be a wristband having one or more visual displays, such as the devices disclosed in U.S. patent application Ser. No. 12/467,948, titled "Portable Fitness Monitoring Systems with Displays, and Applications Thereof," which is incorporated herein by reference in its entirety. The separate visual display output device 106 may be capable of displaying, for example, numerical performance parameter information or color-coded performance zone related information, as described in further detail below.

Figure 3:
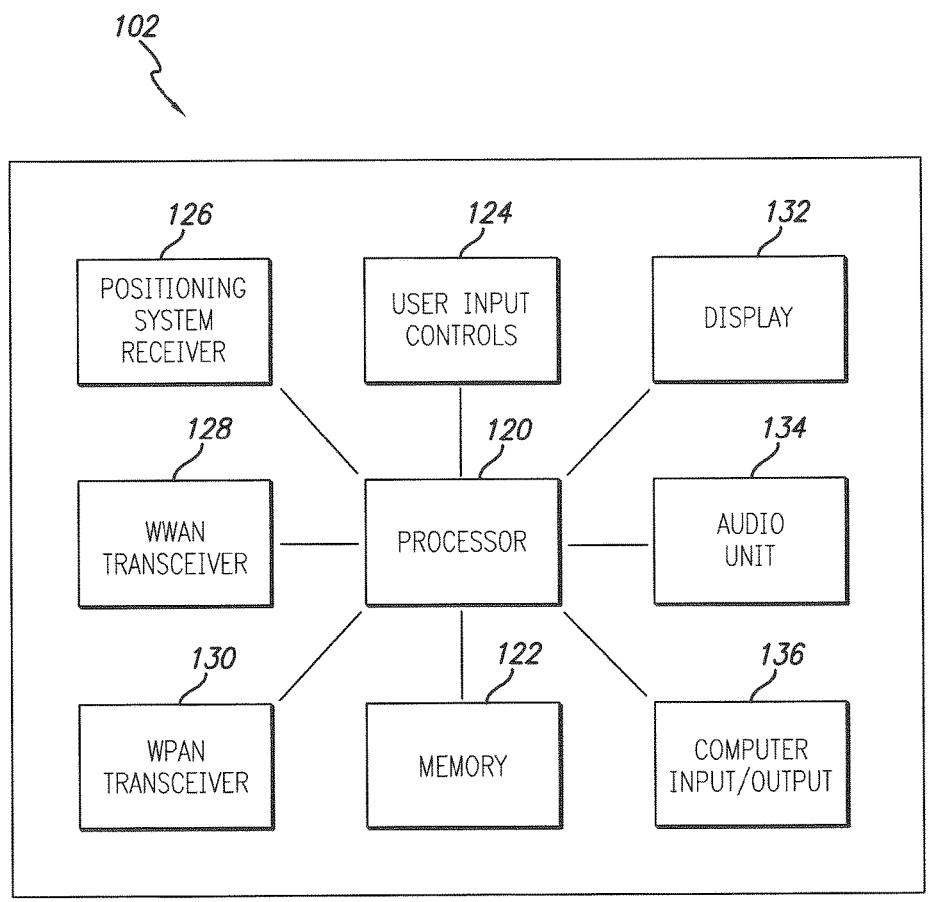
FIG. 3 is a block diagram of components of a portable fitness monitoring device according to an embodiment of the present invention.
Figure 4:
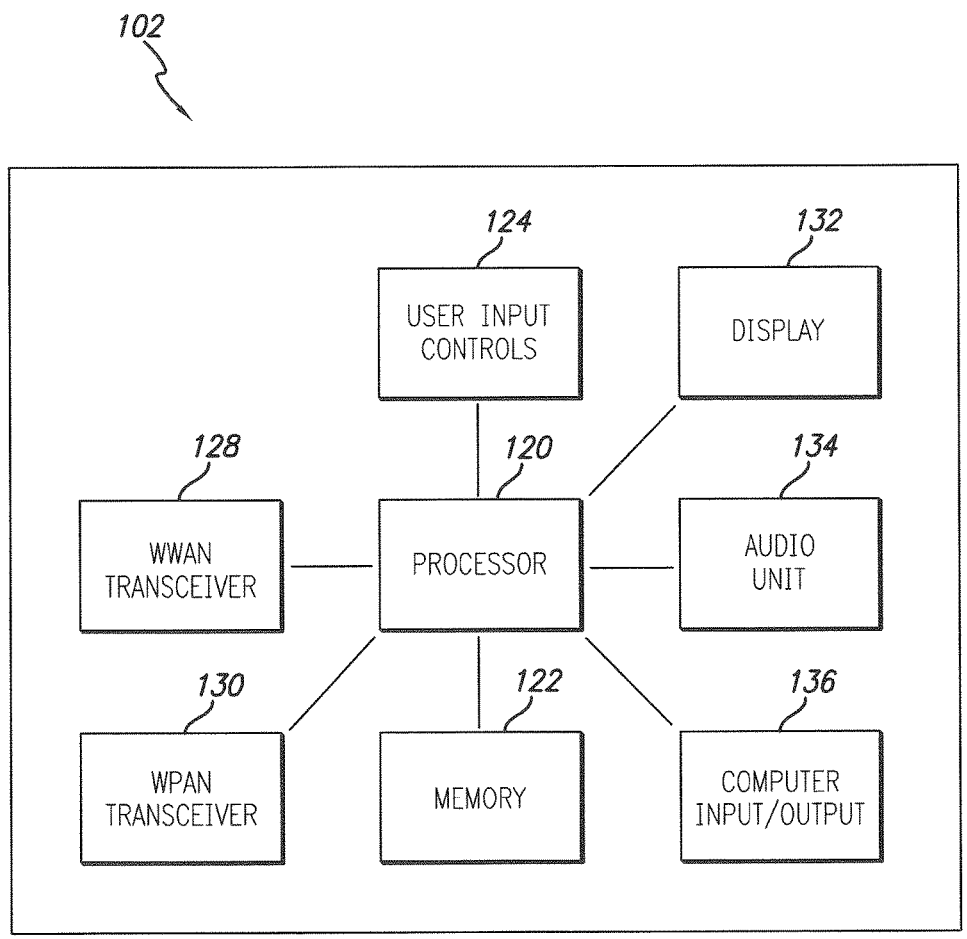
FIG. 4 is a block diagram of components of a portable fitness monitoring device according to an embodiment of the present invention.

FIG. 3 is a block diagram of exemplary components of a portable fitness monitoring device 102 according to an embodiment of the present invention. With reference to FIG. 3, the portable fitness monitoring device 102 may include a processor 120, a memory 122, user input controls 124, a positioning system receiver 126, a wireless wide area network (WWAN) transceiver 128, a wireless personal area network (WPAN) transceiver 130, a visual display 132, an audio unit 134, and a computer input/output 136. These components may be operatively connected to carry out the functionality of the portable fitness monitoring device 102, as is described in further detail below. In other embodiments, one or more of these components may be omitted, or additional components may be included. For example, as shown in FIG. 4, the portable fitness monitoring device 102 may not include a positioning system receiver 126.

The processor 120 of the portable fitness processing device 102 may be adapted to implement application programs that are stored in the memory 122, such as those described in further detail below. For example, in one embodiment, the processor 120 may be adapted to execute a workout routine. The processor 120 may also be capable of implementing analog or digital signal processing algorithms, such as, for example, those disclosed in U.S. patent application Ser. No. 11/892,023, titled "Sports electronic training system, and applications thereof," the disclosure of which has previously been incorporated herein in its entirety. The processor 120 may be operatively connected to the memory 122, the user input controls 124, the positioning system receiver 126, the WWAN transceiver 128, the WPAN transceiver 130, the visual display 132, the audio unit 134, and the computer input/output 136.

The memory 122 may be adapted to store application programs used to implement aspects of the functionality of the portable fitness monitoring system described herein. The memory 122 may also be adapted to store other data and information, as described in further detail below. For example, the memory 122 may be adapted to store recorded performance parameter information, workout routines, music tracks, and/or a playlist. The memory 122 may include both read only memory and random access memory.

The user input controls 124 may be used by the athlete 100 to interact with the portable fitness monitoring device 102. In an embodiment, user input controls 124 may include one or more physical input buttons, switches, and/or keys. In one embodiment, the user input controls 124 may include a track pad, scroll ball, and/or touch screen input controls (e.g. virtual input buttons, switches, and/or keys). In another embodiment, the user input controls 124 may include capacitance switches. In a further embodiment, the user input controls 124 may be voice-activated controls. The function of each of these user input controls 124 may be determined based on an operating mode of the portable fitness monitoring device 102.

In one embodiment, some or all of the user input controls 124 may not be integrally coupled to and/or included within the same housing as the portable fitness monitoring device 102 itself. For example, some or all of the user input controls 124 may be part of a separate visual display output device 106, such as a wristband. Depending on how the portable fitness monitoring device 102 is supported by the athlete's 100 body during an activity, locating some or all of the user input controls 124 on a wristband may provide the athlete 100 with easier access to actuating the user input controls 124. Commands entered via the user input controls could be transmitted to the portable fitness monitoring device 102 wirelessly, as described in further detail elsewhere.

The visual display 132 may be a visual display output device 106 integrally coupled to the portable fitness monitoring device 102, as described above. The visual display 132 may be used to visually display information to the athlete 100. In an embodiment, the visual display screen 132 may be, for example, a liquid crystal display (LCD), a light-emitting diode (LED) display, or a organic light-emitting diode (OLED) display. In another embodiment, a single display screen may include both the visual display 132 and the user input controls 124 in the form of touch screen input controls.

As described in further detail above with reference to FIG. 2, in one embodiment, one or more additional output devices 106 may not be integrally coupled to and/or included within the same housing as the portable fitness monitoring device 102 itself. For example, a separate visual display output device 106, such as those described above, may be in wired or wireless communication with the portable fitness monitoring device 102.

The audio unit 134 is used to process audio signals. The audio unit 134 may convert, for example, digital audio signals into amplified analog signals that can be used to drive an audible output device 106 (e.g. headphones or a speaker) in wired or wireless communication with the portable fitness monitoring device 102, as described above. The audio unit 134 may process a variety of audio signals such as, for example, signals associated with music tracks or verbal coaching and feedback.

The WPAN transceiver 130 may be capable of wireless communication with components of the portable fitness monitoring system supported by and/or in proximity to the athlete's 100 body. In one embodiment, the WPAN transceiver 130 is a low-power transceiver. The WPAN transceiver 130 may include an antenna, and may operate in an unlicensed frequency band, such as 2.4 GHz. In another embodiment, the WPAN transceiver may communicate using known wireless protocols, including, but not limited to, ANT and ANT+, by Dynastream Innovations, Bluetooth, Bluetooth LE, Bluetooth LET, or BlueRobin. Other known wireless communication protocols may be used. In an embodiment, a WPAN receiver or a WPAN transmitter capable of only unidirectional communication may be used in place of the WPAN transceiver 130. In one embodiment, the WPAN transceiver may be an infrared transceiver.

In one embodiment, the WPAN transceiver 130 may communicate with sensors 104 of the portable fitness monitoring system. In another embodiment, the WPAN transceiver 130 may communicate with visual, audible, and/or tactile portable output devices 106. In a further embodiment, a plurality of WPAN transceivers 130 may be employed for communicating with various sensors 104 and/or output devices 106.

In a further embodiment of the present invention, the portable fitness monitoring device 102 may be capable of connecting to an adapter that may supplement or replace the functionality of the WPAN transceiver 130. Such an adapter may be necessary if, for example, a particular sensor 104 or output device 106 is not capable of communicating with the WPAN transceiver 130 (e.g. the sensor 104 or output device 106 uses a different wireless transmission protocol than the WPAN transceiver 130), or if the portable fitness monitoring device 102 does not include a WPAN transceiver 130. In one embodiment, the adapter may include a male component for physically engaging a female component of the portable fitness monitoring device 102, where the female component is in communication with the processor 120 of the portable fitness monitoring device 102. For example, in an embodiment, the adapter may include a jack capable of plugging into an audio output jack of the portable fitness monitoring device 102. Because a wide variety of portable fitness monitoring devices 102 include similar audio output jacks (e.g. a 3.5 mm TRS jacks), the same type of adapter may advantageously be used with a variety of devices. Alternatively, the adapter may be a memory card such as, for example, a USB, mini USB, or SD card that is capable of being plugged into a connection port of the portable fitness monitoring device 102. Such memory cards may advantageously be used with a variety of devices.

In one embodiment, the adapter may be capable of receiving a data transmission encoded in accordance with a first data protocol and capable of sending a data transmission encoded in accordance with a second data protocol. Thus, the adapter may further facilitate the exchange of data between multiple components that otherwise may not be able to communicate in accordance with a single data protocol.

In contrast with the WPAN transceiver 130, the WWAN transceiver 128 may be a cellular transceiver that may be used to send and receive, for example, voice cellular telephone signals. The WAN transceiver 128 may also be used to exchange information with a computer network such as, for example, the internet, as described in further detail below. The WWAN transceiver 128 may include an antenna.

The portable fitness monitoring device 102 may also include a satellite-based positioning system receiver 126, such as a GPS- or Galileo-compatible receiver. Suitable positioning system receivers may include, for example, those disclosed in commonly owned U.S. patent application Ser. No. 10/759,289, titled "Location-aware fitness training device, methods, and program products that support real-time interactive communication and automated route generation," which is incorporated herein by reference in its entirety. In one embodiment, the positioning system receiver 126 may function as a sensor 104 integrally coupled to the portable fitness monitoring device 102, and may allow the portable fitness monitoring device 102 to detect information that may be used to measure and/or calculate GPS waypoints, time, location, distance traveled, speed, and/or calories.

The computer input/output 136 may be any input/output device or transceiver capable of wired or wireless communication with a personal computer 114. In one embodiment, the computer input/output 136 may be a USB port capable of receiving a USB hardwire cable for connecting the portable fitness monitoring device 102 to the personal computer 114. Alternatively, the computer input/output 136 may be an audio jack or a memory card slot, as described above. In some embodiments, a separate computer input/output 136 may not be necessary if the portable fitness monitoring device 102 and the computer 114 are capable of communicating wirelessly via, for example, the WPAN transceiver 130 or the WWAN transceiver 128.

Figure 5:
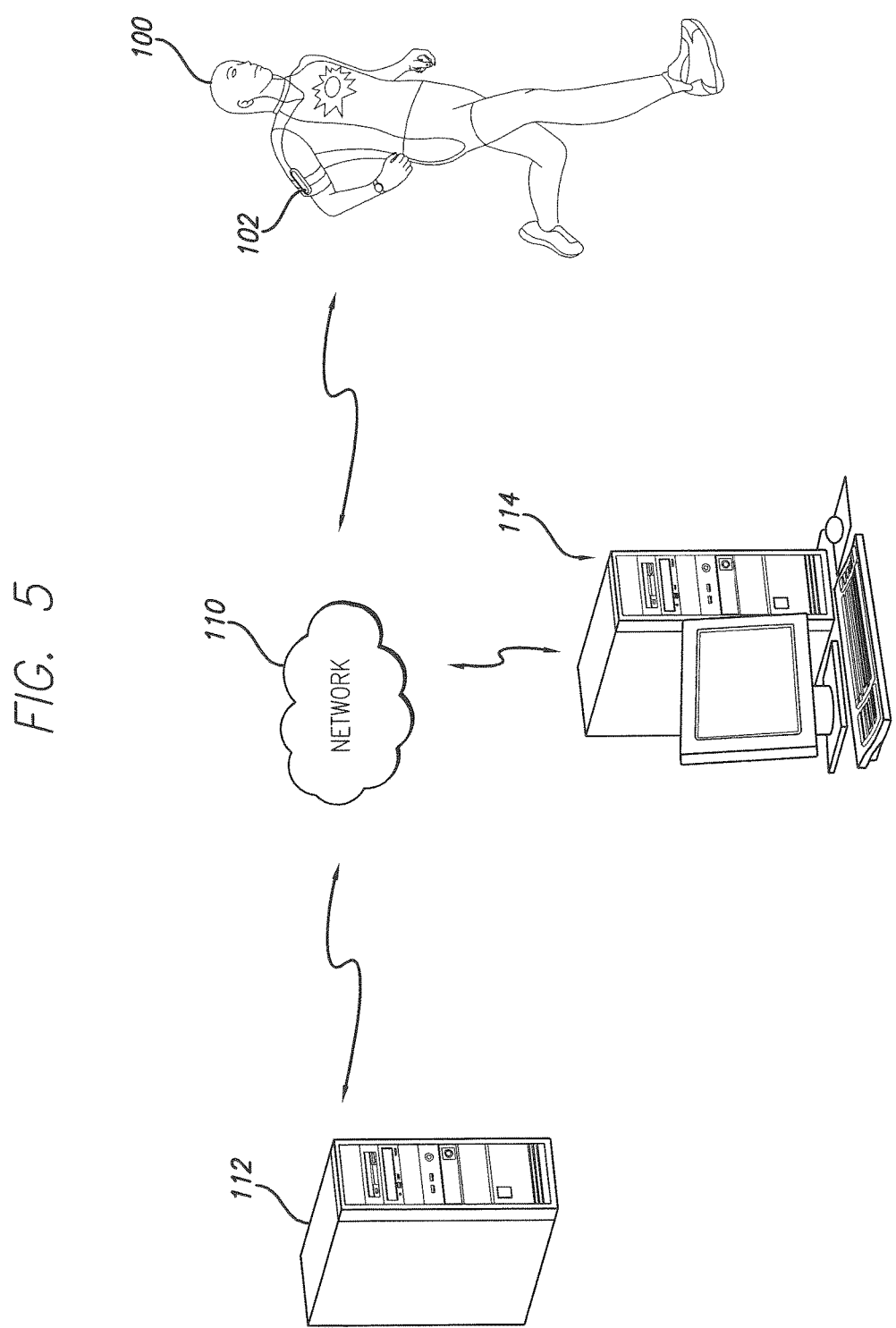
FIG. 5 is an illustration of a portable fitness monitoring device communicating with a server according to an embodiment of the present invention.

According to an embodiment of the present invention, information may be communicated between the portable fitness monitoring device 102 and one or more external elements. In addition, the external elements themselves may communicate between one another. As illustrated in FIG. 5, these external elements may include, for example, a network 110, a computer server system 112, and/or a personal computer 114.

In an embodiment, the network 110 may be the internet. The internet is a worldwide collection of servers, routers, switches and transmission lines that employ the Internet Protocol (TCP/IP) to communicate data. In an alternate embodiment, the network may be a private intranet.

In one embodiment, a user (who may or may not be the athlete 100) stationed at the personal computer 114 located remotely from the server 112 may communicate with the server 112 via the network. For example, as explained in further detail below, the user may use a website provided by the server 112 to plan and schedule a prospective physical activity to be conducted by the athlete 100 using the portable fitness monitoring device 102. After the activity has been conducted, the user may also use the website provided by the server 112 to review and analyze performance information associated with the activity. Alternatively, as described in further detail below, an athlete-user 100 may access the website before and after the activity directly from their portable fitness monitoring device 102. In one embodiment, the version of the accessible from the athlete's portable fitness monitoring device may be simplified or otherwise modified to optimize it for display on a relatively small screen.

In another embodiment, the portable fitness monitoring device 102 may communicate wirelessly with server 112 via the network 110. Such communication may be achieved, for example, by way of the WWAN transceiver 128 of the portable fitness monitoring device 102 utilizing a wide area network. Alternatively, communication may be achieved by way of the WPAN transceiver 130.

For example, the portable fitness monitoring device 102 may communicate with a WWAN communications system such as that employed by mobile telephones. For example, a WWAN communication system may include a plurality of geographically distributed communication towers and base station systems. Communication towers may include one or more antennae supporting long range two-way radio frequency communication wireless devices, such as the portable fitness monitoring device 102. The radio frequency communication between antennae and the portable fitness monitoring device 102 may utilize radio frequency signals conforming to any known or future developed wireless protocol, for example, GSM, GPRS, EDGE, EV-DO, UMTS, LTE, CDMA, AMPS, IEEE 802.x (e.g., IEEE 802.16 (WiMAX)), etc. The information transmitted over-the-air by the base station systems and the cellular communication towers to the portable fitness monitoring device 102 may be further transmitted to or received from one or more additional circuit-switched or packet-switched communication networks, including, for example, the internet.

Wireless communication between the portable fitness monitoring device 102 and the server 112 via the network 110 may occur before, during, and/or after an athletic performance conducted using the portable fitness monitoring device 102, as explained in further detail below. Prior to the activity, the server 112 may send, for example, activity goal or route information to the portable fitness monitoring device 102. For example, the server 112 may send one or more workout routines to the portable fitness monitoring device 102. During the activity, the portable fitness monitoring device 102 may send, for example, real-time performance information to the server 112, and in response the server 112 may send, for example, real-time feedback to the portable fitness monitoring device 102. In one embodiment, this communication during the activity may occur as a result of and/or simultaneously with the execution of a workout routine by the portable fitness monitoring device 102. After the activity, the portable fitness monitoring device 102 may send, for example, complete activity performance information to the server 112, and in response the server 112 may send, for example, post-activity analysis to the portable fitness monitoring device 102.

Figure 6:
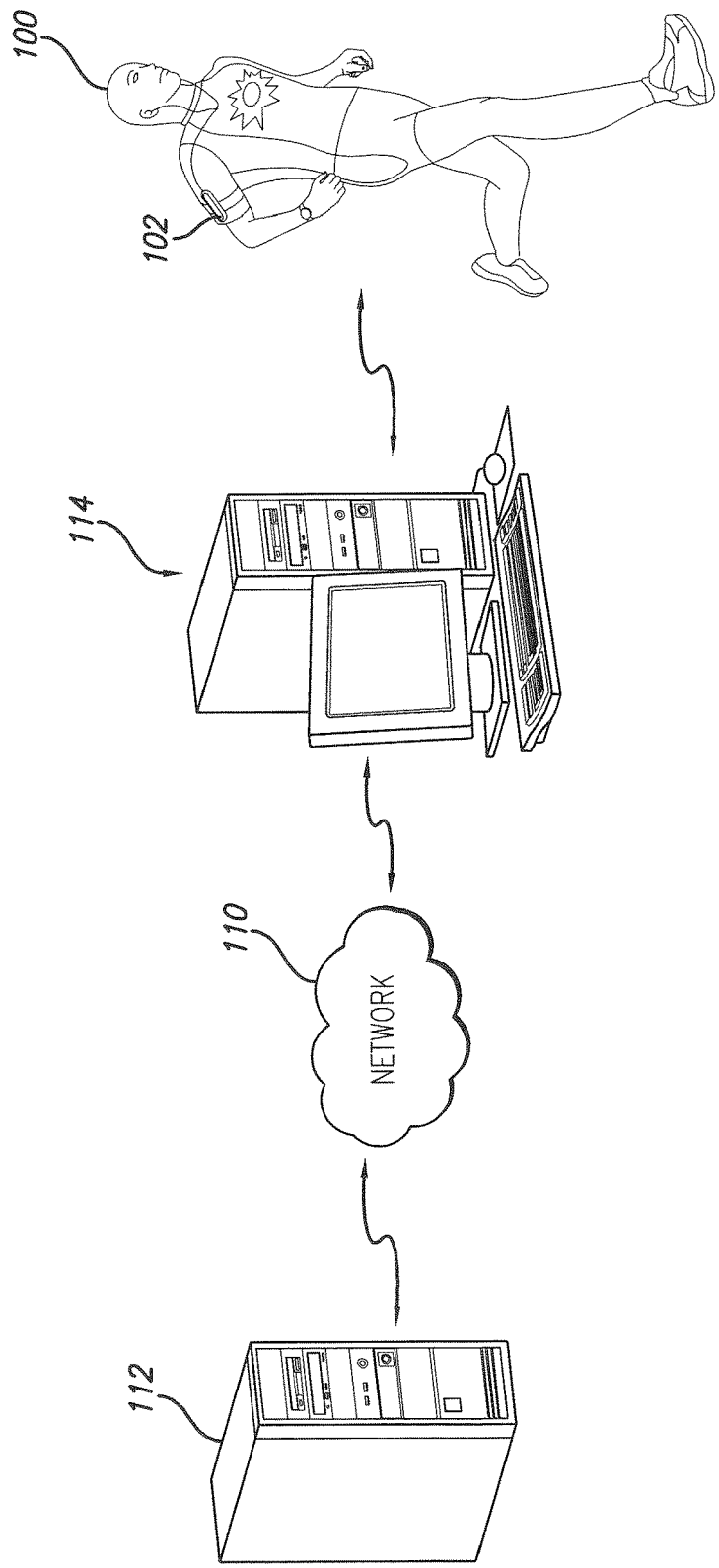
FIG. 6 is an illustration of a portable fitness monitoring device communicating with a server according to an embodiment of the present invention.

In another embodiment, as shown in FIG. 6, the portable fitness monitoring device 102 may communicate indirectly with the server 112 through the personal computer 114. Communication between the portable fitness monitoring device 102 and the personal computer 114 may be achieved, for example, using wired, WPAN, or WWAN communications.

As will be appreciated by those of ordinary skill in the art, wired communication between the portable fitness monitoring device 102 and the personal computer 114 may be achieved, for example, by placing the portable fitness monitoring device 102 in a docking unit that is attached to the personal computer 114 using a communications wire plugged into a communications port of the personal computer 114.

In another embodiment, wired communication between the portable fitness monitoring device 102 and the personal computer 114 may be achieved, for example, by connecting a cable between the portable fitness monitoring device 102 and the computer 114. The computer input/output 136 of the portable fitness monitoring device 102 and a communications port of the computer 114 may include USB ports. The cable connecting the portable fitness monitoring device 102 and the computer 114 may be a USB cable with suitable USB plugs including, but not limited to, USB-A or USB-B regular, mini, or micro plugs. Alternatively, the cable may be a audio-jack-to-USB cable.

Wired, WPAN, or WWAN communication between the portable fitness monitoring device 102 and the personal computer 114 may occur before and/or after an athletic performance is conducted using the portable fitness monitoring device 102 if the athlete 100 is in relatively close proximity to the personal computer 114, as explained in further detail below.

Figure 7:
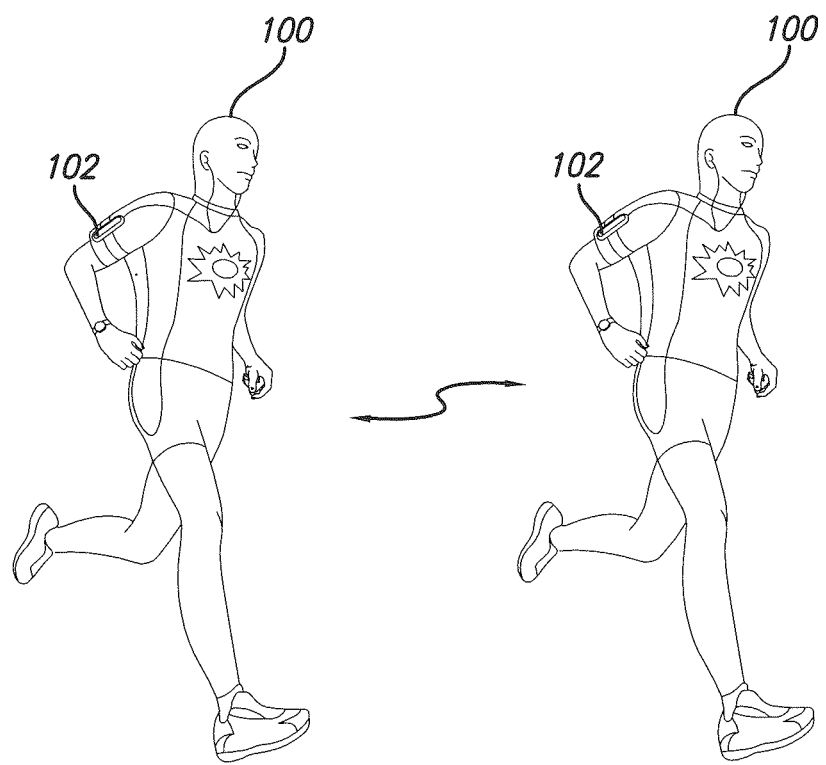
FIG. 7 is an illustration of one athlete's portable fitness monitoring device communicating with another athlete's portable fitness monitoring device according to an embodiment of the present invention.

In one embodiment, as shown in FIG. 7, one athlete's 100 portable fitness monitoring device 102 may be capable of communicating with another athlete's 100 portable fitness monitoring device 102. Communication may occur directly between the devices 102, or via a network 110. Such communication may occur wirelessly or via a hardwire connection, as explained above.

According to embodiments of the fitness monitoring service of the present invention, a wide variety of information may be communicated between any of the personal fitness monitoring device 102, the personal computer 114, the network 110, and the server 112. Such information may include, for example, performance parameters, training advice, training plans, workout routines, calendar data, route information, music, videos, text, images, voice communications, settings, software, and firmware, as described in further detail below.

Figure 8:
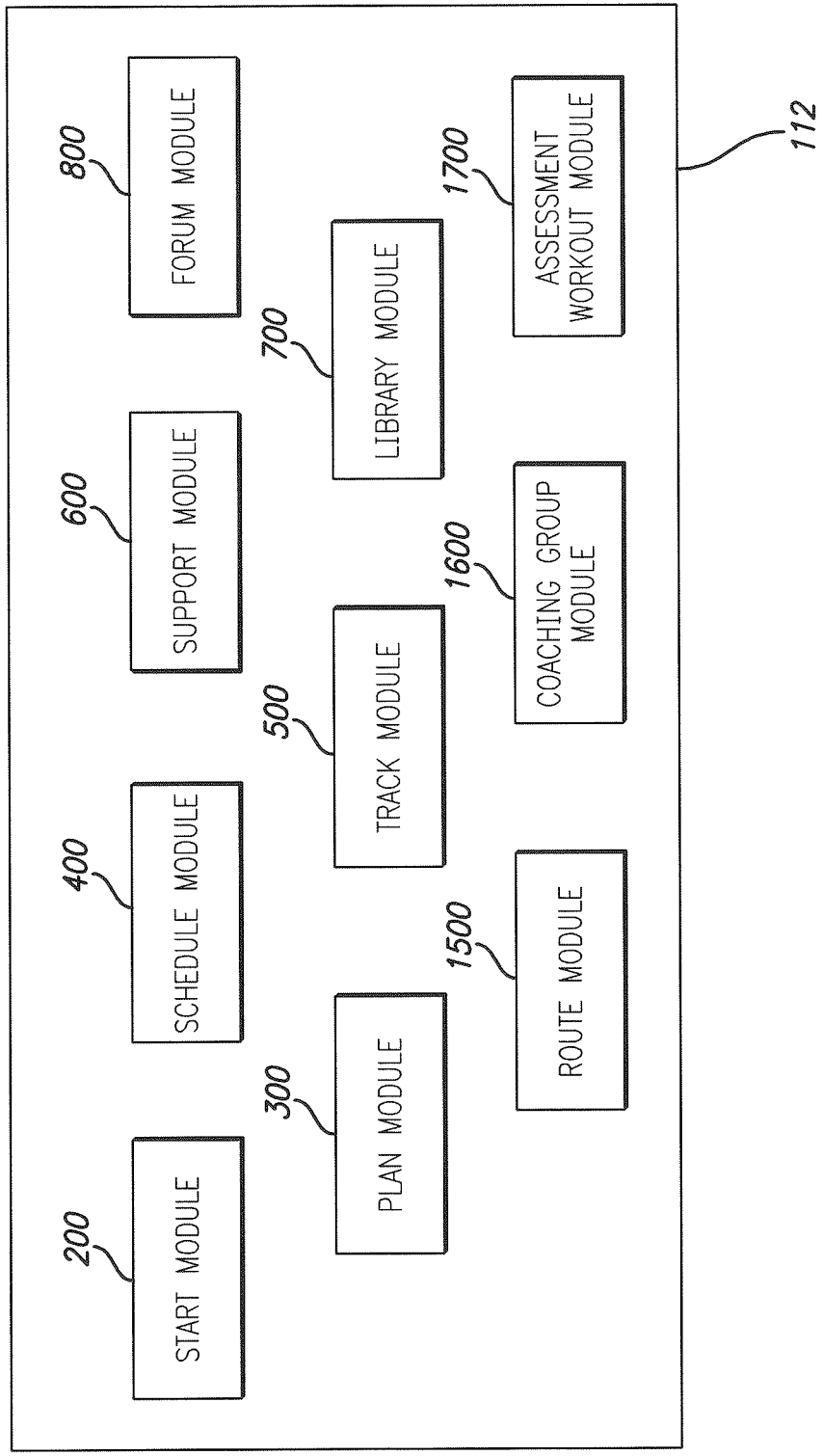
FIG. 8 is a block diagram of an exemplary software configuration of a server according to an embodiment of the present invention.

FIG. 8 is a diagram of an exemplary software configuration of the server 112. The application software of server 112 includes a number of different modules capable of providing fitness monitoring services to athletes 100. In one embodiment of the present invention, these modules include a start module 200, and plan module 300, a schedule module 400, a track module 500, a support module 600, a library module 700, a forum module 800, a route module 1500, a coaching group module 1600, and an assessment workout module 1700. Each module supports one or more graphical user interfaces (GUIs) capable of being presented to athletes 100 at one or more portable fitness monitoring devices 102 and/or users at remote personal computers 114. Embodiments of the present invention may employ software modules such as, for example, those disclosed in commonly owned U.S. patent application Ser. No. 12/468,025, titled "Program Products, Methods, and Systems for Providing Fitness Monitoring Services," which is incorporated herein by reference in its entirety.

The server 112 may be, for example, a telecommunication server, a web server, or other similar types of database servers. In an embodiment, server 112 may have multiple processors and multiple shared or separate memory components such as, for example, one or more computing devices incorporated in a clustered computing environment or server farm. The computing process performed by the clustered computing environment, or server farm, can be carried out across multiple processors located at the same or different locations. In an embodiment, server 112 can be implemented on a single computing device.

As is known by those of skill in the art, a GUI may use a combination of technologies and devices to provide a platform that the athlete 100 or other user can interact with via the portable fitness monitoring device 102 or the personal computer 114. A GUI may offer, for example, graphical elements, visual indicators, and/or text to represent information and actions available to the athlete 100 or other user. Graphical elements may include, for example, windows, menus, radio buttons, check boxes, and/or icons. The athlete 100 or other user may use a physical input device, such as a mouse, track pad, and/or scroll ball to control the position of a cursor on their portable fitness monitoring device 102 or personal computer 114 screen. Alternatively, the athlete 100 or other user may use a touch screen, with or without a stylus, to interact directly with what is displayed (rather than indirectly via a cursor). Various touch screens such as, for example, resistive or capacitive touch screens, may be employed.

Those skilled in the art will appreciate that alternative or additional modules and sub-modules may be implemented within the server 112 in order to provide or extend the described or additional functionalities. For example, the software configuration of server 112 may include an operating system, which may be one of the commercially available operating systems such as, for example, Windows, UNIX, LINUX, Mac OSX, or AIX. The operating system may also have an associated application programming interface through which middleware and application programs may access the services of the operating system. In addition, a hypertext transport protocol (HTTP) server may run on top of the operating system. As is well known in the art, HTTP server may communicate data over the internet using HTTP.

As illustrated in many of the figures, the various software modules of the fitness monitoring service of the present invention may support GUIs through which an athlete 100 or other user can interact with the fitness monitoring service using the portable fitness monitoring device 102 and/or the personal computer 114. As will be appreciated by those of skill in the art, in one embodiment the GUIs may appear as web pages provided by the server 112 via a website that may be accessible to the athlete 100 or other user over the internet 110 using a web browser on their portable fitness monitoring device 102 or their personal computer 114. In other embodiments, the GUIs may be generated by a processor based only on information stored on the portable fitness monitoring device 102 or the personal computer 114, a CD-ROM, a memory card or other removable media, a mobile phone, or other computer readable media accessible locally. In embodiments of the present invention, athletes 100 or other users can, among other things, use data generated from past performances to gauge improvement, set goals for the future, share performance data with others, and/receive assistance in planning exercises at intensities appropriate for the athlete's 100 current fitness level and goals.

C. EXEMPLARY PRE-ACTIVITY DATA PROCESSING AND FEEDBACK ASPECTS

In some embodiments of the present invention, prior to engaging in a physical activity, a user (who may or may not be the athlete 100) may access a website provided by the server 112 from a remotely located personal computer 114.

The term "personal computer" 114 is used herein to refer to any type of computing device having one or more processors, a network connection, and display that is capable of displaying a website. Thus, a personal computer 114 may be, for example, a desktop or laptop computer. In an embodiment, the portable fitness monitoring device 102 itself may also serve as the personal computer 114—thus, for example, the personal computer may be a mobile phone, a personal digital assistant, a music file player (e.g. an MP3 player), or a tablet computer.

In order to access the features of embodiments of the present invention prior to engaging in a physical activity, a user stationed at the remote personal computer 114 may login to the server 112 via the internet 110. As is well known to those skilled in the art, the login process, which may be controlled by a login wizard run by start module 200, typically includes the entry by the remote user of a login ID and password or other authentication information to the server 112, which then authenticates the identity of the user by reference to a user database or the like. Embodiments of the fitness monitoring services of the present invention may be offered to a plurality of athletes 100 or other users forming a user community, may be restricted to users that have been issued login IDs and passwords for accessing the server 112, and/or may further be offered in exchange for a subscription fee.

Figure 9:
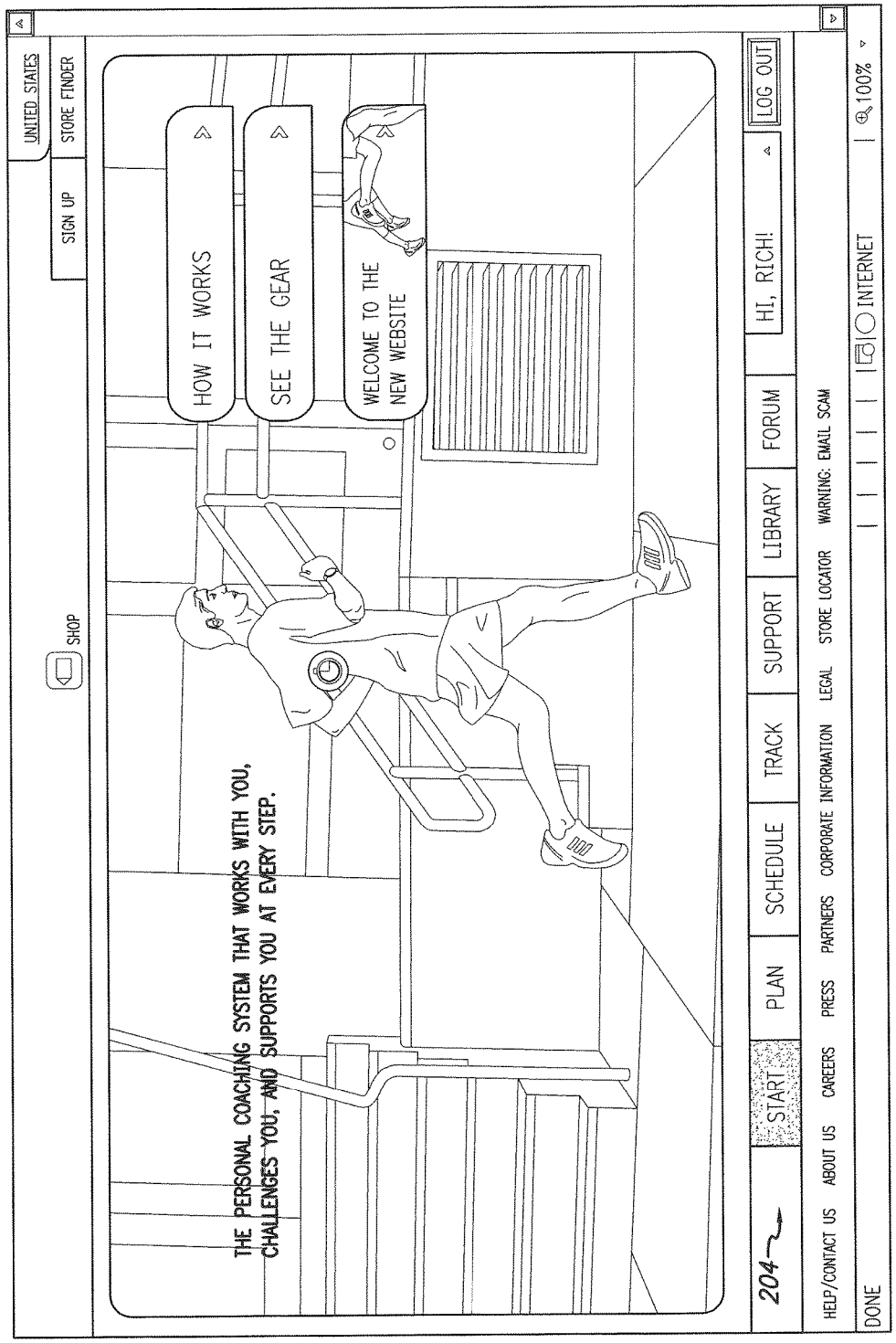
FIG. 9 is an exemplary graphical user interface (GUI) window according to an embodiment of the present invention.

Upon successful login, start module 200 may present a home page, as illustrated in FIG. 9. As shown in FIG. 9, a menu bar 204 may be present near one of the edges of a GUI window of the present invention. The menu bar 204 may include several icons or indicia corresponding to the start 200, plan 300, schedule 400, track 500, support 600, library 700, and forum 800 modules. In one embodiment, the menu bar 204 may be present on every GUI page presented to the user by the server 112. After logging in to the server 112, the user may be able to navigate to areas of the website supported by different modules by selecting their corresponding icons with, for example, a cursor or a touch screen interface. Additional icons corresponding to sub-modules or program wizards associated with a particular module may pop up or otherwise be displayed to the user if the user selects or hovers their cursor over a module icon.

In an embodiment, the user stationed at a remote personal computer 114 may alternatively choose to interact with the server 112 via a software widget or mobile device web application. As is known by those of skill in the art, a software widget is a software application including portable code intended for one or more different software platforms. The term "software widget" implies that either the application, user interface, or both, may be relatively simple and easy to use, as exemplified by a desk accessory or an applet.

In one embodiment, the software widget may be a desktop widget that is a specialized GUI widget intended to run on a personal computer 114 desktop. In another embodiment, the software widget may be a mobile widget that can operate on mobile devices (e.g. smart phones). The widget may present a simplified version of the user interfaces explained in further detail herein, and may provide alternative means for the user to log in to the server 112. The widget may allow the user to review summary information about their past performance, and may allow the user to view, for example, a calendar of upcoming workouts, as described in further detail below.

From the home page, the user may be able to navigate to different modules, sub-modules, or wizards by selecting their corresponding icons from the menu bar 204 with the cursor. In one embodiment, the user may be able to select an introductory sub-module.

The introductory sub-module may be capable of displaying an introductory page. The introductory page may contain general information about the fitness monitoring system of the present invention, including a brief description of the system, its intended users, and the potential benefits available to athletes 100 and other users.

For example, the introductory page may contain information about the planning, scheduling, and tracking capabilities of the fitness monitoring system. In one embodiment of the present invention, some aspects of the planning, scheduling, and tracking functions may be tied to a color-coded zone system such as, for example, the zone systems disclosed in commonly owned U.S. patent application Ser. No. 12/467,944, titled "Portable Fitness Monitoring Systems, and Applications Thereof," U.S. patent application Ser. No. 12/467,948, titled "Portable Fitness Monitoring Systems with Displays, and Applications Thereof," and U.S. patent application Ser. No. 12/468,025, titled "Program Products, Methods, and Systems for Providing Fitness Monitoring Services," each of which have previously been incorporated herein by reference in their entireties. In such an embodiment, the color-coded zone system may be based on zones of parameters including, but not limited to, heart rate, speed, pace, stride rate, calories, respiration rate, blood oxygen level, blood flow, hydration status, and/or body temperature. A graphical representation and a brief description of such a color-coded system may be provided on the introductory page and in personal settings. In one embodiment of the present invention, prior planning and scheduling a workout, the user may be given the option to select which performance parameter to base their zones on (e.g. heart rate, pace, speed, etc.).

In an embodiment of the present invention, the color of certain graphical information provided by the server 112 via the various GUIs presented may be dictated by detected or target performance information. Various modules of the fitness monitoring service of the present invention may be programmed with algorithms for establishing one or more performance parameter ranges or "zones." Each zone may be associated with a particular color. Zones may be defined, for example, as ranges of percentages of an athlete's 100 maximum speed or heart rate. Accordingly, each zone may be associated with a particular level of effort.

FIG. 10 is an exemplary illustration of zone definitions according to one embodiment of the present invention. An energy zone, ranging from 65% to 75% of an athlete's 100 maximum heart rate, is associated with the color blue. An endurance zone, ranging from 75% to 85% of an athlete's 100 maximum heart rate, is associated with the color green. A strength zone, ranging from 85% to 90% of an athlete's 100 maximum heart rate, is associated with the color yellow. Finally, a power zone, ranging from 90% to 95% of an athlete's 100 maximum heart rate, is associated with the color red. These ranges and color combinations are exemplary only; numerous other ranges and/or colors could be used.

FIG. 11 is an exemplary illustration of zone definitions according to another embodiment of the present invention. An energy zone, ranging from a 12 minute per mile to a 10 minute per mile pace, is associated with the color blue. An endurance zone, ranging from a 10 minute per mile to an 8 minute per mile pace, is associated with the color green. A strength zone, ranging from an 8 minute per mile to a 7 minute per mile pace, is associated with the color yellow.

Finally, a power zone, ranging from a 7 minute per mile to a 6 minute per mile pace, is associated with the color red. These ranges and color combinations are exemplary only; numerous other ranges and/or colors could be used. The zones may instead be based on other parameters such as, for example, speed.

In an embodiment, an additional zone (for example, a pink zone) may also be provided that overlaps the ranges of the blue, green, and yellow zones. The pink zone may primarily be used for setting intensity goals for beginners. In a further embodiment, the colors may change in character from relatively light or dim colors to relatively dark or intense colors as values associated with the zone colors increase from the lower to upper limits of the zone.

The zones may be assigned based on predetermined fitness goals. For example, in the embodiments of FIGS. 10 and 11, the energy zone (blue) may be associated with a heart rate or pace range, respectively, that allows an athlete 100 to build their aerobic base. The endurance zone (green) may be associated with a heart rate or pace range, respectively, that allows an athlete 100 to build cardiovascular strength and burn calories. The strength zone (yellow) may be associated with a heart rate or pace range, respectively that allows an athlete 100 to improve their aerobic threshold, endurance, and metabolism. The power zone (red) may be associated with a heart rate or pace range, respectively, that allows an athlete 100 to improve their anaerobic threshold, endurance, and metabolism.

For pre-activity planning purposes, the zones can be presented to the user as an indication of the difficulty of a particular workout. For monitoring and tracking purposes during and after the activity, as described in further detail below, the zones may be established for a particular athlete 100 based on, for example, a maximum heart rate or a maximum speed.

In particular, an athlete's 100 maximum heart rate may not change significantly with training, and it may be set by the athlete's 100 genetics. An athlete's 100 maximum heart rate can be provided to the fitness monitoring service of the present invention in a number of ways, as described in further detail below. In contrast, an athlete's 100 maximum speed may change significantly with additional training.

As indicated above, in embodiments of the present invention, the menu bar 204 may be present on every GUI page presented to the user by the application software of server 112. Accordingly, at any time, the user may be able to navigate to portions of the website supported by different modules, sub-modules, or wizards by selecting their corresponding icons from the menu bar 204 with, for example, the cursor or a touch screen interface. In one embodiment, the user may be able to select an icon corresponding to the plan module 300 from the menu bar 204.

Figure 12:
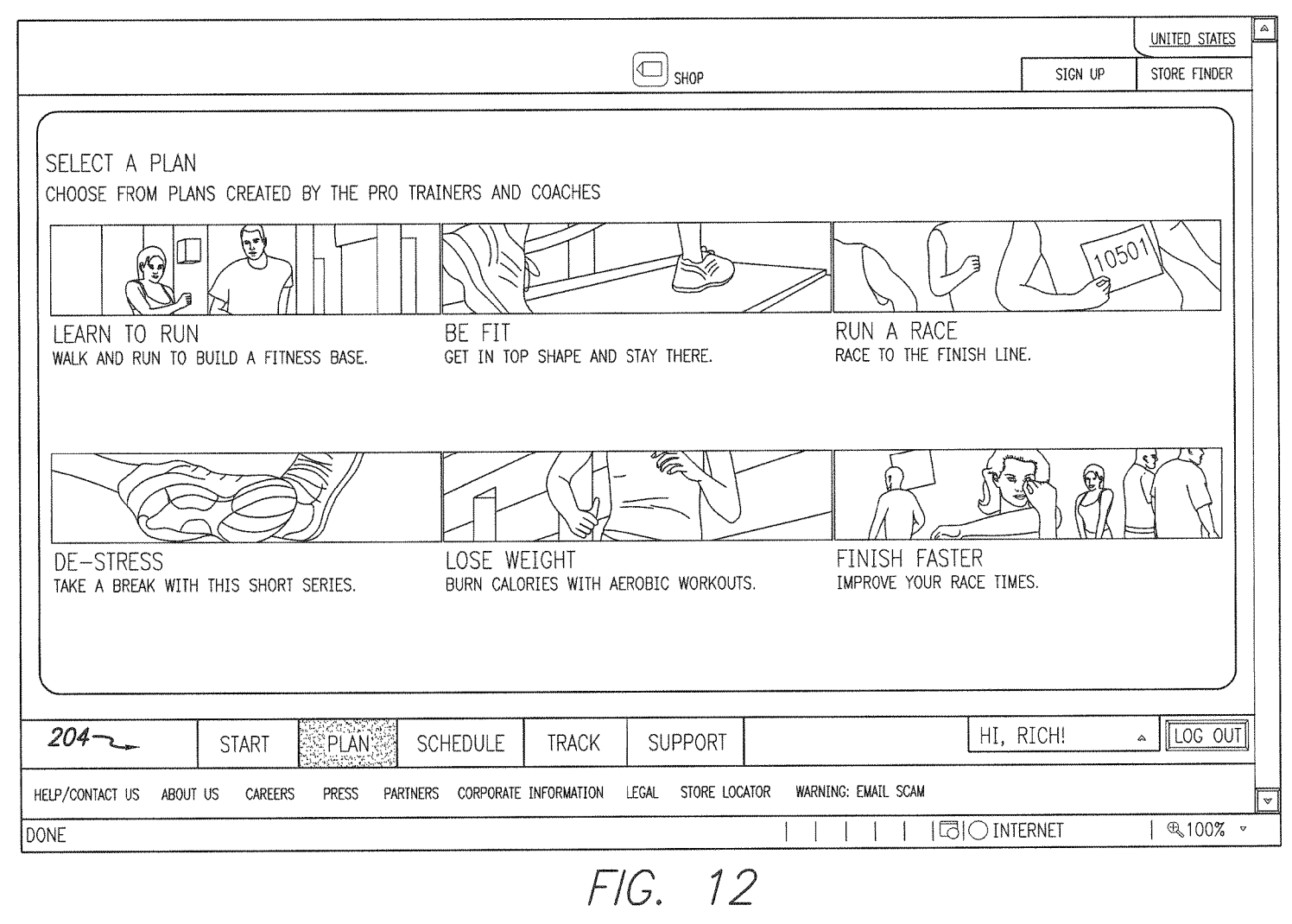

FIG. 12 is an exemplary GUI window that may be displayed by the plan module 300. From the main plan module page, the user (who may or may not be the athlete 100) may be able to select from one of a plurality of icons corresponding to training plans. Additional icons corresponding to training sub-plans may pop up or otherwise be displayed to the user if the user selects a training plan icon with the cursor or via a touch screen interface.

In one embodiment of the present invention, from the main plan page, the plan module 300 may enable the user to select training plan icons associated with various training plan sub-modules, such as, for example, a Learn to Run sub-module, a Be Fit sub-module, a Run a Race sub-module, a De-Stress sub-module, a Lose Weight sub-module, and a Finish Faster sub-module. Training plan sub-modules of embodiments of the present invention may include features such as, for example, those disclosed in commonly owned U.S. patent application Ser. No. 12/468,025, titled "Program Products, Methods, and Systems for Providing Fitness Monitoring Services," which has previously incorporated herein by reference in its entirety.

In an embodiment of the present invention, training plan icons may be associated with various training plan sub-modules that are sport specific. For example, training plan sub-modules designed to provide training plans to athletes 100 who desire to train for and/or maintain their conditioning for certain sports such as, for example, soccer (i.e. football), American football, tennis, inline skating, rugby, cycling, and/or basketball, may also be provided.

Each plan module 300 sub-module may be associated with a different training plan having a different intended athlete 100 audience and different goals. For example, in one embodiment of the invention, the Run a Race sub-module may provide a plurality of different plans depending on the distance of the race the athlete 100 is planning to participate in. Plans may be provided, for example, for 5K, 10K, ½ marathon, and full marathon races. An athlete 100 utilizing one of the Run a Race programs may be encouraged to, for example, conduct interval or other speed work training, take long runs and recovery runs, and generally build their endurance and aerobic capacity so that they are able to successfully complete their race.

FIG. 13 is an exemplary GUI window that may be displayed by the plan module 300 Run a Race sub-module. Each plan sub-module page may include a description of the plan, including its intended athletic users 100 and its goals. Each plan sub-module page may further include a level selector 314 and a plan preview 316. The particular information displayed by the plan preview 316 may depend on a level selected via the level selector 314.

Once a difficulty level for a prospective plan has been selected via level selector 314, the particular training plan sub-module provides the plan preview 316 for the plan. The plan preview 316 may include a description of what to expect from the plan, a description of the benefits of the plan, and/or a sample schedule. The plan description may make reference to the particular color-coded pace, speed, or heart rate zones that an athlete 100 may be prompted to exercise at as part of that plan.

After determining which plan best suits the athlete's 100 needs, the user may select an icon that enables plan module 300 to launch a plan personalization wizard. The plan personalization wizard may prompt the user to select a start date for their training plan, so that the plan may be built forward from that date. For users who select a race-oriented plan (such as those provided by the Run a Race sub-module), personalization wizard may prompt the user to select the day of the athlete's 100 race, so that the plan may be built backward from the race date. The plan personalization wizard may further prompt the user to give their plan a name. In one embodiment, the wizard may provide a default name. In this way, a user who wishes to schedule multiple training plans may be able to distinguish one plan from another by the plans' names.

In one embodiment, after the user finalizes their plan via the personalization wizard, schedule module 400 may populate a GUI calendar 402 with the user's plan (e.g. individual workouts of the plan). In addition, at any other time when the user 100 is logged in to the server 112, the user may be able to navigate to the GUI calendar 402 by selecting the icon corresponding to the schedule module 400 from the menu bar 204.

Figure 14:
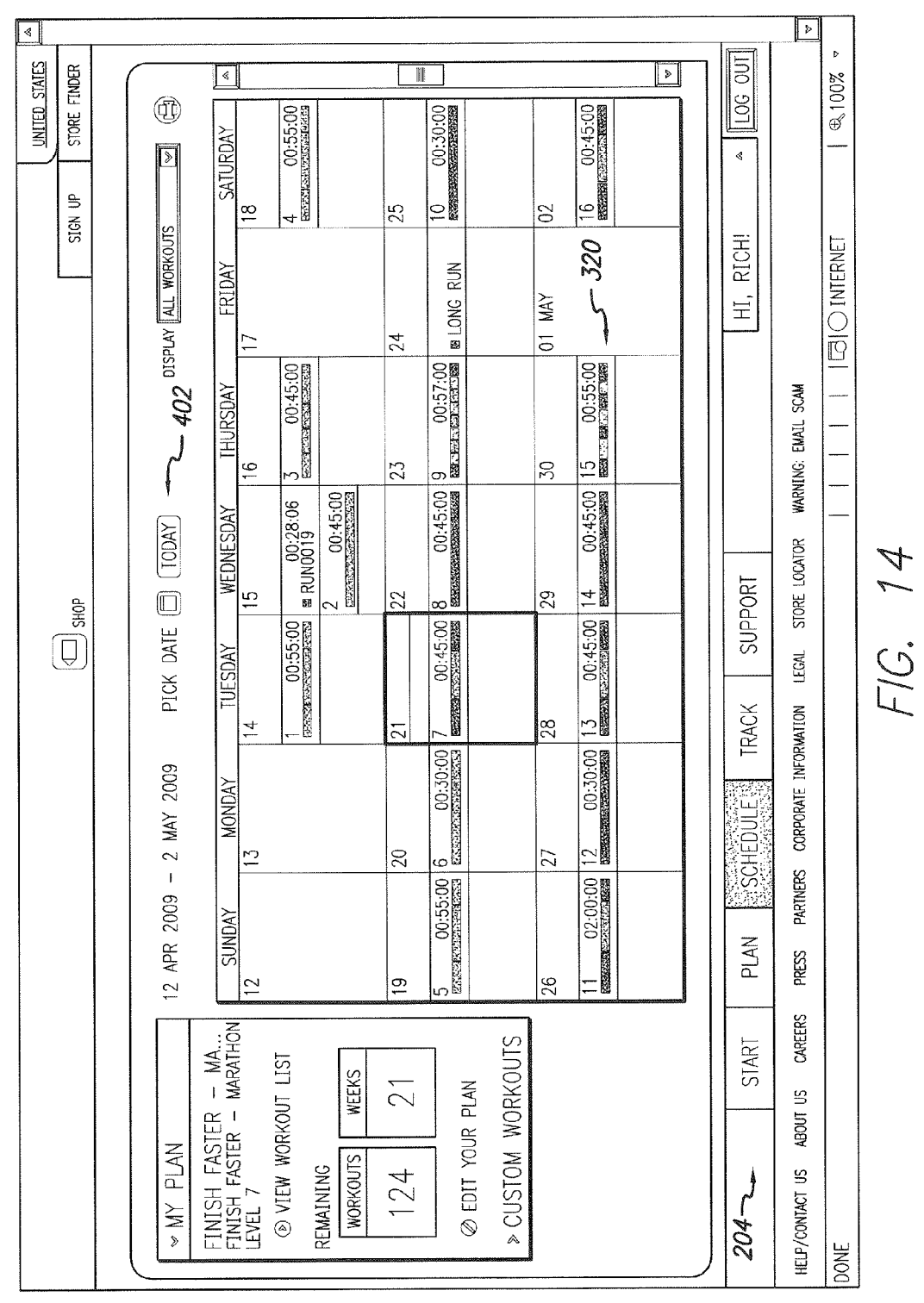

FIG. 14 is an exemplary GUI window according to an embodiment of the present invention containing the calendar 402 that may be displayed by the schedule module 400 for a user who has selected a Finish Faster level 7 marathon race program. From the calendar 402 page, the user may be able to view the individual workouts of their training plan populated throughout the calendar 402.

The individual workouts populated into the calendar 402 may be represented by a zone bar indicator 320. The zone bar indicator 320 may communicate several pieces of information. It may indicate the number of intervals to be performed in a workout comprised of training intervals. It may also indicate the relative intensities of each interval to be performed, based on, for example, a target heart rate, pace, or speed zone, as indicated by a color. The calendar 402 may also indicate the duration of each workout scheduled for each date. The GUI page containing the calendar 402 may also provide an indication of the number of workouts and/or number of weeks remaining for the current plan.

In one embodiment, the user may be able to access a workout list containing a listing of all workouts of their currently selected plan by selecting an appropriate icon with, for example, their cursor or a touch screen interface. The workout list is another way of presenting the workout information populated on to calendar 402.

In addition, a custom workout wizard may allow a user to add workouts to their calendar 402 regardless of whether or not an athlete 100 is currently participating in a scheduled plan program. If an athlete 100 is participating in a scheduled plan program, the custom workout feature may be used to supplement the plan with additional workouts, remove workouts, or edit workouts as the user desires.

Figure 15:
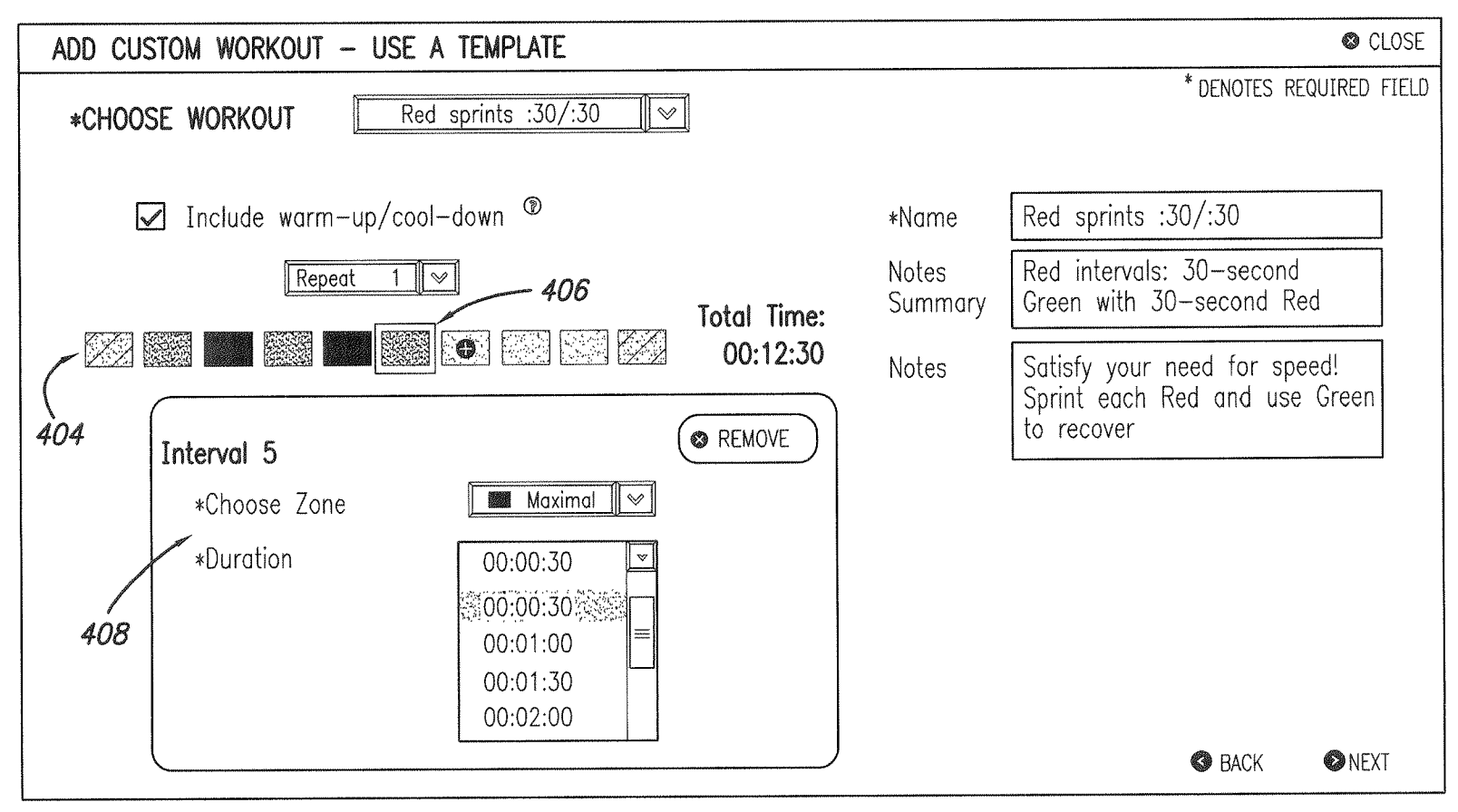

The custom workout wizard may allow a user to build a workout with a single zone, or a workout with a plurality of zone intervals. In an embodiment, as shown in FIG. 15, the custom workout wizard may present a GUI page that allows the user to build a custom workout one interval at a time in a graphical manner. The GUI page may include an interval builder bar 404 that in some ways resembles a zone bar indicator 320. After selecting an particular segment of the interval builder bar 404 with, for example, a cursor, the user may assign a zone intensity color and a interval duration to the segment using drop-down menus.

For example, in the embodiment of FIG. 15, the user has so far constructed an interval builder bar 404 that includes a series of 30 second red zone (dark grey shading) and green zone (black shading) intervals. Such a pattern would allow the athlete 100 to conduct 30 second red zone sprints. In addition, the interval builder bar 404 includes five minute blue zone intervals (cross-hatched shading) at the start and finish. These blue zone intervals may serve as warm up and cool down periods, and the user may enable them by checking an appropriate checkbox. By selecting a particular interval builder bar 404 segment, such as segment 406, the GUI page may display details about the particular segment in a interval details box 408. For example, interval details box 408 indicates that segment 406 is a 30 second red zone interval. The user could modify segment 406 by adjusting the zone and duration options in interval details box 408. For example, interval details box 408 indicates that segment 406 is a 30 second red zone interval. The user could modify segment 406 by adjusting the zone and duration options in interval details box 408.

In one embodiment, the zone interval times may be predetermined periods of time (e.g. 30 seconds, 1 minute, 5 minutes). In another embodiment, the user may be able to adjust or program the zone interval time periods.

In addition, the user may be able to name the custom workout and provide notes regarding its goal or purpose, and may save the custom workout for future use and population in calendar 402.

In one embodiment of the present invention, as outlined above in FIG. 8, the application software of server 112 may be configured to include a route module 1500. The route module 1500 may be capable of generating routes for the athlete 100 to follow during a fitness activity, storing routes within a route database for subsequent access, and downloading the routes to portable fitness monitoring devices 102. The route module 1500 may also include additional features, such as those disclosed in commonly owned U.S. patent application Ser. No. 10/759,289, titled "Location-aware fitness training device, methods, and program products that support real-time interactive communication and automated route generation," which has previously been incorporated herein by reference in its entirety.

In an embodiment, the route module 1500 may include a route wizard that is capable of guiding a user (who may or may not be the athlete 100) through a step-by-step process for generating routes having desired parameters and attributes. Route module 1500 may have access to a locally or remotely stored map database that stores street and/or trail information in association with at least latitude and longitude information, and possibly elevation information. Thus, given at least one terminal point (e.g., a starting point), route module 1500 may be able to construct one or more routes having a desired length, elevation profile, and other parameters and attributes. In one embodiment, the user may be able to build a new route from scratch or search for an existing route within a route database.

If the user opts to build a new route from scratch, the user may first be prompted to designate an approximate starting point of the route by, for example, entering a street address, ZIP code, or a particular point-of-interest. Next, the user may be prompted to enter a desired overall length of the route, specified either by distance or by time, if these parameters are not already specified for a particular workout of a training plan. If time is utilized to specify the length of the route, a desired or historical average pace may be necessary so that a route distance can be computed. In addition, the user may also be prompted to enter optional route attributes such as, for example, a desired elevation profile of the route or a desired pattern of the route (e.g. linear, loop, etc.). Once the user has entered all required parameters and any optional route attributes, the route module 1500 may build one or more routes conforming as closely as possible to the route parameters and route attributes entered. The presentation of such routes by a route wizard is described in further detail below.

If the user opts to search for an existing route within a route database, the user may be permitted to specify a location of the route by, for example, city name, ZIP code, or point-of-interest. The user may further be prompted to enter optional route attributes such as, for example, a desired elevation profile of the route, a desired pattern of the route, desired safety characterization of the route, and/or a desired route difficulty rating. In one embodiment, the route difficulty rating may be assigned to the route based on one or more of route length, elevation changes over the route, and altitude of the route.

Figure 16:
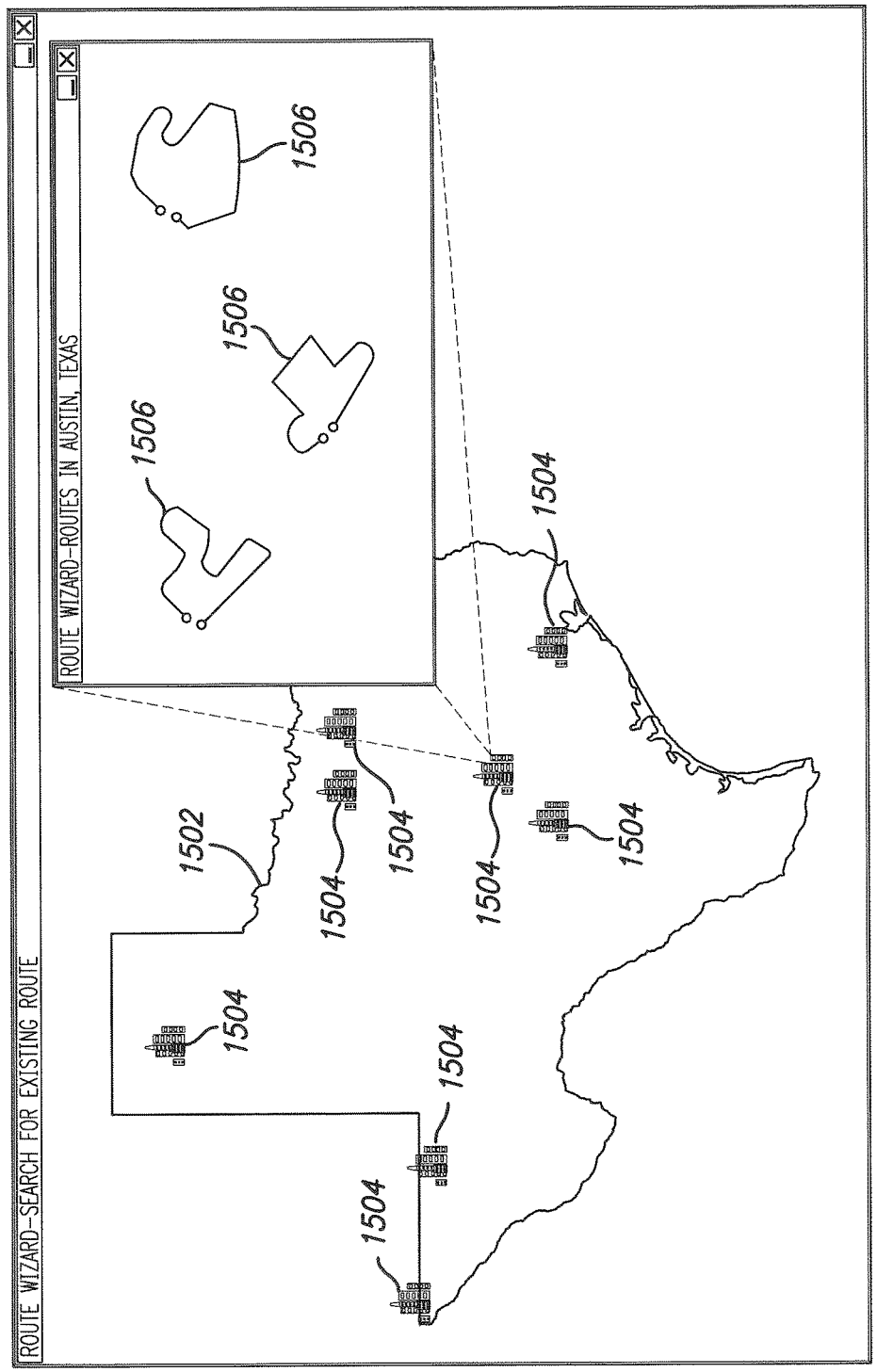
FIG. 16 is an exemplary GUI window according to an embodiment of the present invention.

In an embodiment, as shown in FIG. 16, the route wizard may present a navigable geographical map populated with graphical indications of locations for which preexisting routes are stored within the route database. In the depicted embodiment, the map includes a graphical representation 1502 of a geographical area, for example, a political, cultural, or regional boundary. Within the geographical representation 1502, the route wizard may present a number of indicia 1504 identifying geographic locations of one or more preexisting routes for which route database stores route data. In response to the user hovering over one of indicia 1504 utilizing, for example, a cursor, the route wizard may display in a pop-up window route maps 1506 of the routes in the geographic location corresponding to the selected indicia 1504. If the user visually identifies one or more routes of interest at a particular geographical location through visual inspection of indicia 1504 and/or the route maps 1506 displayed within windows, the user may select that geographical location by clicking on the associated indicia 1504. In this manner, a GUI window and its associated functionality provide the user with a graphical and intuitive way of viewing and selecting route locations of interest.

Once a particular route is chosen by the user, the route may be associated with one or more workouts of the training plan scheduled on the calendar. In one embodiment, the route may be transformed into a sequence of turn-by-turn instructions and transmitted to the portable fitness monitoring device 102 prior to the activity. In an embodiment, the route may be transmitted to the portable fitness monitoring device 102 as part of—or simultaneously with—a workout routine.

As indicated above, the menu bar 204 may include an icon corresponding to the support module 600 of the application software.

The support module 600 may include help and settings sub-modules. The help sub-module may present GUI pages that contain general information about the fitness monitoring system of the present invention, including a brief description of the system, its intended users, and the potential benefits available to those users. The help sub-module may provide a description of the various functions of the interactive website supported by the software and the underlying modules, sub-modules, and wizards.

The settings sub-module of the support software module 600 may be capable of displaying GUI windows for collecting, storing, and/or reviewing personal settings, workout settings, device settings, and/or privacy settings.

Figure 17:
FIG. 17 is an exemplary GUI window according to an embodiment of the present invention.

FIG. 17 is an exemplary GUI window that may be generated by the settings sub-module for collecting personal settings information. Personal settings information may include, for example, name, address, email address, password, gender, birth date, and/or address information. This information may be used to associate a specific athlete 100 with a particular user account. In an embodiment, some of this information may be used to tailor aspects of the portable fitness monitoring system to the athlete 100, or to provide messages, product offers, and/or other items of interest to the athlete 100.

Figure 18:
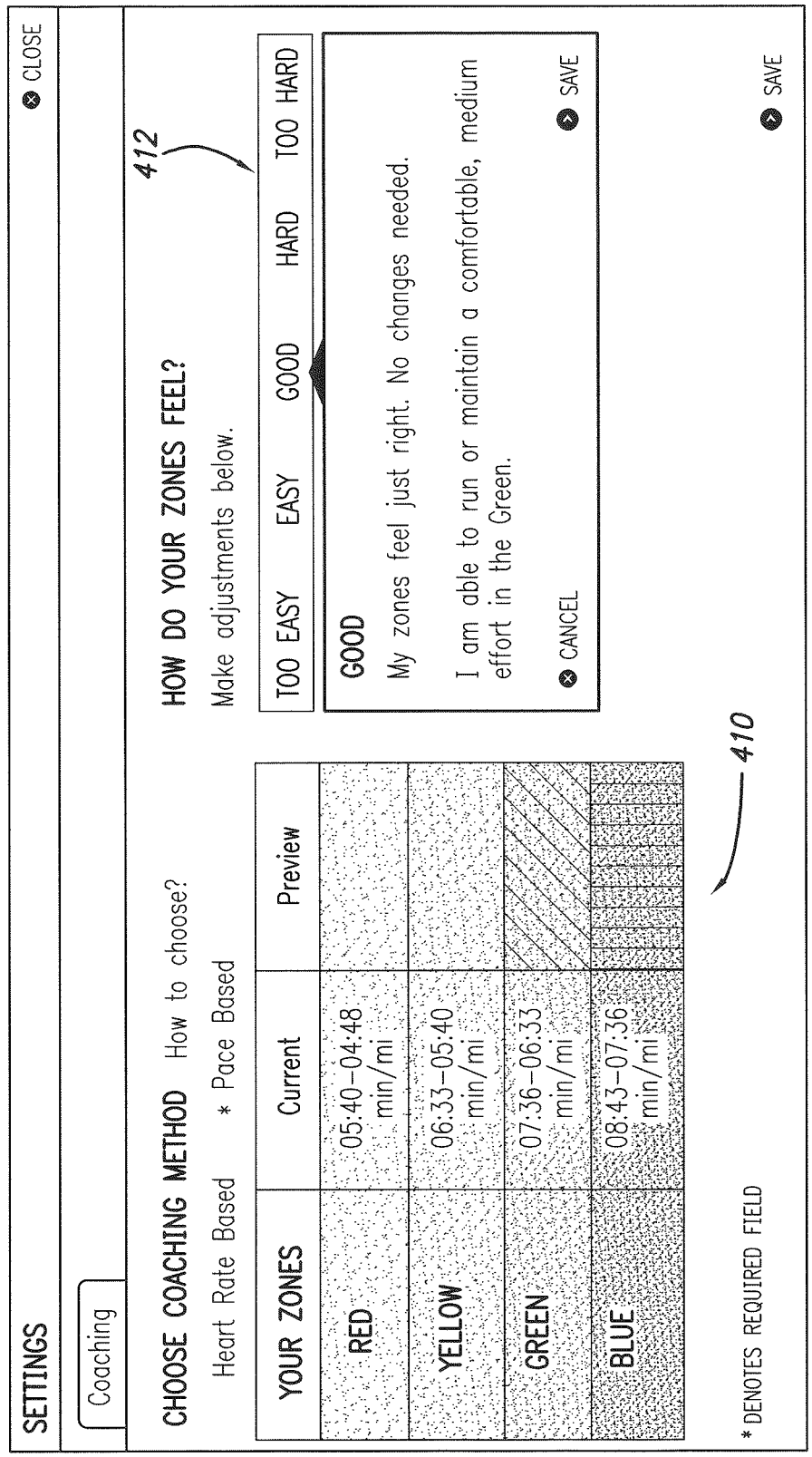
FIG. 18 is an exemplary GUI window according to an embodiment of the present invention.

FIG. 18 is an exemplary GUI window that may be displayed by the settings sub-module for collecting coaching settings information. Coaching settings may include an option to select, for example, heart rate- or pace-based feedback and coaching. The coaching settings display may include a chart 410 detailing the athlete's 100 current zone ranges for a given parameter.

In addition, a user may access the coaching settings feature to adjust their zone ranges if they feel that the current zone ranges are not ideal. For example, in one embodiment, a user could manually enter new zone ranges. In another embodiment, as illustrated in FIG. 18, the GUI of the coaching settings page may ask the athlete 100 how they feel. The athlete 100 may indicate, for example via selector bar 412, that the zones feel too easy, easy, good, hard, or too hard. The coaching settings page may provide guidance to the athlete 100 to help the athlete 100 properly answer the question. For example, the coaching settings page may indicate that the "too hard" option should be selected if the athlete has to sprint to reach the green zone. In response to the athlete's selection, the system of the present invention may adjust the athlete's 100 performance zone ranges appropriately. In an embodiment, the zone adjustments may be made in response to a series of questions that seek to determine an appropriate intensity level for the athlete 100.

The settings sub module may also allow an athlete 100 to enter workout settings information. Workout settings information may include preferences such as preferred distance units (miles vs. kilometers), height units (feet and inches vs. meters and centimeters), weight units (pounds vs. kilograms), time format (12 hour clock vs. 24 hour clock), and a preferred week start date (e.g. Sunday or Monday). Workout settings information may also include fitness profile information such as the athlete's 100 weight, height, gender, and maximum heart rate (if known). In one embodiment, the athlete 100 may be periodically prompted by the system to update their fitness profile information.

FIG. 19 is an exemplary GUI window that may be displayed by the settings sub-module for collecting device settings information. Device settings information may include settings for any peripheral devices the athlete 100 has and is using in conjunction with the system of the present invention. These devices may include, for example, the portable fitness monitoring device 102 which may take the form of, for example, a mobile phone, a dedicated portable fitness monitoring device, a non-dedicated portable fitness monitoring device, a sports mode-enabled MP3 player, a sports-enabled dongle, a sports watch, a display device, and sensors (e.g. pedometers or heart rate sensors). The user may indicate which, if any, devices the athlete 100 may use during workouts.

For example, via the settings page, the user may be able to adjust audio feedback options provided by the portable fitness monitoring device 102 during a workout, as described in further detail below. In one embodiment, the user may select audio feedback with different types or styles of voices such as, for example, voices of different gendered speakers, voices with different accents, voices in different languages, voices from celebrities or fictional characters, and voices of different tones (e.g. supportive, calming, energizing, or stern). In another embodiment, the user may select specific performance parameter measurements to be recited via audio feedback during the workout. For example, a user may choose to have elapsed time, calories burned, and distance traveled so far announced to the athlete 100 at regular intervals, on demand, or at predetermined times/locations throughout the workout.

D. EXEMPLARY DATA PROCESSING AND FEEDBACK ASPECTS DURING AN ACTIVITY

In one embodiment of the system of the present invention, an athlete 100 may interact with a portable fitness monitoring device 102, such as those illustrated in FIGS. 1-4, just prior to and/or during a fitness activity.

Figure 20:
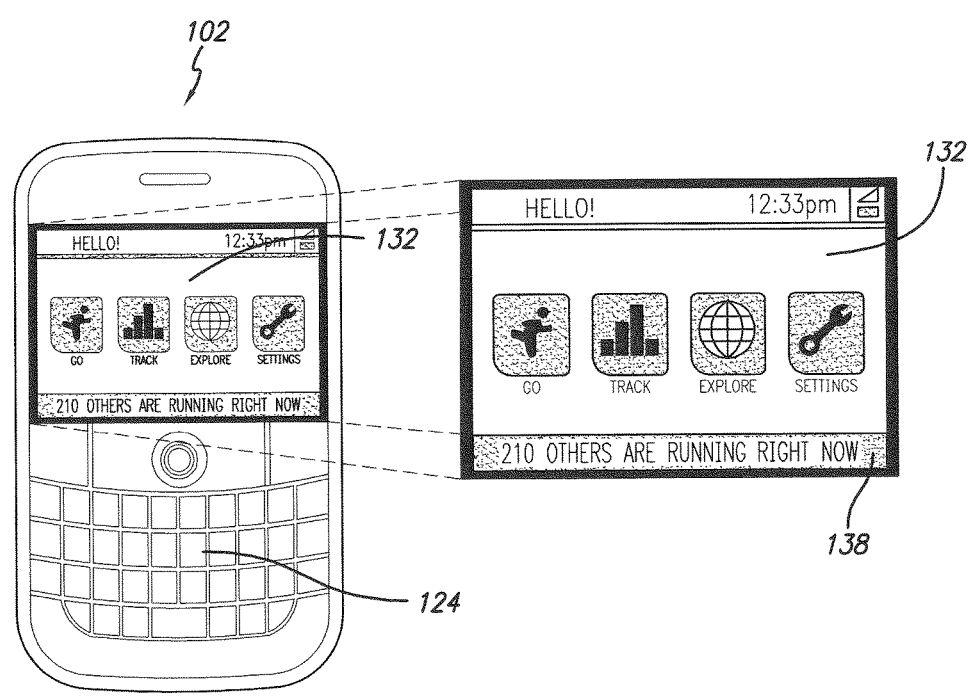
FIG. 20 is an illustration of a portable fitness monitoring device according to an embodiment of the present invention.

FIG. 20 is an illustration of a portable fitness monitoring device 102 in the form of a mobile phone. In an embodiment of the present invention, the portable fitness monitoring device 102 in the form of a mobile phone may include at least a processor 120, a memory 122, user input controls 124, a positioning system receiver 126, a wireless wide area network (WWAN) transceiver 128, a visual display 132, and an audio unit 134, such as those illustrated in FIG. 3. In one embodiment, the portable fitness monitoring device 102 in the form of a mobile phone may include each of the components indicated in FIG. 3. A visual display 132 in the form of a LCD screen, and user input controls 124 in the form of a physical keyboard and a scroll ball, are illustrated in FIG. 20. An enlarged version of the LCD screen display 132 has been illustrated on the right side of FIG. 20. In an embodiment, a content banner 138 may be present at an edge of the display 132. The content banner may provide, for example, advertisements, rewards, weather information, achievements, or statistics of other information about users of the fitness monitoring service.

Figure 21:
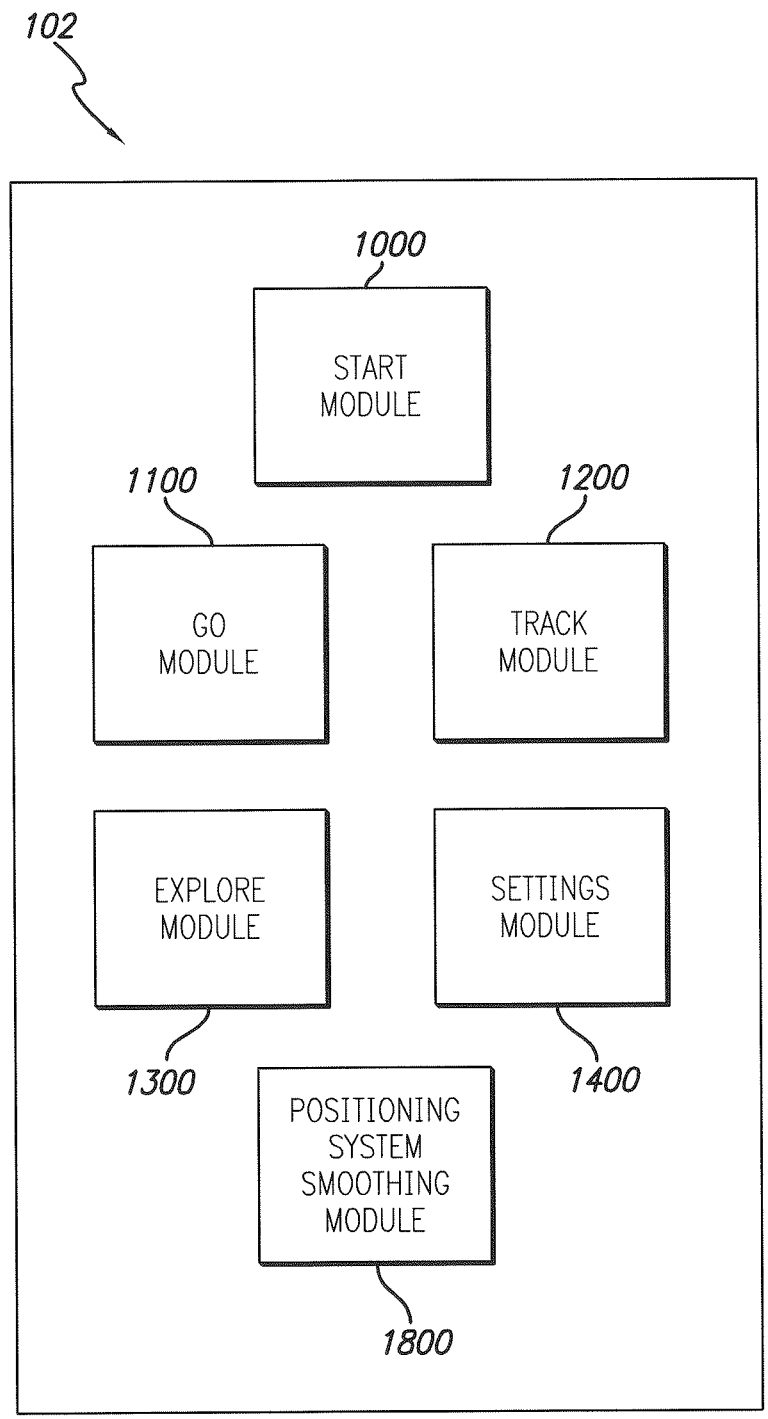
FIG. 21 is a block diagram of an exemplary software configuration of a portable fitness monitoring device according to an embodiment of the present invention.

FIG. 21 is a diagram of an exemplary software configuration of the application software of the portable fitness monitoring device 102. As indicated above, the memory 122 of the portable fitness monitoring device 102 may be adapted to store application programs used to implement aspects of the functionality of the portable fitness monitoring system described herein. Thus, the application software may be stored, for example, in the memory 122 of the portable fitness monitoring device. Alternatively, those of skill in the art will understand that all or part of the software may be stored on the server 112 and accessed over the network 110 and run remotely as a mobile web application.

This application software includes a number of different software modules capable of providing fitness monitoring services to athletes 100 using portable fitness monitoring devices 102. In one embodiment of the present invention, these modules include a start module 1000, a go module 1100, a track module 1200, an explore module 1300, a settings module 1400, and a positioning system smoothing sub module 1800. Each module may support one or more GUIs capable of being presented to an athlete 100 using the portable fitness monitoring device 102. Embodiments of the present invention may employ additional portable fitness monitoring device 102 software features such as, for example, those disclosed in commonly owned U.S. patent application Ser. No. 11/892,023, titled "Sports Electronic Training System, and Applications Thereof," which has previously been incorporated herein by reference in its entirety.

As described above with respect to display via the personal computer 114, a GUI may offer, for example, graphical elements, visual indicators, and/or text to represent information and actions available to the athlete 100. The athlete 100 may use a physical input device, such as keyboard or scroll ball to interact with the GUI of the portable fitness monitoring device 102. Alternatively, the athlete 100 may use a touch screen to interact directly with what is displayed. Various touch screens such as, for example, resistive or capacitive touch screens, may be employed.

Those skilled in the art will appreciate that alternative or additional software modules and sub-modules may be implemented in order to provide or extend the described or additional functionalities to the athlete 100 using the portable fitness monitoring device 102. For example, the software configuration of software stored on a portable fitness monitoring device 102 may include a portable device operating system, which may be one of the commercially available mobile phone operating systems such as, for example, BlackBerry OS, iPhone OS, Windows Mobile, Symbian, LINUX, WebOS, or Android. The portable device operating system may also have an associated application programming interface through which middleware and application programs may access the services of the operating system.

The various modules of the fitness monitoring service of the present invention may support GUIs through which an athlete 100 can interact with the fitness monitoring service using the portable fitness monitoring device 102 just prior to and/or during an activity. As will be appreciated by those of skill in the art, in one embodiment the GUIs may be supported by a mobile device web application being run on the portable fitness monitoring device 102. In another embodiment, the GUIs may appear as web pages provided by the server 112 via a website that may be accessible to the user over the Internet 110 using a web browser on their portable fitness monitoring device 102.

In order to access the features of embodiments of the present invention just prior to or during a physical activity, the athlete 100 using the portable fitness monitoring device 102 may power on their portable fitness monitoring device 102 if it is not already in a powered up state. In some embodiments, it may be necessary for the athlete 100 to manipulate user input controls 124 to enter a portable fitness monitoring mode to access the application software.

The first time the fitness monitoring application is launched, the start module 1000 may prompt the athlete 100 to select a preferred language. Next, or immediately upon subsequent launches of the application, the start module 1000 may prompt the athlete 100 to enter a password to proceed. The first time the application is launched, the start module 1000 may prompt the athlete 100 to select a password.

Upon entering the correct password, a GUI supported by the start module 1000 may ask the athlete 100 if they would like to link their portable fitness monitoring device 102 to a web account previously set up via the server 112 or if they would like to proceed as an un-linked guest.

If the athlete 100 indicates via activation of the user input controls 124 that the athlete 100 would like to link to a web account, the start module 1000 may present a GUI login wizard wherein the athlete 100 is able to log into and link to their web account. Upon linking to the web account, settings previously established using the personal computer 114 and the server 112 via the support module 600 may be transferred to or synced with the portable fitness monitoring device 102. Such settings may include, for example: workout settings information such as preferred distance units (miles vs. kilometers), height units (feet and inches vs. meters and centimeters), weight units (pounds vs. kilograms), time format (12 hour clock vs. 24 hour clock), and a preferred week start date (e.g. Sunday or Monday); fitness profile information such as the user's weight, height, and maximum heart rate (if known); heart rate, pace, or other custom workout interval setting information; audio feedback option information; and/or performance parameter feedback option information.

If the athlete 100 indicates via activation of the user input controls 124 that the athlete 100 does not have or does not want to link to a web account, the start module 1000 may present a login wizard where in the athlete 100 is able to enter information such as, for example, preferred unit preferences, personal information such as the athlete's 100 age, height, weight, and sex, and/or the athlete's 100 desired voice training options. This information may be necessary for conducting an "assessment workout" for a guest athlete 100, as described in further detail below.

Figures 22A, 22B:
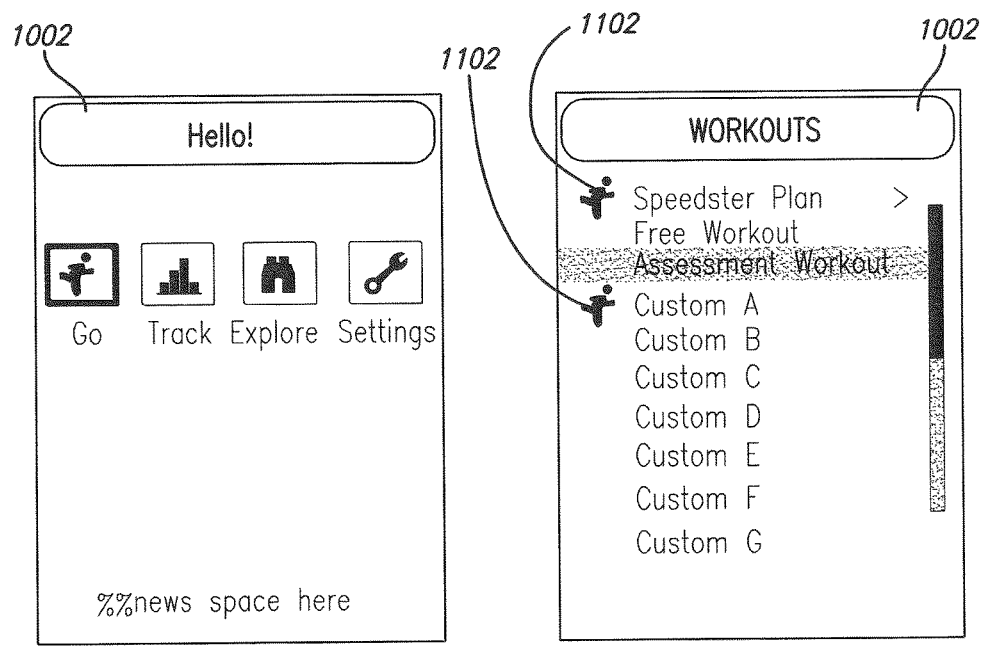
FIGS. 22A and 22B are exemplary GUI windows according to an embodiment of the present invention.

After the athlete 100 chooses to link to a web account or to continue as a guest, the start module 1000 may present a home page GUI, as illustrated in FIG. 22A. During subsequent launches of the software application, the home page may be presented to the athlete 100 immediately upon launch. As shown in FIG. 22A, a header 1002 may be present near one of the edges of a GUI window of the present invention. In one embodiment, the header 1002 may be present on every GUI page presented to the athlete 100 by software accessible by the portable fitness monitoring device 102.

The home page may also include several icons or indicia corresponding to the go 1100, track 1200, explore 1300, and settings 1400 modules. In one embodiment, the header 1002 may also provide a drop-down list including icons or indicia corresponding to the go 1100, track 1200, explore 1300, and settings 1400 modules. After launching the application software, the athlete 100 may cause different GUI pages to be provided by different modules by selecting their corresponding icons using user input controls 124. Additional icons corresponding to sub-modules or program wizards associated with a particular module may pop up or otherwise be displayed to the athlete 100 if the athlete 100 selects or hovers over a module icon with a cursor.

The settings module 1400 may offer functionalities similar to those described above with respect to the support module 600 of the application software of the server 112.

The go module 1100 may include a workout selection sub-module and a workout recording sub-module. In one embodiment, when the athlete 100 selects the icon corresponding to the go module 1100 on the home page, the go module initiates the workout selection sub-module.

FIG. 22B is an exemplary GUI window that may be provided by the workout selection sub-module. This GUI window may display plan workouts and custom workouts available to the athlete 100, as well as a free workout option and an assessment workout option, which are described in further detail below. In one embodiment, some indication will be given to the athlete 100 that they are scheduled to perform one or more of the listed plan or custom workouts on a given day. For example, as shown in FIG. 22B, indicators 1102 may appear by certain plan or custom workouts to indicate that the athlete 100 is scheduled to perform that plan or custom workout today.

As previously described, a user (who may or may not be the athlete 100) stationed at a remotely located personal computer 114 may use a website to plan and schedule a prospective physical activity. As illustrated in FIGS. 12-16, the user may utilize the plan module 300 and schedule module 400 to plan and schedule one or more prospective physical activities. For example, the user may select a training plan comprised of individual workouts, which may be saved and scheduled on a calendar 402 on the server 112. The user may also create, save, and optionally schedule custom workouts on the server 112. Alternatively, an athlete-user 100 may plan and schedule planned workouts and/or create, save, and schedule custom workouts by accessing the website directly from their portable fitness monitoring device 102. In one embodiment, the version of the accessible from the athlete's portable fitness monitoring device may be simplified or otherwise modified to optimize it for display on a relatively small screen.

In an embodiment, upon initiation of the workout selection sub-module via the portable fitness monitoring device 102, the list of available plan workouts and custom workouts may be updated by syncing to training plan, plan workout, and custom workout data available on the server 112. In other words, the portable fitness monitoring device 102 and the server 112 may communicate training plan, plan workout, and custom workout data via the network 110, for example, using the WWAN transceiver 128 of the portable fitness monitoring device 102. In one embodiment, plan workout and custom workout data, such as plan or custom workout routines, may be stored in the memory 122 of the portable fitness monitoring device 102.

Figure 23:
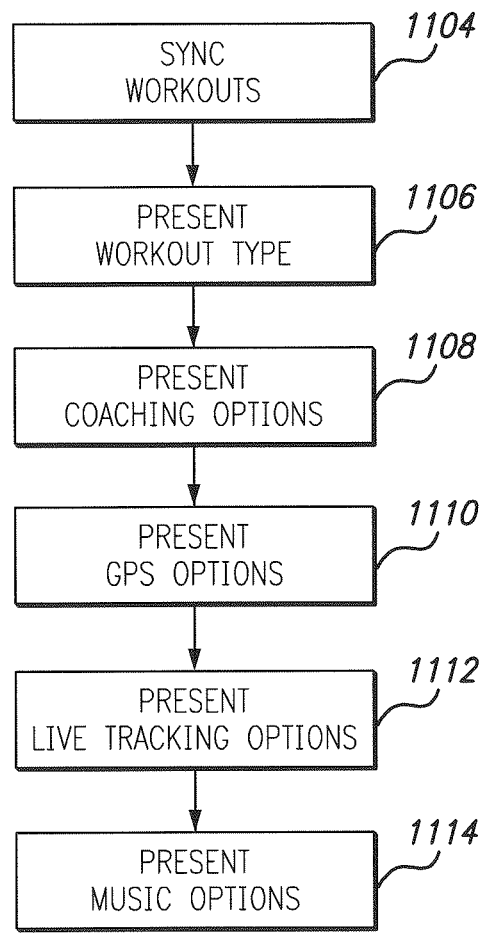
FIG. 23 is a flow chart outlining actions capable of being initiated by software according to an embodiment of the present invention.

FIG. 23 illustrates a sequences of actions that the workout selection sub-module may initiate after an icon corresponding to the go module 1100 is selected from the home page, according to one embodiment of the present invention. First, at step 1104, the available plans and custom workout routines may be updated by syncing to server 112. Next, at step 1106, the various workout routine types (e.g. plan workouts, custom workouts, a free workout, and an assessment workout) may be presented to the athlete 100 via the display 132 of the portable fitness monitoring device 102. The athlete 100 may then select one of the workout types using the user input controls 124. Finally, at steps 1108-1114, the athlete 100 may be prompted to chose their desired settings for a variety of different options including coaching options, satellite positioning system options, live tracking options, and/or music options, which are described in further detail below.

Figure 24A:
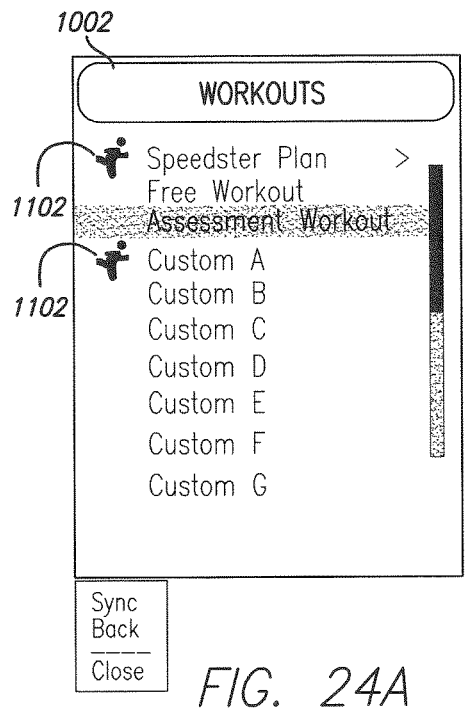
FIGS. 24A-24D are exemplary GUI windows according to an embodiment of the present invention.

FIGS. 24A-24D are exemplary GUI windows that may be displayed by the workout selection sub-module 1110 when the athlete selects a particular training plan. In FIG. 24A, the athlete 100 has highlighted and may select the "Speedster Plan" training plan using the user input controls 124 of the portable fitness monitoring device 102. Prior to the activity and prior to any syncing, the Speedster Plan may have been created and scheduled by a user using the server plan module 300 and the server schedule module 400 via a remote computer 114, as described above.

Figure 24B:
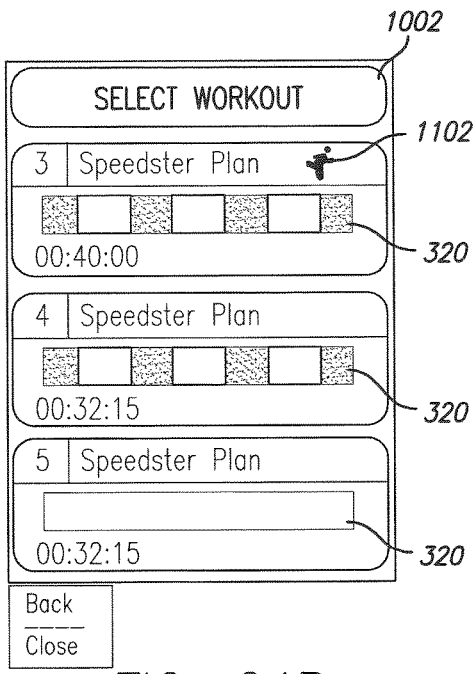

FIG. 24B is an exemplary GUI window that may be displayed by the workout selection sub-module 1110 after the athlete 100 selects the Speedster Plan. FIG. 24B lists several individual workout routines in the Speedster Plan. In an embodiment, only individual workouts scheduled for the present day may be listed. In another embodiment, past and/or future individual workouts may also be listed. In some embodiments, some indication will be given to the athlete 100 that they are to perform one or more of the listed plan or custom workouts today. For example, as shown in FIG. 24B, an indicator 1102 may appear next to a particular plan workout.

Figure 24C:
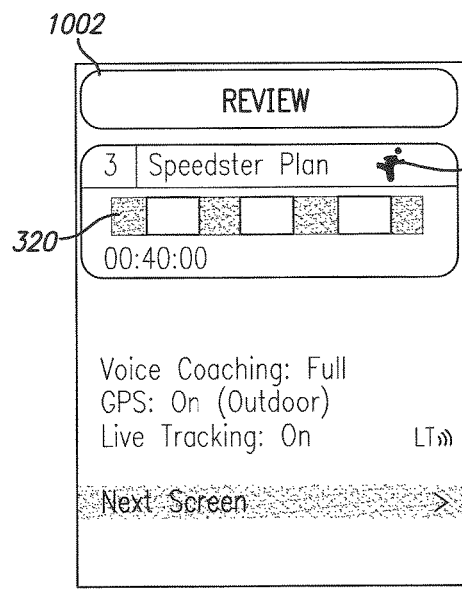

FIG. 24C is an exemplary GUI window that may be displayed by the workout selection sub-module after the athlete 100 selects a particular individual workout routine from the Speedster Plan. As shown in FIGS. 24B and 24C, each individual workout routine may be represented by a zone bar indicator 320, similar to that discussed above with respect to the server schedule module 400. The zone bar indicator 320 may communicate several pieces of information. It may indicate the number of intervals to be performed in a workout routine comprised of training intervals. It may also indicate the relative intensities of each interval to be performed, based on, for example, a target pace, speed, or heart rate zone, as indicated by a color. The GUI window may also indicate the duration the individual workout routine. Specifically, as can be seen in FIG. 24C, the selected workout routine consists of alternating blue zone and yellow zone intervals and is 40 minutes in length.

The exemplary GUI window shown in FIG. 24C may also include buttons, switches, drop-down menus, or other GUI elements for selecting voice coaching, satellite positioning system, and live tracking options.

Voice coaching generally refers to verbal instructions, feedback, or encouragement provide audibly to the athlete 100 during the activity, as described in further detail below. A workout selection sub-module may allow the athlete 100 to determine the level of voice coaching they would like to receive—if any. For example, in one embodiment, the athlete 100 may select between no coaching, passive coaching, or active coaching.

"No coaching" may refer to a situation where voice coaching is entirely absent or silenced during the activity.

"Passive coaching" may refer to a situation where the athlete 100 receives voice coaching only at the beginning of a new training interval. For example, an athlete 100 who is to begin a green zone training interval may receive coaching that states "increase your intensity to reach the green zone." If the training plan workout calls for the athlete 100 to begin a yellow zone interval after the green zone interval, at the beginning of the yellow zone interval athlete 100 may receive coaching that states "You have completed a green zone interval. Increase your intensity to enter the yellow zone."

"Active coaching" may refer to a situation where in addition to (or instead of) receiving voice coaching at the beginning of a new training interval, the athlete 100 receives reactive voice coaching throughout the interval. Specifically, the voice coaching may be responsive to performance information detected by sensors 104 of the portable fitness monitoring device 102. Thus, for example, feedback may be based on information detected by a heart rate monitor for a workout routine comprised of heart rate-based zones, or feedback may be based on information detected by a positioning system receiver 126 used to calculate speed or pace for a workout routine comprised of speed-based or pace-based zones. For example, if the athlete 100 should be in the middle of their first green zone interval but is only maintaining a blue zone intensity, the portable fitness monitoring device 102 may announce "your intensity is only at a blue zone level, increase your intensity to enter the green zone."

Workout selection sub-module may also allow the athlete 100 to determine the whether the positioning system receiver 126, such as a GPS receiver, should be enabled or disabled. In one embodiment, the portable fitness monitoring device 102 includes a GPS receiver that may be used to determine that athlete's 100 location, distance traveled, speed, and pace at various locations as the athlete 100 traverses a route. In other embodiments, a GPS receiver may not be present. Even if a GPS receiver is present, the athlete 100 may chose to disable it because, for example, the athlete 100 intends to workout indoors, workout on stationary equipment, or because the portable fitness device 102 is low on power. In an embodiment, the athlete 100 may also be able to enable or disable other sensors such as heart rate monitors or accelerometer-based sensors.

Workout selection sub-module may further allow the athlete 100 to determine whether live tracking should be enabled or disabled. "Live tracking" refers to the ability of a remote user other than the athlete 100 to track the athlete's 100 location in real time during the activity. As explained in further detail elsewhere, in an embodiment, the portable fitness monitoring device 102 may be able to wirelessly communicate location-based information to the server 112 via the network 110 in real-time via the WWAN 128 or WPAN 130 transceiver. Thus, users with access to this data on the server 112 (either stationed at a remote computer 114 or carrying a portable fitness monitoring device 102) may be able to view one or more athlete's 100 locations, for example, superimposed on a map. Some athlete's 100 may chose to disable live tracking, for example, because of privacy concerns.

Figure 24D:
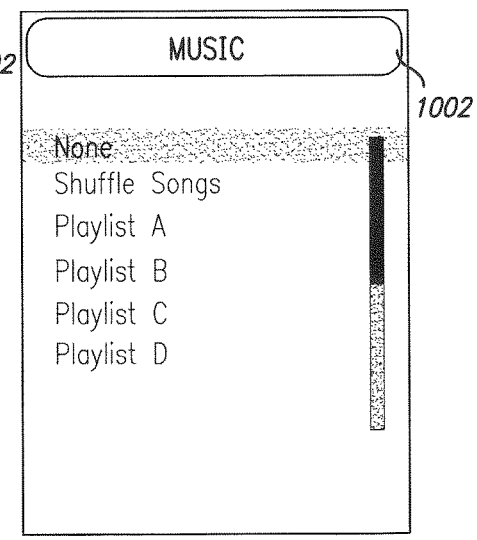
Figure 25A:
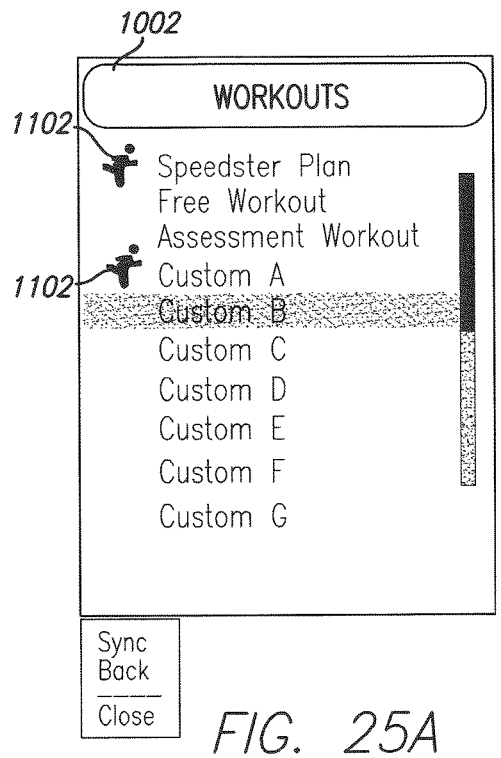
FIGS. 25A-25D are exemplary GUI windows according to an embodiment of the present invention.
Figure 25B:
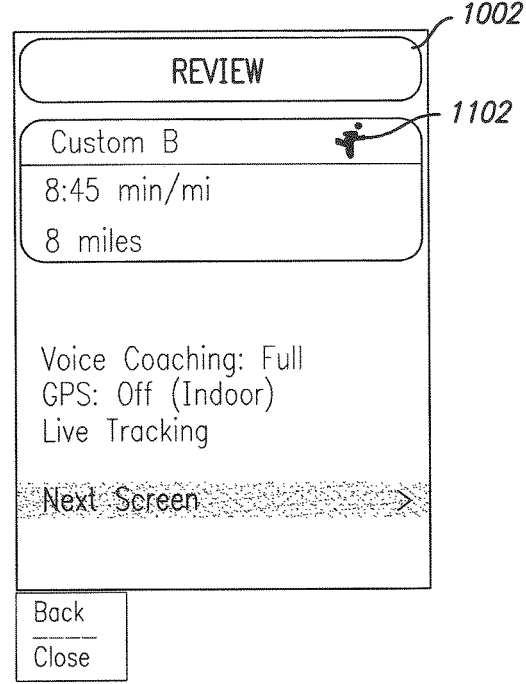
Figure 25C:
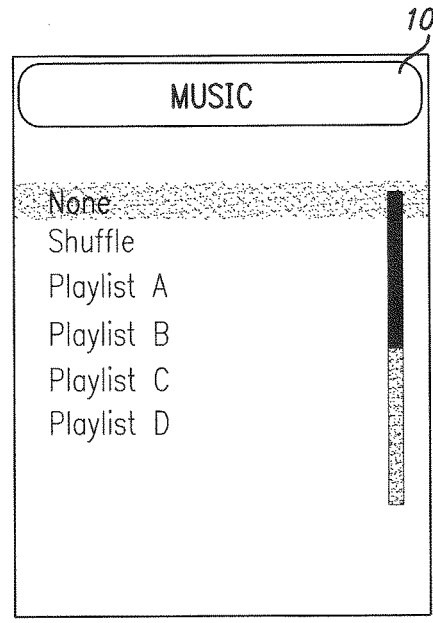
Figure 25D:
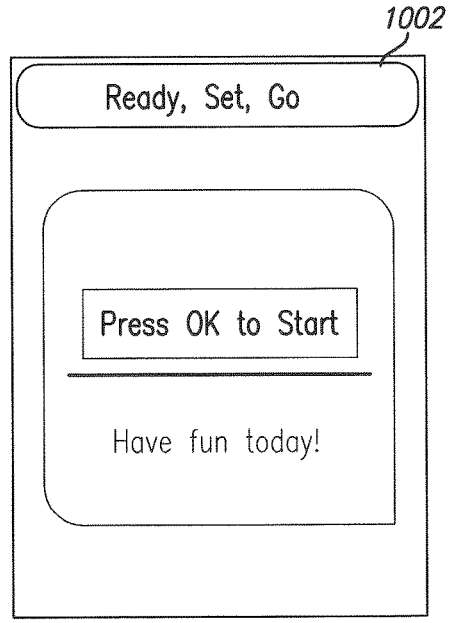

FIG. 24D is an exemplary GUI window that may be provided by the workout selection sub-module of the application software after the athlete 100 has selected voice coaching, satellite positioning system, and/or live tracking options. This GUI window may present music options, which may include selecting no music, selecting from various pre-set playlists of music tracks, or selecting an option to shuffle or randomly play music tracks. In an embodiment, the athlete 100 may be able to select a playlist based on one or more paces, speeds, stride rates, or heart rates associated with the playlist or the tracks that makeup the playlist. In one embodiment, individual music tracks and/or playlists may be stored on the server 112 or a remote personal computer 114 and downloaded to the portable fitness monitoring device 102. In an embodiment, the individual music tracks and/or playlists may be simultaneously downloaded to the portable fitness monitoring device 102 with one or more individual workout routines of a training plan.

After the athlete 100 desiring to partake in a training plan workout has made their selections regarding any available options in response to prompts from the workout selection sub-module, the workout recording sub-module of the go module 1100 may initiate execution of the plan workout routine and begin recording.

As indicated above, however, an athlete 100 may not desire to partake in a training plan workout and may instead prefer to engage in a custom workout. As previously described, a user stationed at a remotely located personal computer 114 may use a website to build a custom workout. Alternatively, the athlete 100 may access the website directly from their portable fitness monitoring device 102 to build a custom workout. The steps for selecting a custom workout routine and choosing the appropriate options are similar to those outlined with respect to FIGS. 23 and 24A-24D. FIGS. 25A-25D illustrate a series of exemplary GUI windows that may be displayed by the workout selection sub-module when the athlete selects custom workout routine. After the athlete 100 desiring to partake in a custom workout has made their selections regarding any available options in response to prompts from the workout selection sub-module, the workout recording sub-module of the go module 1100 may initiate the execution of a custom workout routine and begin recording.

If, however, the athlete 100 not desire to partake in either a training plan workout or a custom workout, they may choose to engage in a free workout. A "free workout" may refer to a situation where no plan or custom performance goals are provided and, thus, where voice coaching is entirely absent during the activity. Because voice coaching is entirely absent, voice coaching options are not presented prior to beginning a free workout. After the athlete desiring to partake in a free workout has made their selections regarding any available options in response to prompts from the workout selection sub-module, the workout recording sub-module of the go module 1100 may initiate the free workout and begin recording.

In one embodiment of the present invention, instead of selecting a training plan, custom, or free workout when presented with the option via a GUI window such as that depicted in FIG. 22B, the athlete 100 may be able to select an "assessment workout." An assessment workout may be used by the fitness monitoring system to assess the relative fitness level of the athlete 100, and/or to establish or modify the athlete's 100 performance zones for one or more parameters (e.g. pace, speed, or heart rate zones), as disclosed in commonly owned U.S. patent application Ser. No. 12/467, 948, titled "Portable Fitness Monitoring Systems with Displays, and Applications Thereof," which has previously been incorporated herein by reference in its entirety.

Figure 26:
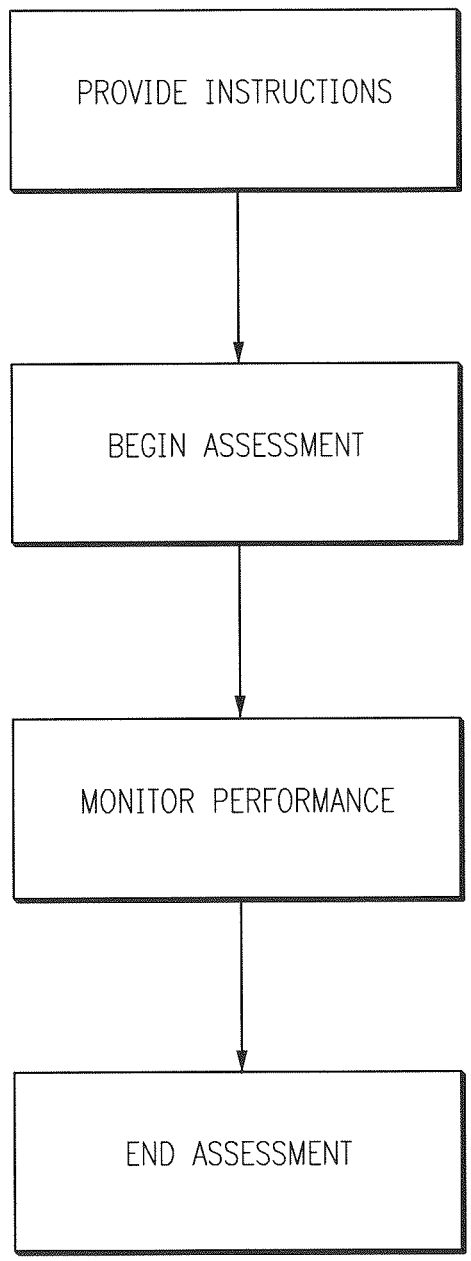
FIG. 26 is a flow chart outlining actions capable of being initiated by software according to an embodiment of the present invention.

As illustrated in FIG. 26, in an embodiment, the portable fitness monitoring device 102 may provide instructions for conducting the assessment workout to the athlete 100, may begin the assessment workout, may monitor the athlete's 100 performance, and may end the assessment workout.

For example, during an assessment workout, the athlete 100 may be prompted to, for example, run as fast as possible for two minutes. The portable fitness monitoring device 102 would then be capable of measuring or estimating the athlete's 100 maximum heart rate or maximum speed based on the actual heart rate or speeds detected during the assessment exercise.

Alternatively, the assessment workout may prompt the athlete 100 to, for example, run at certain percentages of their maximum speed for set periods of time, as subjectively estimated by the athlete 100. For example, the assessment workout may prompt the athlete 100 to try to consistently run at 50%, 75%, and 100% of their maximum speed for consecutive 1 minute periods.

Figure 27:
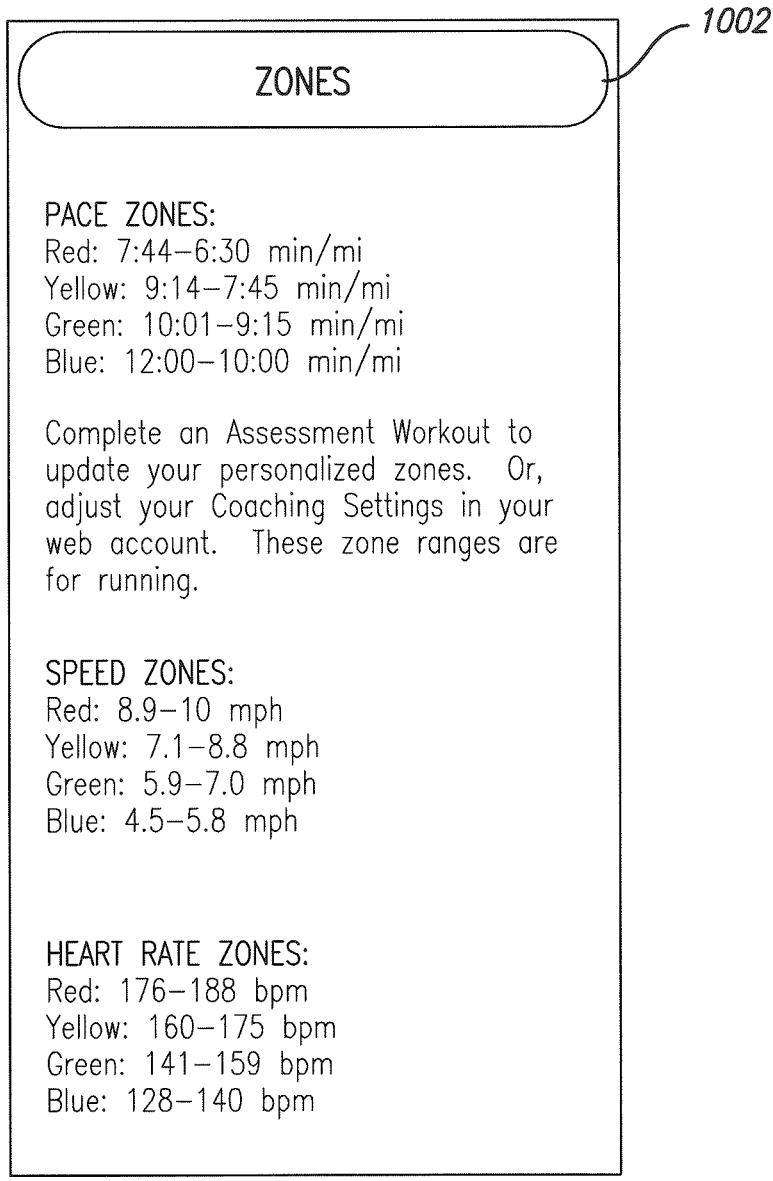
FIG. 27 is an exemplary GUI window according to an embodiment of the present invention.

This information, in turn, could be used alone or in combination with personal information, such as the athlete's 100 age, height, weight, and/or sex, to establish or modify the athlete's 100 performance zones for one or more parameters. FIG. 27 is an exemplary GUI window that may be provided by the workout selection sub-module of the go module 1100 after the athlete 100 has conducted their assessment workout and pace, speed, and/or heart rate performance zones have been established or modified. In an embodiment, different zone ranges may be provided for different activities, such as running or biking.

In one embodiment of the present invention, assessment workout performance information may be sent to the server 112, which also may have access to personal information such as the athlete's 100 age, height, weight, and/or sex, for processing and calculation of the performance zones. In another embodiment, such processing may be done by a processor of the portable fitness monitoring device 102.

After the athlete 100 desiring to partake in a training plan, custom, free, or assessment workout has made their selections regarding any available options in response to prompts from the workout selection sub-module, the workout recording sub-module of the go module 1100 may initiate the workout and begin recording.

Prior to beginning a training plan, custom, free, or assessment workout, the athlete 100 may position the portable fitness monitoring device 102. The portable fitness monitoring device 102 may be worn, carried, or otherwise supported by the athlete 100 during the physical activity. The portable fitness monitoring device 102 may also attach to a piece of exercise equipment such as a road bike traveling on a bike path or a stationary bike in the gym. If necessary, one or more sensors 104 not integrally connected to or included within the portable fitness monitoring device 102 that communicate with the portable fitness monitoring device 102 may also need to be worn, carried, or otherwise supported by the athlete 100.

FIGS. 28A, 28B, 29A-29C, and 30A-30D are exemplary GUI windows that may be displayed by the workout recording application software sub-module after the athlete 100 has chosen to begin a workout according to various embodiments of the present invention.

Figures 28A, 28B:
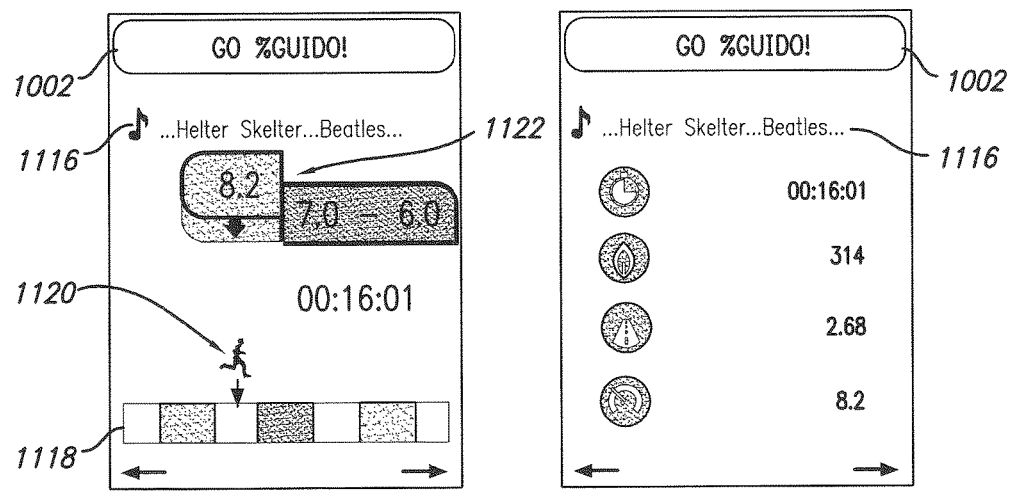
FIGS. 28A and 28B are exemplary GUI windows according to an embodiment of the present invention.

FIGS. 28A and 28B are exemplary GUI windows that may be displayed by the workout recording sub-module executing a workout routine when the athlete 100 is conducting a planned or custom workout that includes color-coded speed-based zone intervals. During a workout, the athlete 100 may toggle between screens corresponding to FIGS. 28A and 28B by manipulating the appropriate user input controls 124. In an embodiment, the screens corresponding to FIGS. 28A and/or 28B may automatically appear at a particular time (e.g. the screen corresponding to FIG. 28B may appear when the athlete 100 is in the proper zone).

As shown in FIGS. 28A and 28B and as described above, a header 1002 may be present near one of the edges of a GUI windows. In addition, message section 1116 may also be present. In FIGS. 28A and 28B, the message section 1116 presents the track name and artist name corresponding to the music track the athlete 100 is currently listening to. In other embodiments, the message section 1116 may present coaching, encouragement, or other messages provided by the portable fitness monitoring service software, or provided by a coach or friend in real time, for example, via a text message.

Because FIGS. 28A and 28B are representative of a situation where the workout routine includes color-coded zone intervals, a progress bar 1118 may be displayed. The progress bar 1118 may be similar to the zone bar indicator 320 that may be associated with a particular workout routine, as described above. In addition to displaying the various color-coded zone intervals of the present workout, the progress bar 1118 may also include a moving progress mark 1120 indicative of where the athlete 100 presently is in their zone-based workout. For example, the progress mark 1120 in FIG. 28A indicates that the athlete presently is in the third color-coded zone interval of their workout, which may be a blue zone. The progress mark 1120 may move along the progress bar 1118 as the athlete progresses through the workout and as the workout routine is executed. In addition, a cumulative workout total such as, for example, total workout time or total workout distance maybe displayed. In FIG. 28A, a total workout time of 16 minutes and 1 second is displayed.

Furthermore, because FIGS. 28A and 28B are representative of a situation where the athlete 100 is conducting a workout that includes at least one color-coded zone goal, a dynamic target bar 1122 may be displayed. The dynamic target bar 1122 may include a left portion and a right portion. The right portion may correspond to the present color-coded zone goal for the athlete 100, based on the current workout routine. The left portion may correspond to the athlete's 100 presently detected and/or measured performance information, as it relates to the present workout routine color-coded zone goal. For example, in FIG. 28A, the right portion of the dynamic target bar 1122 may display a speed range of 7.0 miles per hour to 6.0 miles per hour, which may correspond to a blue zone. The left portion of the dynamic target bar 1122 may display a current athlete 100 speed of 8.2 miles per hour, which may correspond to a yellow zone. Because the athlete 100 is currently exercising at a higher intensity (e.g. yellow vs. blue) that their current workout routine calls for, the dynamic target bar 1122 may provide an indication to the athlete 100 that they need to decrease their intensity. For example, as illustrated in FIG. 28A, the left portion of the dynamic target bar 1122 may be raised above the right portion, and may include a down arrow indicating that the athlete 100 should decrease their intensity.

As described in further detail elsewhere, various color-coded zone-based systems may be employed and zones may be based on a variety of other parameters besides speed. In addition, if the athlete 100 has selected active coaching via the workout selection sub-module of the go-module 1100, the portable fitness monitoring device 102 may provide audible feedback to complement or replace the visual feedback provided by the dynamic target bar 1122. For example, in the situation described above and depicted in FIG. 28A, the portable fitness monitoring device 102 may announce "your intensity is at a yellow zone level, decrease your intensity to enter the blue zone."

As indicated above, during execution of a workout routine, the athlete 100 may toggle between screens corresponding to FIGS. 28A and 28B by manipulating the appropriate user input controls 124. In contrast to the GUI of FIG. 28A, the GUI of FIG. 28B presents summary numerical information for multiple performance parameters, but does not include either a progress bar 1118 or a dynamic target bar 1122. For example, in FIG. 28B, elapsed time, total calories burned, total distance traversed, and average speed are presented.

Figure 29A:
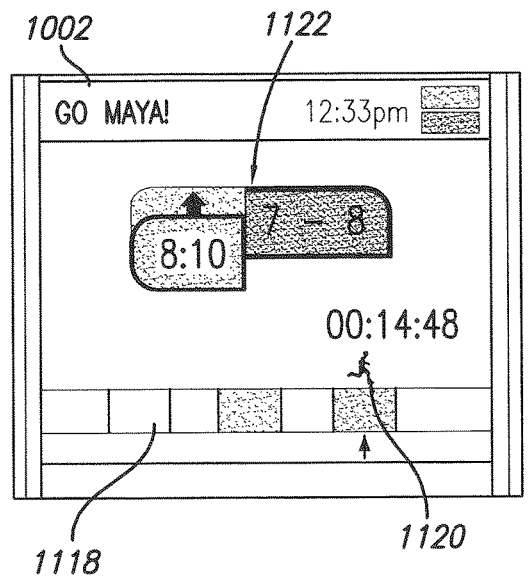
FIGS. 29A-29C are exemplary GUI windows according to an embodiment of the present invention.
Figure 29B:
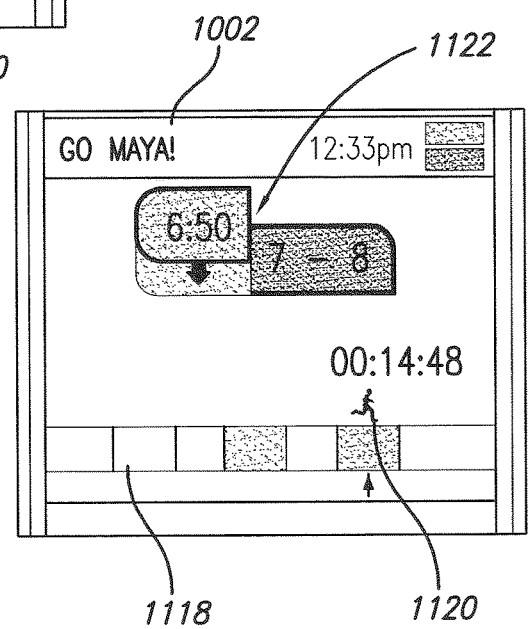
Figure 29C:
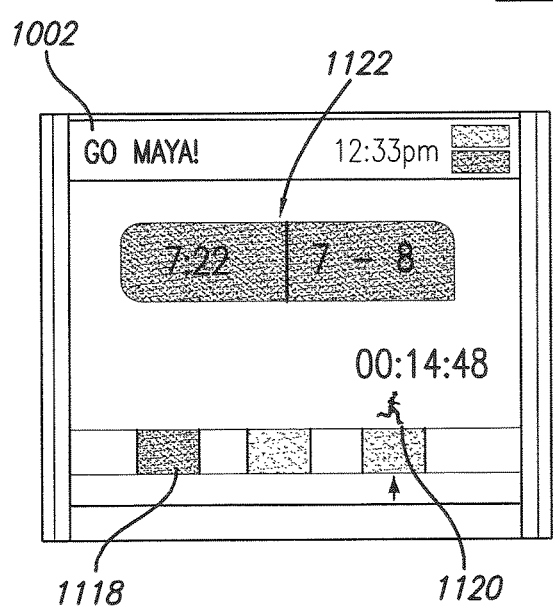

While FIG. 28A illustrates a dynamic target bar 1122 in a situation where the athlete's 100 intensity is too high, similar GUI elements may be presented by workout recording sub-module of the go module 1100 to indicate that the athlete's 100 intensity is either correct or too low. For example, FIGS. 29A-29C illustrate dynamic target bars 1122 in situations where the athlete's pace is too low, too high, and correct, respectively. Each of FIGS. 29A-29C indicate that the target pace range is between seven and eight minutes per mile, which may correspond to a green zone. Thus, the right portion of the dynamic target bars 1122 may be green. In FIG. 29A the left portion of the dynamic target bar 1122 may be blue to represent a slow pace, in FIG. 29B the left portion of the dynamic target bar 1122 may be yellow to represent a fast pace, and in FIG. 29C the left portion of the dynamic target bar 1122 may be green to represent a correct pace.

Figure 30A:
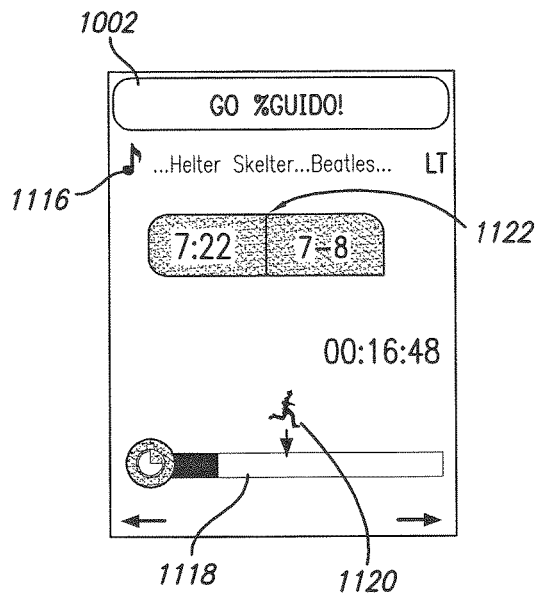
FIGS. 30A-30D are exemplary GUI windows according to an embodiment of the present invention.
Figure 30B:
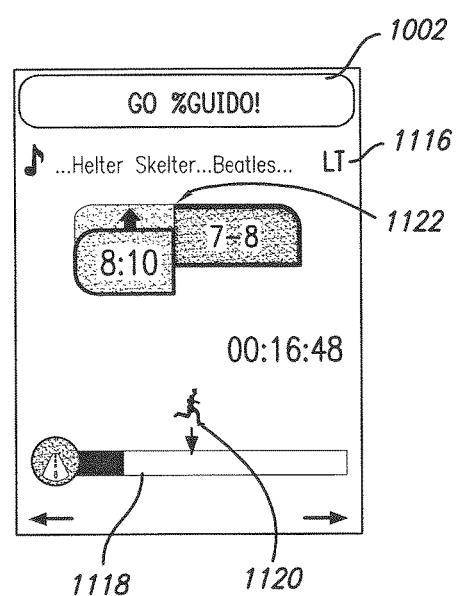

FIGS. 30A and 30B are exemplary GUI windows that may be provided by the workout recording software application sub-module when the athlete 100 is conducting a planned or custom workout that includes at least one color-coded zone goal, but when the planned or custom workout routine does not include a series of color-coded pace-based zone intervals. The GUI windows of FIGS. 30A and 30B are similar to those of FIG. 28A in that both include similar dynamic target bars 1122, though those of FIGS. 30A and 30B relate to pace while those of FIG. 28A relate to speed. Unlike FIG. 28A, which includes a multi-colored, multi-interval progress bar 1118, FIGS. 30A and 30B include a progress bar 1118 capable of providing different information.

For example, in FIG. 30A, the progress bar 1118 may include a black region that will advance from left to right across the progress bar 1118 that represents the athlete's 100 elapsed time in progress to achieving a total time goal. As illustrated in FIG. 30A, a stopwatch icon to the left of the progress bar 1118 may indicate the to athlete 100 that elapsed time is the variable tracked by the progress bar 1118. On the other hand, in FIG. 30B, the progress bar 1118 may include a black region that will advance from left to right across the progress bar 1118 that represents the athlete's 100 distance traversed in progress to achieving a total distance goal. As illustrated in FIG. 30B, a road icon to the left of the progress bar 1118 may indicate the to athlete 100 that distance traversed is the variable tracked by the progress bar 1118. In both the embodiments of FIGS. 30A and 30B, a total elapsed time of 16 minutes and 48 seconds is displayed.

Figure 30C:
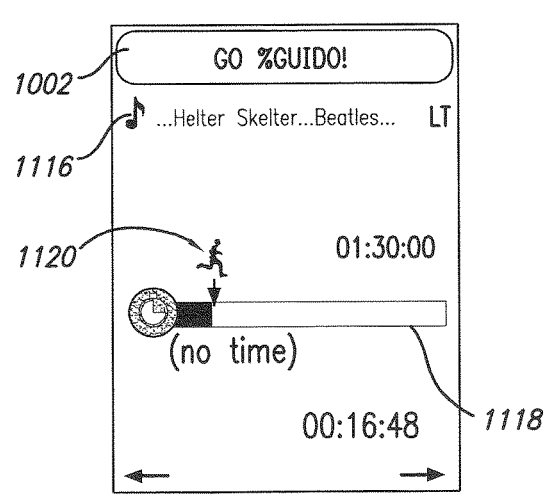
Figure 30D:
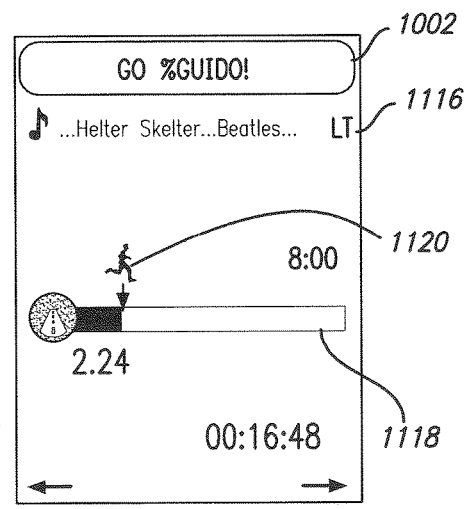

FIGS. 30C and 30D are exemplary GUI windows that may be provided by the workout recording sub-module when the athlete 100 is conducting a planned or custom workout that includes a goal that is not a color-coded zone goal. For example, in the embodiment of FIG. 30C the athlete's 100 goal may be a time goal of 1 hour and 30 minutes. In this embodiment, a stopwatch icon to the left of the progress bar 1118 may indicate the to athlete 100 that elapsed time is the variable tracked by the progress bar 1118. As another example, in the embodiment of FIG. 30D the athlete's 100 goal may be a distance goal of 8 miles. In this embodiment, a road icon to the left of the progress bar 1118 may indicate the to athlete 100 that distance traversed is the variable tracked by the progress bar 1118. FIG. 30D also indicates that the athlete 100 has presently traversed a distance of 2.24 miles.

In some embodiments of the present invention, if an athlete 100 is conducting a free workout, as described above, similar GUI interfaces as those depicted in FIGS. 28A, 28B, 29A-29C, and 30A-30D may still be displayed. In other embodiments, an athlete 100 is conducting a free workout, such GUI interfaces may not be displayed.

Figure 31A:
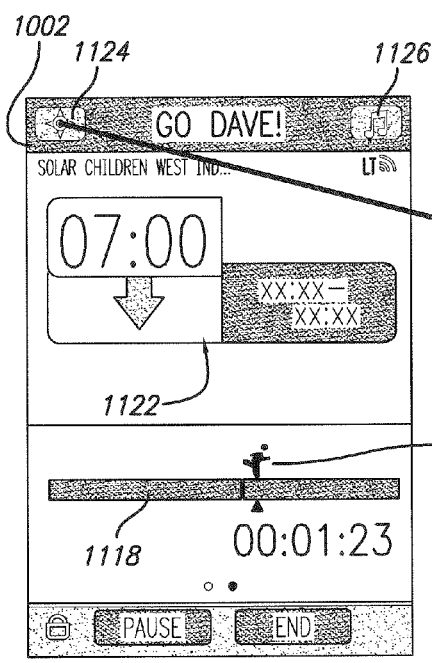
FIGS. 31A and 31B are exemplary GUI windows according to an embodiment of the present invention.

As indicated above, a header 1002 may be present near one of the edges of a GUI window of the present invention. In an embodiment, while the athlete 100 is conducting and recording a workout, the header 1002 may include a map icon 1124 and/or a music icon 1126, as illustrated in FIGS. 31A and 32A.

Figure 31B:
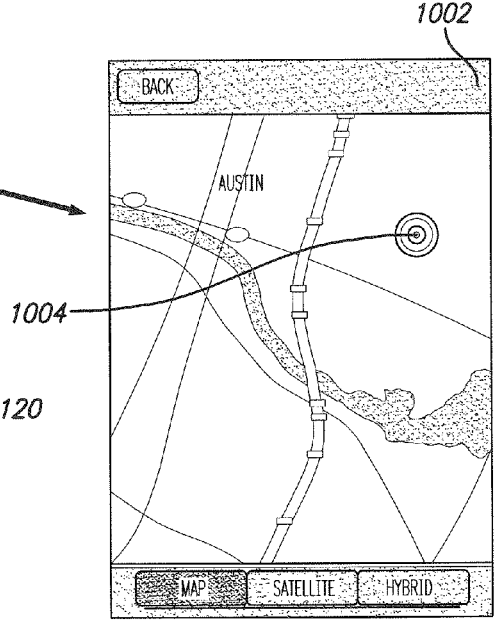

During a workout, the athlete 100 may desire to obtain an indication of their present location with respect to a map. Upon actuating the map icon 1124 illustrated in FIG. 31A using the user input controls 124, the workout recording sub-module of the go module 1100 may present a GUI window such as that illustrated in FIG. 31B, which includes a visual indication of the present location of the athlete 100 on a map. Location information for the athlete 100 may be based in part on location signals received by the positioning system receiver 126 (e.g. a GPS receiver) of the portable fitness monitoring device 102.

During the workout, the athlete 100 may also desire to view the presently selected music playlist and/or select a different music track. Upon actuating the music icon 1126 illustrated in FIG. 32A using the user input controls 124, the workout recording sub-module of the go module 1100 may present a GUI window such as that illustrated in FIG. 32B, which includes an interface for viewing the presently selected music playlist and/or selecting a different music track, such as those interfaces known by those of skill in the art.

In an embodiment of the present invention, throughout the course of the workout, the athlete 100 may be able to pause the workout to temporarily cease performance parameter information recording. The athlete 100 may also be able to end the workout before the goal(s) of the workout have been entirely met.

While the visual and tactile interaction with the system of the present invention has been described above primarily in the context of the display screen 132 and user input controls 124 of the portable fitness monitoring device 102, in an embodiment, at least some of the visual and tactile interaction between the athlete 100 and the system may occur via a wristband or wrist watch, such as those described above with reference to FIG. 2.

For example, a wristband may be capable of displaying performance parameter information in a graphical or numerical way or color-coded performance zone related information. In one embodiment, the wristband may be capable of displaying performance parameter information in a graphical or numerical way such as, for example, a numerical heart rate number on a seven-segment LCD display. In another embodiment, a color emitted by the wristband that corresponds to a particular pace, speed, or heart rate zone may change in character in response to changes in the measured pace, speed, or heart rate occurring within the zone. It may also be possible to use the wristband to receive alerts, control music functions, or to pause workout recording. Other visual and tactile interactions between the athlete 100 and the system of the present invention using a wristband or wristwatch may be possible, such as those interactions disclosed in commonly owned U.S. patent application Ser. No. 12/467,948, titled "Portable Fitness Monitoring Systems with Displays and Applications Thereof," which has previously been incorporated herein by reference in its entirety.

In one embodiment, the athlete 100 may use the user input controls 124 of the portable fitness monitoring device 102 or the user input controls 124 of the wristband to annotate a location on their route as the athlete 100 is traversing the route. For example, when the athlete 100 actuates a particular button, the portable fitness monitoring device 102 may annotate the data record associated with a GPS waypoint associated with the athlete's 100 location at the time of the actuation. In another embodiment, the portable fitness monitoring device 102 may be capable of receiving input from a microphone so that the athlete 100 may audibly annotate a location on their route as the athlete 100 is traversing the route. Such annotations may be useful, for example, for logging the location of points of interest or experiences. For example, the athlete 100 may record voice annotations such as "there's a water fountain here" or "this point in the hill is challenging." In a further embodiment, the portable fitness monitoring device 102 may be capable of receiving input from a keyboard or taking a photo or a video clip to annotate a location on their route as the athlete 100 is traversing the route.

When the athlete 100 completes the workout or chooses to end the workout early, the workout recording sub-module of the go module 1100 may prompt the athlete 100 to save or discard the recorded performance information associated with the workout. If the athlete 100 decides to save their recorded performance information, a summary of their performance may be displayed.

Figure 33A:
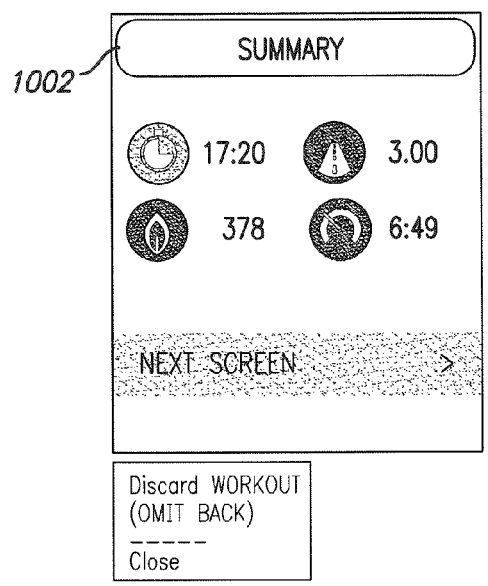
FIGS. 33A-33D are exemplary GUI windows according to an embodiment of the present invention.

FIG. 33A is an exemplary GUI window that may be displayed by the workout recording software application sub-module to provide summary information immediately post-workout. For example, FIG. 33A indicates that the athlete 100 conducted the workout for 17 minutes and 20 seconds, traveled 3 miles, burned 378 calories, and maintained an average pace of 6 minutes and 49 seconds per mile.

In an embodiment of the present invention, the athlete 100 may choose to conduct a workout without the use of a positioning system receiver. In other embodiments of the present invention, the athlete 100 may choose to conduct a workout without the use of other portable sensors 104 such as a portable heart rate monitor or a portable pedometer. In embodiments where certain information has not been recorded by portable sensors 104 but the athlete 100 is still able to record or otherwise calculate these parameters via alternative means, the workout recording sub-module may prompt the athlete 100 to enter the missing information to complete the workout summary information. For example, an athlete 100 may chose to run indoors on a treadmill without using a GPS receiver or other portable sensors capable of providing time, distance, pace, heart rate, and/or calorie information. However, if the treadmill itself provides measured, calculated, or estimate values for these parameters that are displayed to the athlete 100, the athlete 100 may manually enter them into the portable fitness monitoring device 102. In another embodiment, the measured, calculated, or estimate values may automatically be transmitted to the portable fitness monitoring device 102. Measured, calculated, or estimate values for at least one type of parameter may be necessary if the athlete 100 is executing a workout routine that is based upon one or more color-coded zones based upon that parameter. For example, if the athlete 100 is conducting a pace zone based workout while running on a treadmill, the treadmill (or a sensor worn by the athlete 100) must be capable of providing feedback regarding the athlete's 100 pace.

Figure 33B:
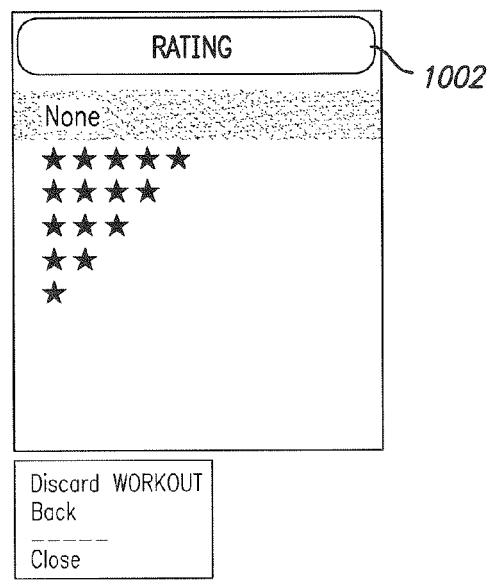

After reviewing summary information (either provided by the portable fitness monitoring device 102 or manually entered by the athlete 100), the athlete 100 may be provided with several other options by the portable fitness monitoring device 102. In one embodiment, as illustrated by FIG. 33B, the athlete 100 may be asked to rate the workout that they just completed, as described in further detail below. For example, the athlete 100 may be able to assign a subjective rating to the workout on a one to five star scale, with more stars corresponding to a better rating.

Figure 33C:
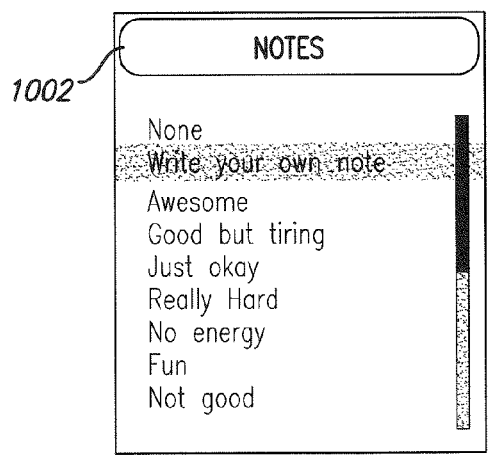
Figure 33D:
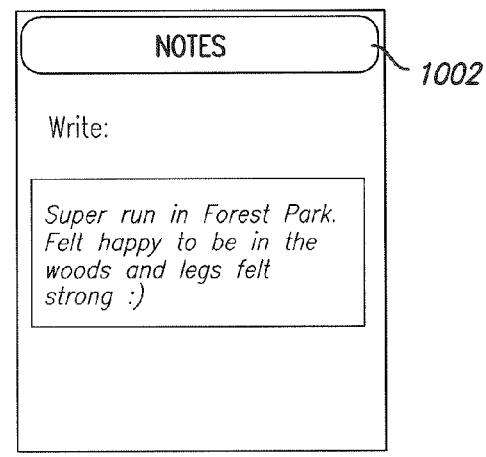

In another embodiment, as illustrated in FIGS. 33C and 33D, the athlete 100 may be able to associate one or more notes with the workout they just completed, as described in further detail below. For example, the athlete 100 may be able to select from one or more default note options, such as those listed in FIG. 33C. Alternatively, as illustrated in FIG. 33D, the athlete 100 may be able to enter their own custom note for the workout using the appropriate user interface controls 124 of the portable fitness monitoring device 102. In yet another embodiment, the athlete 100 may be able to associate a photo or a video clip with the workout they just completed.

In one embodiment of the present invention, the athlete 100 may be able to associate a particular activity type with the record of the workout. For example, the athlete 100 may be able to indicate that he had just engaged in, for example, walking, running, cycling, cross-country skiing, inline skating. For planned workouts for particular types of activities, the type of activity may automatically be associated with the record of the workout. However, because free workouts may not be associated with a particular type of activity ahead of time, it may be necessary for the athlete 100 to make the association. Association of a particular activity type with the record of the workout may advantageously allow for more precise data analysis, feedback, and coaching based on the particular type of activity.

In a further embodiment, the athlete 100 may be able to associate a particular pair of shoes that the athlete 100 wore during the workout with the record of the workout. In one embodiment, after an appropriate prompt from the track module 1200 software application module, the athlete 100 may manually associate a particular pair of shoes with the workout using the user interface controls 124 of the portable fitness monitoring device 102. In another embodiment, the portable fitness monitoring device 102 may be able to automatically detect which pair of shoes were being worn during the activity by detecting the presence of an identifier in one or both of the shoes, such as a specific radio frequency identification (RFID) chip in one or both of the shoes.

As is known by those of skill in the art, passive RFID systems work by employing a reader and a chip. A scanning antenna of the reader emits radio-frequency signals in a relatively short range. These radio-frequency signals communicate with the RFID chip and provide the chip with the energy to engage in the communication. When an RFID chip passes through the field of the scanning antenna of the reader, the chip detects the activation signal from the antenna, wakes up, and it transmits the information stored on the chip to be picked up by the reader. Thus, in the context of embodiments of the present invention, a RFID chip in a particular shoe or pair of shoes may be able to communicate information with a nearby portable fitness monitoring device 102.

As described in further detail below, at a later time, a listing of each pair of shoes the athlete 100 has associated with one or more workouts, along with a cumulative distance that the athlete 100 has traversed while wearing each pair of shoes, may be presented. Athletes 100 may advantageously use this information to determine when a particular pair may need to be replaced, or to determine how particular pairs of shoes have affected the athlete's 100 performance.

After reviewing summary information and after annotating the workout record with any additional information, as described above, the portable fitness monitoring device 102 may either save the complete workout record locally or transmit it to the server 112, as described in further detail elsewhere.

Figures 34A, 34B:
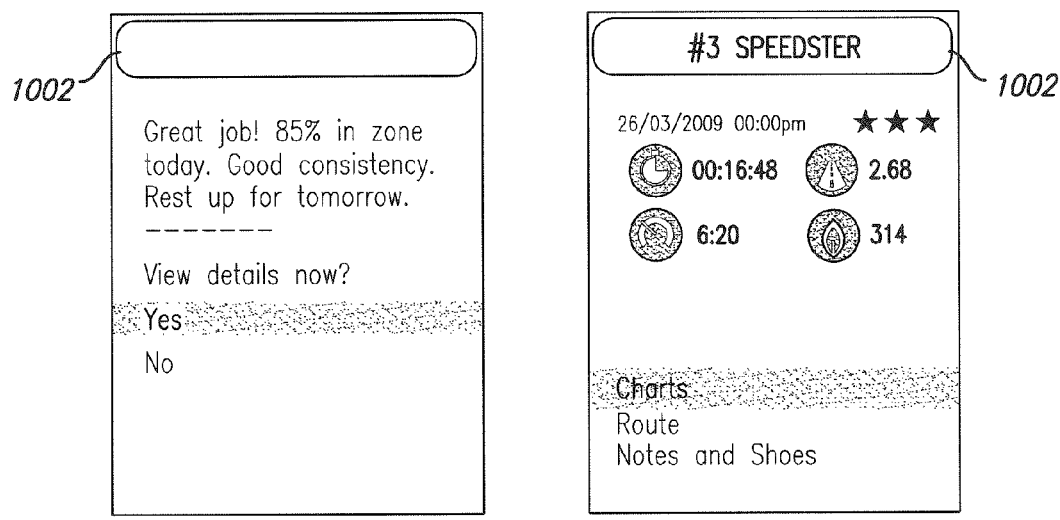
FIGS. 34A and 34B are exemplary GUI windows according to an embodiment of the present invention.

In one embodiment, upon successful upload of a complete workout record to the server 112, the portable fitness monitoring device 102 may prompt the athlete 100 to view more detailed analytical information about the athlete's 100 performance during the workout. As illustrated in FIG. 34A, the workout recording sub-module of the go module 1100 may present a GUI window that provides encouragement or other feedback to the athlete 100 along with the option to review the detailed analytical information. If the athlete 100 opts to review the detailed analytical information, they may be presented with a GUI window similar to that depicted in FIG. 34B by track module 1200, as described in further detail below.

Figure 35:
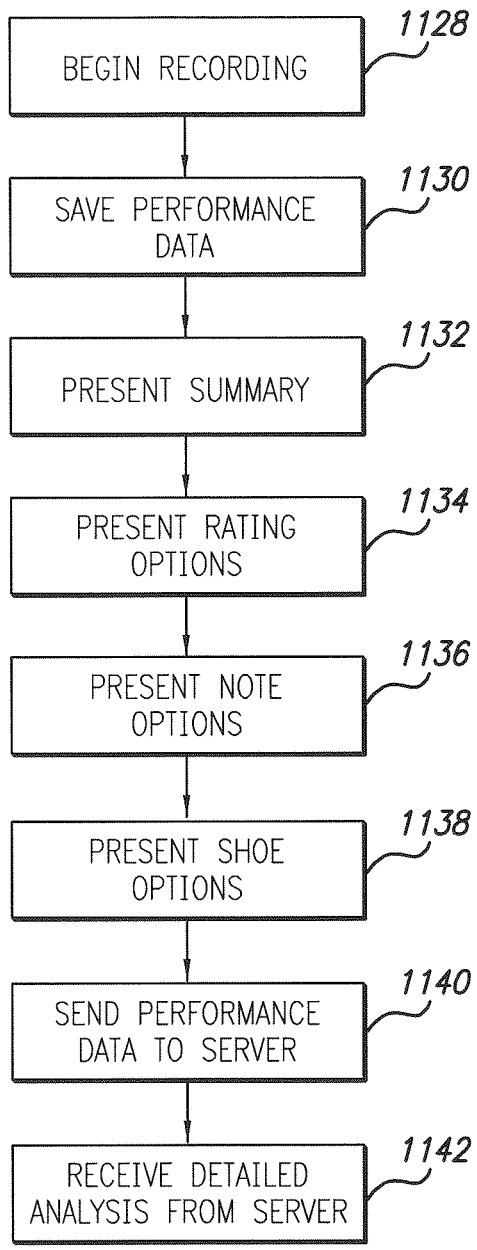
FIG. 35 is a flow chart outlining actions capable of being initiated by software according to an embodiment of the present invention.

The various steps taken by the workout recording sub-module of the go module 1100 of the application software of one embodiment of the present invention may be summarized by the flow chart of FIG. 35. At step 1128, the workout recording sub-module initiates recording of performance information by the portable fitness monitoring device 102. At step 1130, the workout recording sub-module initiates saving of the performance information by the portable fitness monitoring device 102. At step 1132, the workout recording sub-module presents a performance information summary to the athlete 100. At steps 1134-1138, the workout recording sub-module presents rating, note, and shoe tracking options to the athlete 100. At step 1140, the workout recording sub-module initiates the sending of the workout performance information to the server 112. Finally, at step 1142, the workout recording sub-module initiates the receiving of the detailed analytical information about the workout from the server 112.

E. EXEMPLARY POST-ACTIVITY DATA PROCESSING AND FEEDBACK ASPECTS

In some embodiments of the present invention, after the athlete 100 has engaged in a physical activity, a user (who may or may not be the athlete 100) may access a website provided by the server 112 from a remotely located personal computer 114 to review detailed analytical information about the athlete's 100 activity. As previously explained, the personal computer 114 may be, for example, a desktop, laptop, or tablet computer.

However, as described above, in an embodiment, the portable fitness monitoring device 102 itself may also serve as the personal computer 114. Thus, for example, the athlete 100 maybe able to review detailed analytical information about the activity from the portable fitness monitoring device 102 itself after the athlete 100 has engaged in a physical activity. While the description that follows primarily describes the presentation of detailed analytical information in the context of presentation from the server 112 to a user stationed at a personal computer 114 such as a desktop, laptop, or tablet computer, information may also be presented via the portable fitness monitoring device 102 itself to the athlete 100. Thus, while figures of exemplary GUIs suitable at least for display on a personal computer 114 such as a desktop computer are provided, these figures are supplemented with exemplary GUIs suitable at least for display on a portable fitness monitoring device 102.

As explained above with reference to FIG. 8, the application software of the server 112 may include a number of different modules capable of providing fitness monitoring services to athletes 100. In one embodiment of the present invention, these modules include a track module 500. The track module 500 allows the users to review and analyze an athlete's 100 past performance data. After completing a workout and uploading performance data to the server 112, the athlete 100 may log in to the server 112 to review and analyze their past performance data.

In one embodiment, for each completed workout routine, a workout journal page may list the date the workout was completed, the name of the workout, and one or more performance details about the workout. For example, the workout journal page may list the elapsed time of the workout, the calories burned during the workout, the distance covered during the workout, the athlete's 100 average heart rate during the workout, the athlete's 100 average pace during the workout, the athlete's 100 average stride rate during the workout, a subjective athlete 100 rating of the workout and/or route, an automatic computer rating of the workout and/or route, the type of activity the athlete 100 conducted, and any other notes the athlete 100 wishes to record. The particular information displayed on the workout journal page may be set by the system or customized by the user.

As described above with reference to FIG. 33B, the subjective rating may be assigned by the athlete 100 immediately after the workout is completed, or at a later time. In one embodiment, the athlete 100 may rate a workout on a one to five star scale, with a one star workout being a poor workout and a five star workout being an excellent workout. In one embodiment, the athlete 100 rating may be entirely subjective. Alternatively, the rating may be assigned by track module 500 objectively, based on various recorded performance parameters from the workout, historical athlete 100 performance, and/or user settings and options. For example, an objective route difficulty rating may be assigned to the workout based on one or more of route length, elevation changes over the route, altitude of the route, temperature during the athletic performance, humidity during the athletic performance, wind speed during the athletic performance, and wind direction during the athletic performance.

The athlete 100 notes may also be assigned by the athlete 100 immediately after the workout is complete, as described above with reference to FIGS. 33C and 33D, or at a later time. Athlete 100 notes may include, for example, explanations of a rating assigned to the workout, or other subjective or objective observations about the workout, the athlete's 100 condition, the environment the workout was conducted in, or the route traversed.

In addition to (or in place of) being able to review and analyze past performance data via the workout journal page, the user may be able to select an icon capable of initiating a history sub-module. The history sub-module of the application software may be capable of displaying a variety of GUI windows to the user such as, for example, those shown in FIGS. 36-40.

Figure 36:
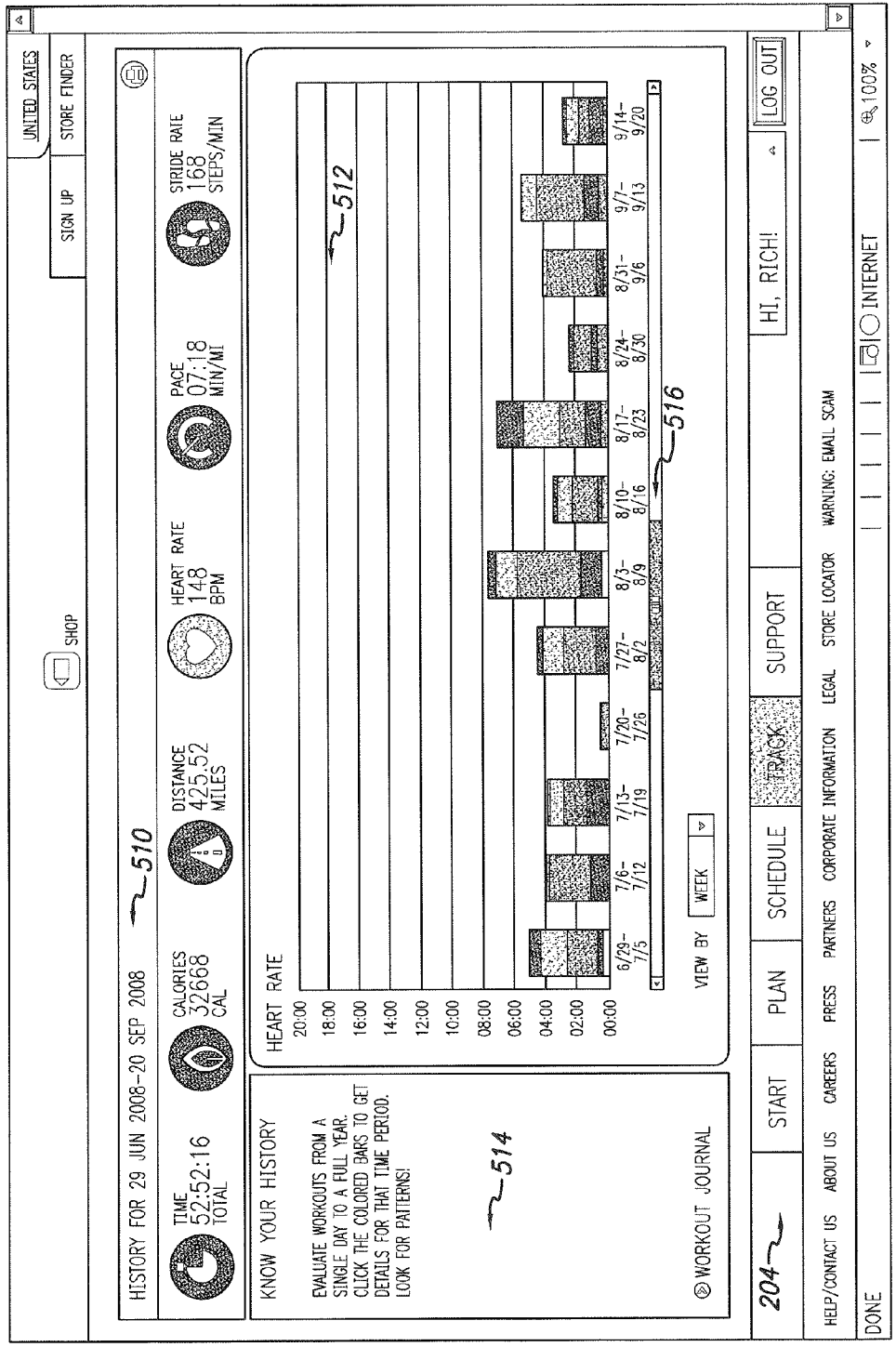
FIG. 36 is an exemplary GUI window according to an embodiment of the present invention.

FIG. 36 is an exemplary GUI window according to an embodiment of the present invention that may be presented by the history sub-module. History pages may include a dashboard 510, a primary display 512, and a sidebar 514. The dashboard 510 may provide icons that are correlated to particular performance parameters. Each icon itself may provide information about the performance parameters, and selecting a specific icon with a cursor may alter the information displayed by the primary display 512. The sidebar 514 may provide additional information, icons, and/or options.

The information displayed on the history pages may be for a single workout or for a plurality of workouts falling within a particular date range. Information may be displayed on a yearly, monthly, weekly, or daily basis. The data range selected by the user may affect the information displayed by the dashboard 510 icons, the information displayed on the primary display 512, as well as the content of the sidebar 514.

The dashboard 510 shown in FIG. 36 includes display icons for time, calories, distance, heart rate, pace, and stride rate. In an embodiment, a display icon for total elevational ascent may also be provided. The numerical information provided with the dashboard 510 icons corresponds to data associated with workouts from the date range selected. For example, as illustrated in FIG. 36, for the selected period of Jul. 27, 2008, through Aug. 16, 2008, the user's total workout time was 52 hours, 52 minutes, and 16 seconds. This value may also be provided in cumulative and/or average form over the selected time period.

While the information provided by the dashboard 510 icons may remain the same for a given date range, the information displayed by the primary display 512 may change depending on which dashboard 510 icon the user has selected. For example, in FIG. 36, because the user has selected the heart rate icon in the dashboard 510, the history sub-module 504 displays heart rate information in the primary display 512.

While FIG. 36 shows the information displayed by the primary display 512 in the form of bar graphs, other suitable graphical displays such as, for example, line graphs, pie graphs, race course representations, animations, or videos may be provided in addition to or in place of the bar graphs. Moreover, although only heart rate graphs have been illustrated by FIG. 36, any performance parameters listed in the dashboard 510 may be graphically displayed in the primary display 512. For example, FIG. 37 illustrates an exemplary history page where pace information is displayed in the primary display 512 in bar graph form.

As shown in FIG. 36, when daily heart rate information is displayed in the primary display 512 in bar graph form, the heart rate information may be conveyed based on the color-coded heart rate zone system described above with respect to FIG. 10. When daily, weekly, or monthly pace, stride rate, or other parameter information is displayed in the primary display 512 in bar graph form, this information may or may not be conveyed based on a color-coded zone system corresponding to these other parameters.

Figure 37:
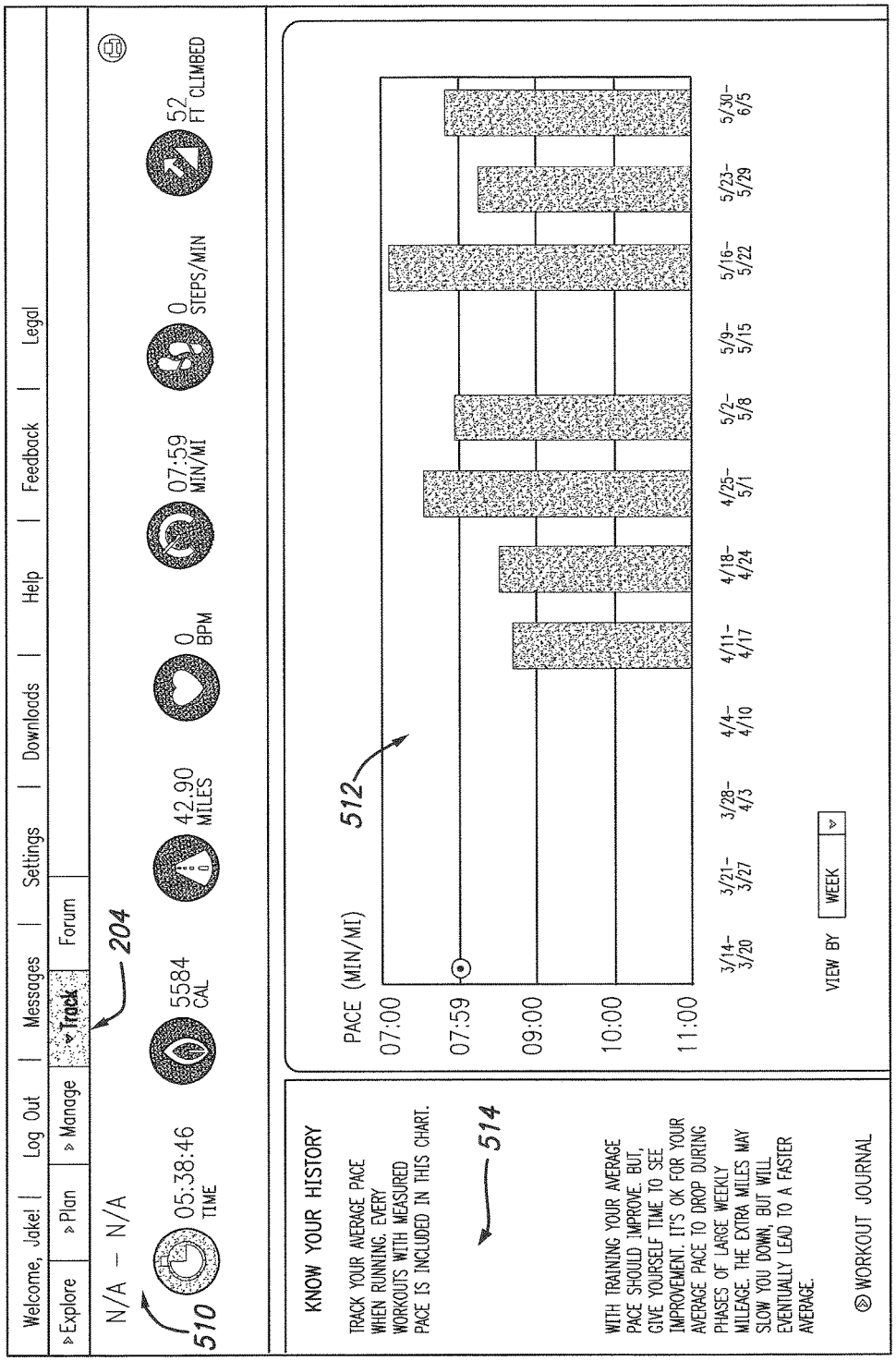
FIG. 37 is an exemplary GUI window according to an embodiment of the present invention.

As shown in FIG. 37, while only pace information is displayed in the primary display 512 in bar graph form, other performance parameter information may be overlaid in bar graph form. For example, a heart rate bar graph may be overlaid or placed next to of the pace based graph so that both parameters could be compared.

In one embodiment, an athlete 100 who wishes to obtain even more specific information about a period of time displayed within the primary display 512 may select the bar or other indicium representing the appropriate time period with their cursor (e.g. by clicking on the bar or other indicium). For example, if the user viewing the daily GUI window of FIG. 36 wanted to obtain more specific information about workouts conducted on Aug. 9, 2008, the user 100 could select the bar representing that day, which may result in the history sub-module displaying the daily GUI window shown in FIG. 38.

Figure 38:
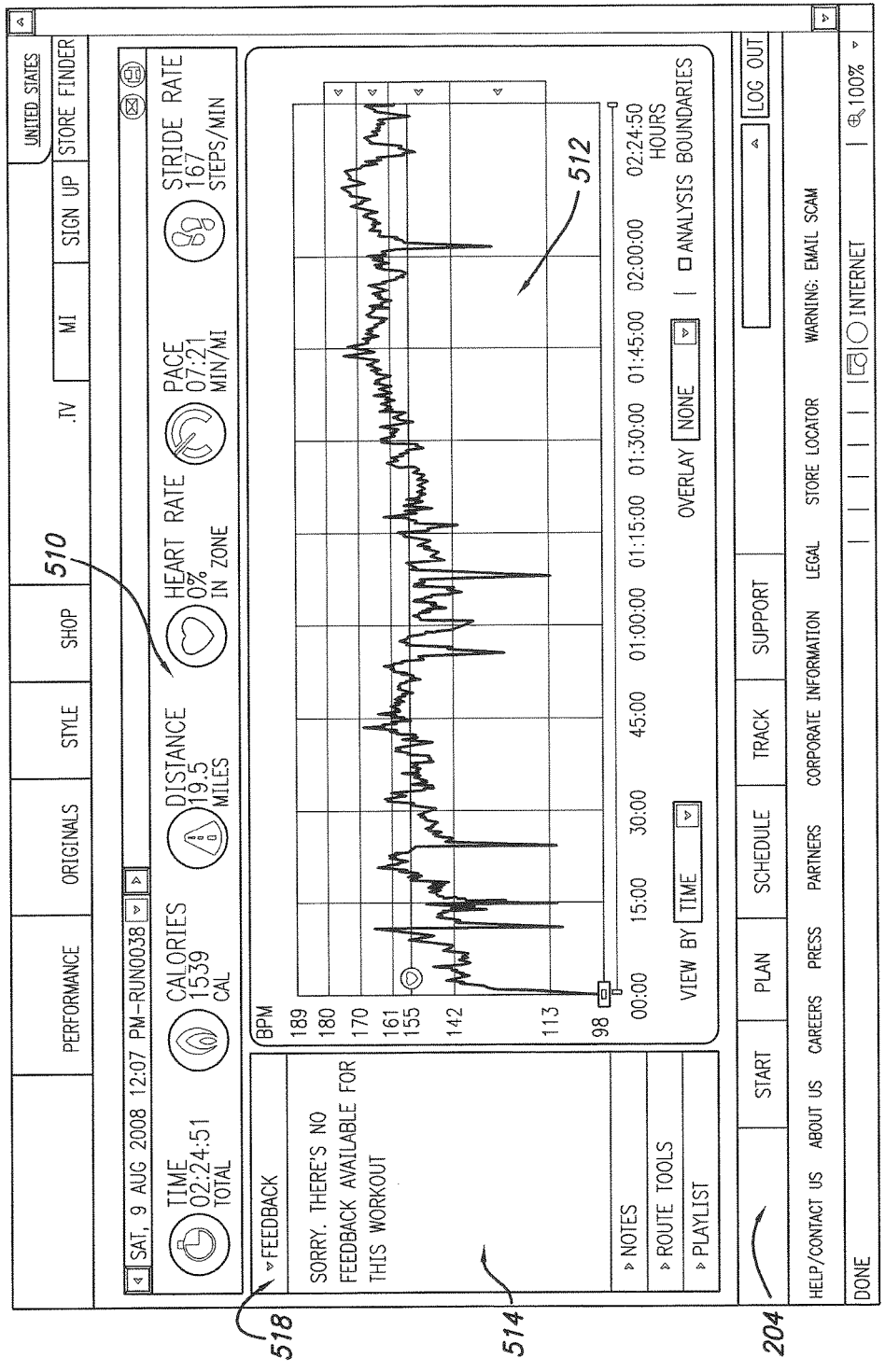
FIG. 38 is an exemplary GUI window according to an embodiment of the present invention.

The history display shown in FIG. 38 is similar to the display shown in FIG. 36 in that the dashboard 510, primary display 512, and sidebar 514 are still present. However, FIG. 38 differs from FIG. 36 in that information provided in both the dashboard 510 and the primary display 512 is only associated with a single workout day. Additional functionality may also provided by the sidebar 514.

Figure 39:
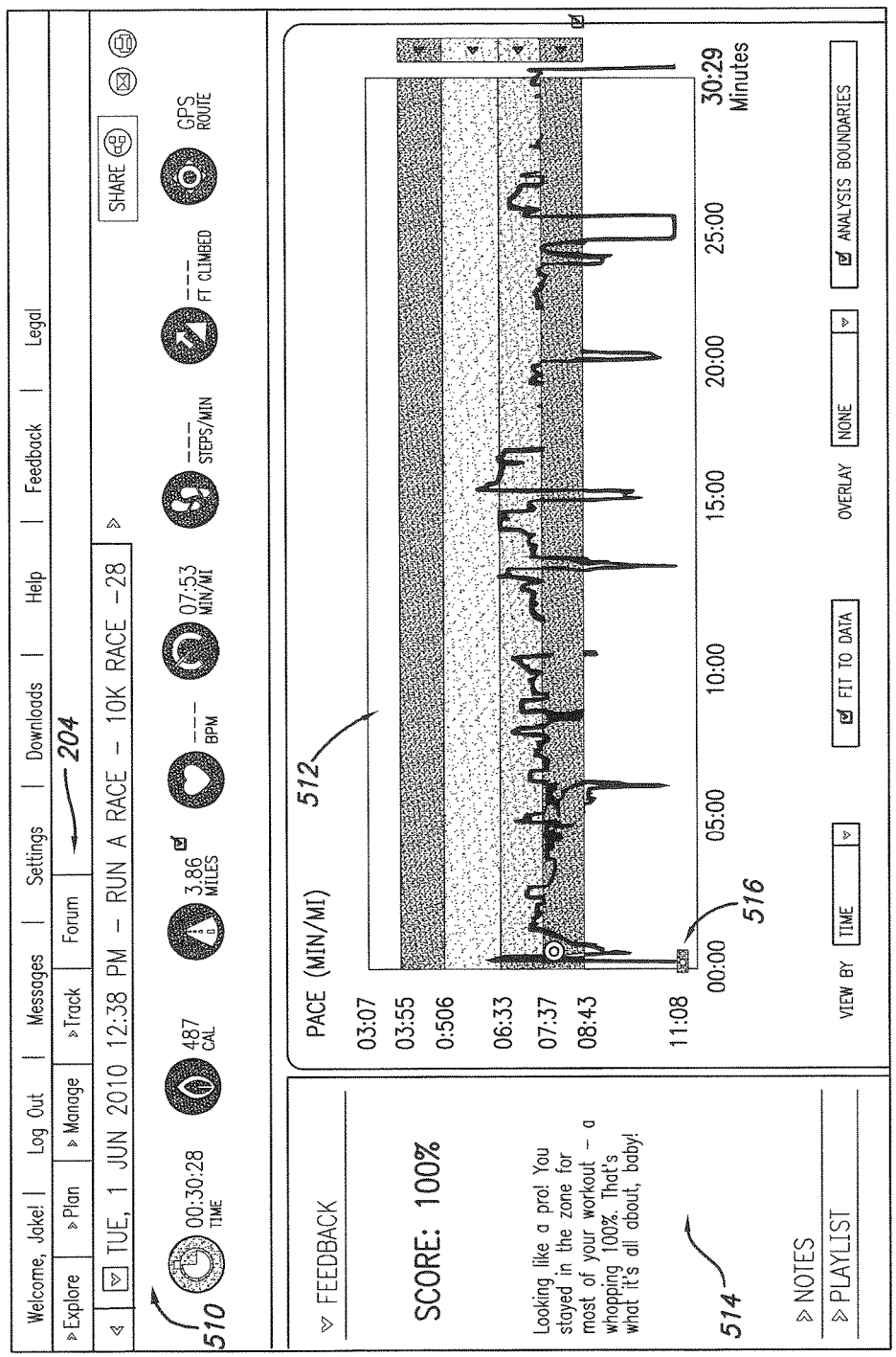
FIG. 39 is an exemplary GUI window according to an embodiment of the present invention.

Similarly, the history display shown in FIG. 39 is similar to the display shown in FIG. 38, except that FIG. 39 illustrates an exemplary history page where pace information is displayed instead of heart rate information.

In one embodiment of the present invention, as shown in FIG. 38, the history sub-module may provide a feedback 518 section in the sidebar 514. The feedback section may provide feedback from coaches, friends, or other users authorized to provide feedback to the athlete 100. All users of the system of the present invention having similar accounts through server 112 may be authorized to provide feedback to the athlete 100. Alternatively, only users of the system that are specifically authorized by the athlete 100 may provide feedback to the athlete 100. In an embodiment, users who are linked to the athlete 100 via a social networking site may also provide feedback to the athlete 100. Feedback may be provided through a GUI provided by sever 112, via email, via text message, via voice mail, or by any other suitable means known in the art. Feedback may be listed sequentially in the order that the feedback was posted, much like comments associated with a blog entry or other web article, as is known by those of skill in the art.

The history sub-module may also provide a notes section in the sidebar 514. The notes section may provide a section for a user rating and user notes. These ratings and notes may be similar to those described above with reference to FIGS. 33B-D and 35.

The history sub-module may provide a route tools section in the sidebar 514 that may be managed by a route tools software application sub-module, as described in further detail below.

In another embodiment of the present invention, the history sub-module may further provide a playlist section in the sidebar 514. If the athlete 100 conducted a workout while listening to music on a music-enabled portable fitness monitoring device 102, the playlist section may provide a listing of the musical audio tracks that the athlete 100 listened to during their workout.

In an embodiment, a particular play list may be associated with a particular route plan or workout routine so that the play list may be downloaded to the portable fitness monitoring device 102 simultaneously with the route plan and/or workout routine. Accordingly, the athlete 100 may be able to easily execute the same (or substantially the same) workout routine and/or traverse the same route while listening to the same play list. The athlete 100 could also fine tune their play list until the athlete 100 felt that the play list provided appropriate entertainment, motivation, or other benefits during the physical activity.

In one embodiment, the performance information to be displayed in the primary display 512, based on the selected dashboard 510 icon, may be displayed on a line graph whose x-axis is either time or distance based, and whose y-axis is correlated to the value of the measured performance parameter. For example, as shown in FIG. 38, a line graph charts heart rate information as a function of time during the workout. In FIG. 39, a line graph charts pace information as a function of time during the workout.

Average lines may also be plotted parallel to the x-axis across the graphs. For example, in FIG. 38, an average heart rate line representing the athlete's 100 average heart rate of 155 beats per minute during the workout is plotted across the graph.

Figure 40:
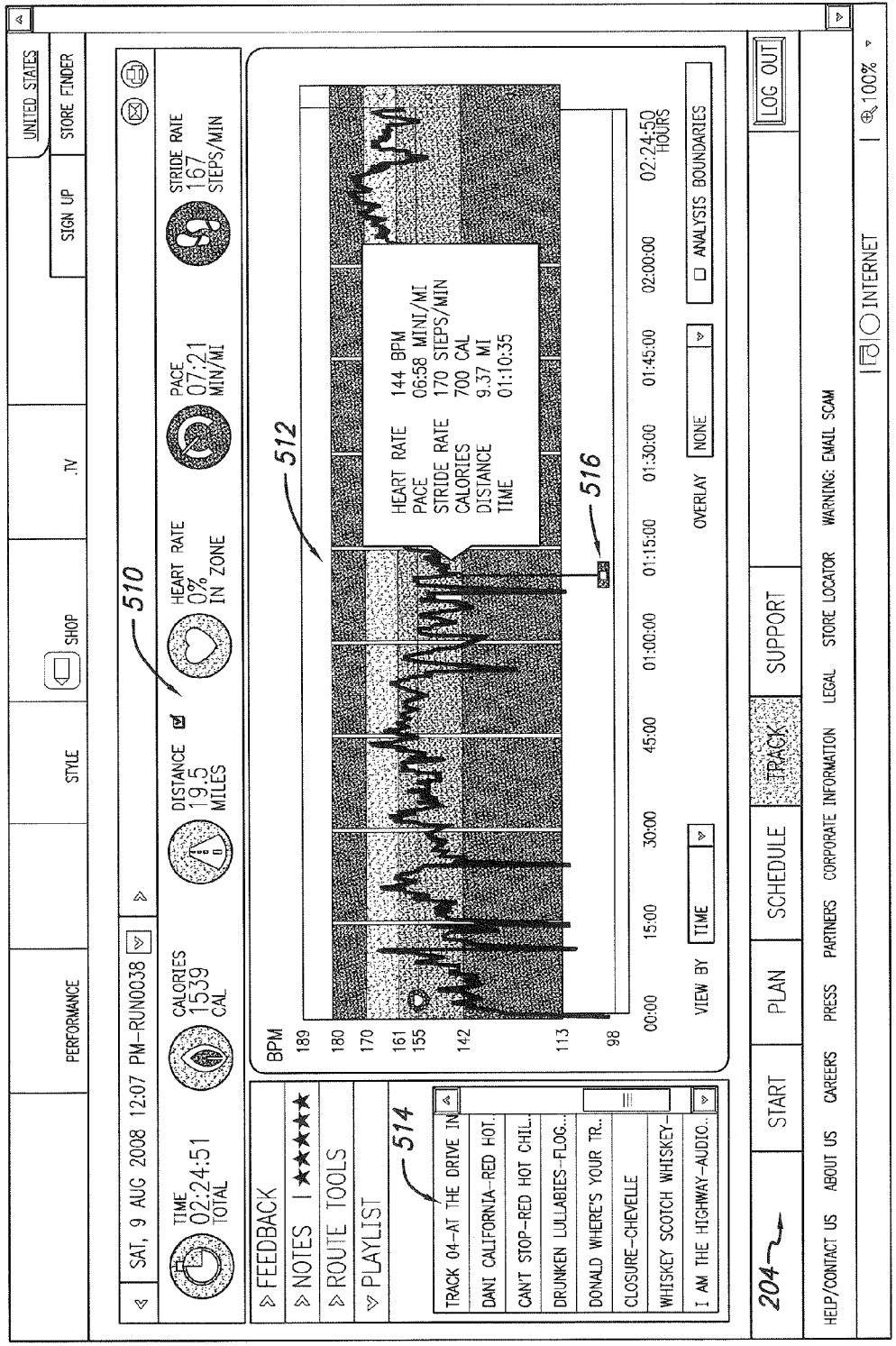
FIG. 40 is an exemplary GUI window according to an embodiment of the present invention.

A user interested in viewing instantaneous performance statistics over the course of the workout may be able to select and drag a scrollbar 516 with a cursor along the x-axis. As the user drags the scrollbar 516 across the x-axis, an icon may travel along the line graph plotted for the performance parameter of interest. In addition, a pop-up window displaying additional instantaneous performance data may appear and move across the screen along with the moving icon. FIG. 40 is an illustration of an icon and pop-up window containing instantaneous performance parameter information being moved across a GUI screen by means of a scrollbar 516.

In an embodiment, the user may be able to manually correct any recorded parameters that they know are inaccurate. Inaccuracies may be due to, for example, errors with the sensors 104 employed by the portable fitness monitoring device 102 used by the athlete 100. A user may correct, for example, the distance the athlete 100 traveled during a workout. The user may know the exact distance of a route routinely traveled and wish to update a distance inaccurately recorded by a distance sensor 104.

In another embodiment, when a parameter, such as distance, is corrected, the system may recalibrate the recorded and stored data. For example, when the distance traversed for a particular activity is corrected, the distance data and corresponding distance graph for that activity is corrected. In addition, data and graphical displays that depend on the distance data, such as pace data and graphical displays, are also corrected.

In a further embodiment, when a parameter, such as distance, is corrected, this corrected data may be transmitted to the portable fitness monitoring device 102 the next time the device is in communication with the network 112 so that the portable fitness monitoring device's 102 distance monitoring capability can be recalibrated, if necessary.

While these tracking features have been described primarily in the context of presentation from the server 112 to a user stationed at a personal computer 114 such as a desktop, laptop, or tablet computer, in an embodiment of the present invention, GUIs providing information and functionalities similar to those provided by the GUIs depicted in FIGS. 36-40 may be provided to the athlete 100 via the portable fitness monitoring device 102, such as a smart phone.

Figures 41A, 41B:
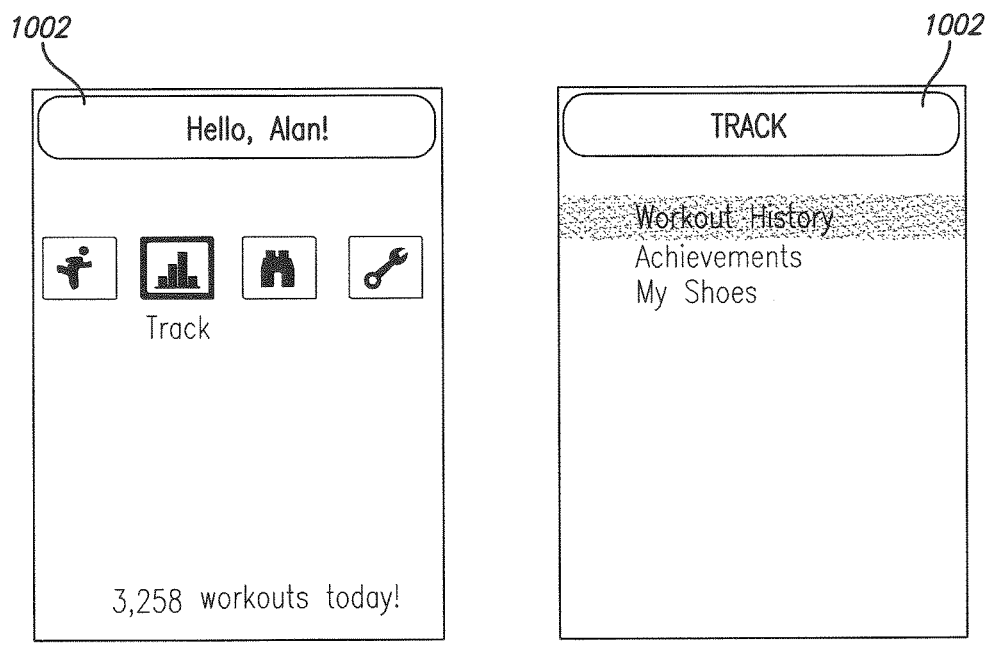
FIGS. 41A and 41B are exemplary GUI windows according to an embodiment of the present invention.

For example, FIG. 41A is an illustration of a home page GUI displayed via the portable fitness monitoring device 102, where the athlete 100 has highlighted an icon corresponding to the track module 1200 application software module. The track module 1200 may include a workout history sub-module, an achievements sub-module, and a shoes sub-module. As explained in further detail below, certain aspects of the workout history sub-module of the track module 1200 of the portable fitness monitoring device may be similar to aspects of the history sub-module of the track module 500 of the server 112, as described above.

After the athlete selects the icon corresponding to the track module 1200, the track module 1200 my present the athlete 100 with the option of receiving additional information regarding workout histories, achievements, or shoes, as illustrated in FIG. 41B. When the athlete 100 indicates that they would like to receive additional information regarding workout histories, the workout history sub-module may present a GUI such as the exemplary GUI window shown in FIG. 42A.

Figures 42A, 42B:
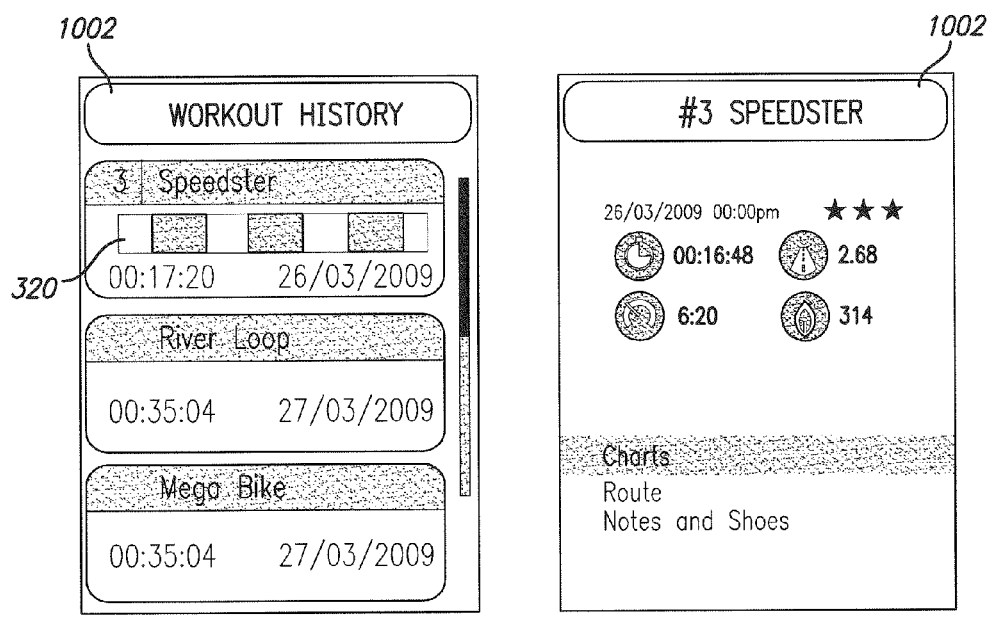
FIGS. 42A and 42B are exemplary GUI windows according to an embodiment of the present invention.

FIG. 42A lists several individual workouts accessible in the workout history of the portable fitness monitoring device 102. In an embodiment, only individual workouts recorded in the last week are listed. In another embodiment, only individual workouts recorded in the last month are listed. The workout list may provide only limited statistical details about each individual workout. As shown in FIG. 42A, an individual workout comprised of color coded zone intervals may be represented by a zone bar indicator 320, similar to that discussed above. The GUI window may also indicate the duration of each individual workout and the date that it was conducted. In an embodiment, the GUI of FIG. 42A may be similar to the workout journal page that may be provided by the server 112 to a user stationed at a personal computer 114, as described above.

FIG. 42B is an exemplary GUI window according to an embodiment of the present invention that may be displayed when the athlete 100 selects an individual workout from the workout list of FIG. 42A. This GUI window may provide, for example, summary workout information and a route rating as described above with respect to FIG. 34B. As illustrated in FIG. 42B, a drop down menu may be provided that allows the athlete 100 to request additional information regarding charts, routes, and other notes.

If the athlete 100 requests additional information regarding other notes, information that the athlete 100 entered in response to the prompts described above at steps 1136 and 1138 of FIG. 35 regarding general notes and shoes may be provided.

Figure 43A:
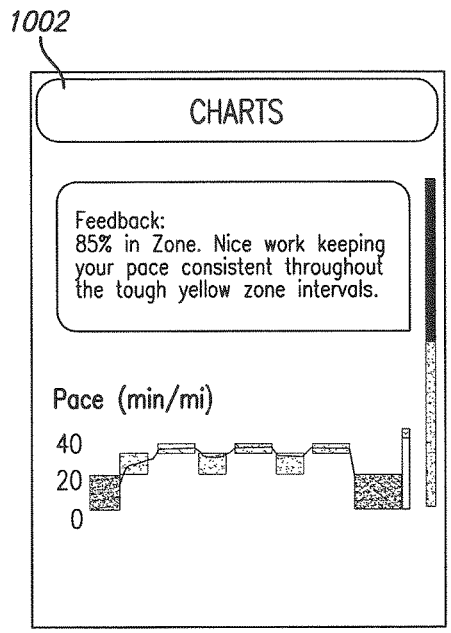
FIGS. 43A-43C are exemplary GUI windows according to an embodiment of the present invention.
Figure 43B:
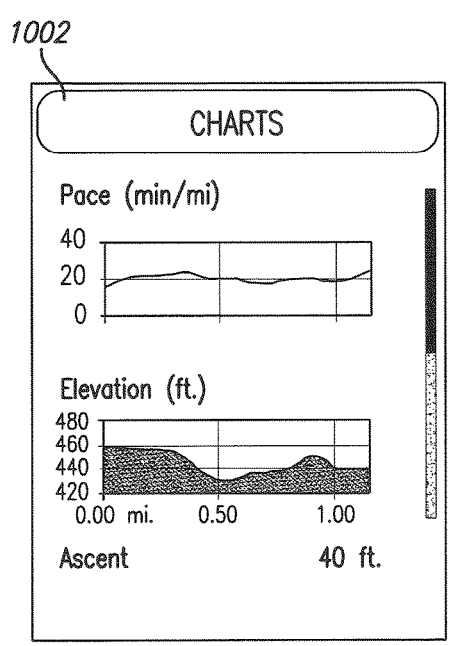
Figure 43C:
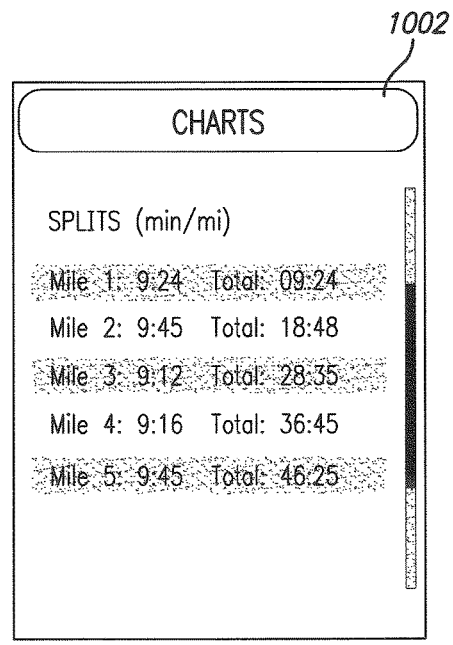

FIGS. 43A-43C illustrate an exemplary GUI window according to an embodiment of the present invention that may be displayed when the athlete 100 requests additional information regarding charts. The workout history sub-module of the track module 1200 application software module may display a window including a variety of different charts, statistics, and/or other graphics. Coaching notes may also be included. As the athlete 100 scrolls down the screen, the images illustrated in FIGS. 43A-43C may be presented. In one embodiment, graphs similar to those illustrated in FIGS. 36-40 may be presented. In another embodiment, the graphs and charts presented may convey information similar to that conveyed by the graphs of FIGS. 36-40, but the graphs and charts may be relatively less complex and more suitable for a smaller display screen of a portable fitness monitoring device 102.

Returning to the presentation of information from the server 112 to a user stationed at a personal computer 114 such as a desktop or laptop computer, in an embodiment of the present invention, graphical representations of the routes traversed by the athlete 100 during individual workouts may be presented to the user. As described above, the history sub-module of the track module 500 of the server 112 may be capable of presenting a route tools section in a sidebar 514 that may be managed by a route tools sub-module.

In one embodiment, the route tools sub-module may allow the user 100 to associate specific routes with a workout when the workout involved the traversal of a particular geographic pathway. In one embodiment, the route tools sub-module may employ a web-based mapping service application, such as, for example, the Google Maps application provided by Google, Inc. of Mountain View, Calif. The mapping service application may utilize an application programming interface that allows the mapping service application, such as Google Maps, to be embedded into the GUI windows of the present invention.

Figure 44:
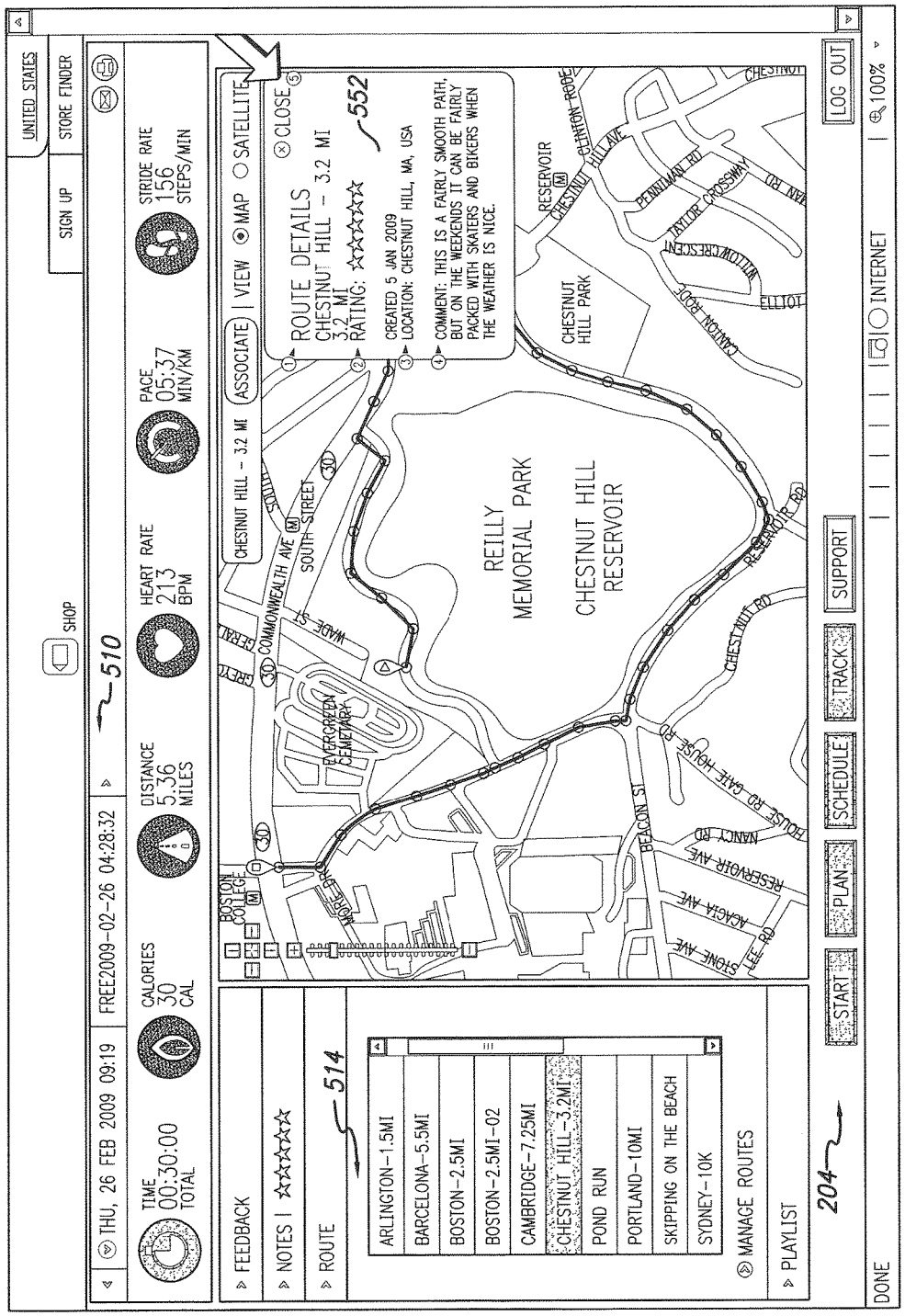
FIG. 44 is an exemplary GUI window according to an embodiment of the present invention.

In one embodiment, the route tools sub-module may enable the user to recreate the path traversed by the athlete 100 during the workout by clicking, and/or dragging and dropping landmarks and paths over a street map using a cursor. The approximate area of the route may be found by, for example, entering a street address, a well-known landmark, or a zip code into the mapping service application interface. Alternatively, in an embodiment, as illustrated in FIG. 44, the athlete 100 could conduct their workout using a GPS-enabled portable fitness monitoring device 102 capable of recording their geographic way points along the route traversed. Either during traversal of the route or after the route has been completed, the GPS data could then be uploaded to the server 112 and associated with other performance monitoring information collected during traversal of the route. Thus, the route tools sub-module could automatically reconstruct the path traversed by the athlete 100. In an embodiment, as illustrated in FIG. 44, an route details box 552 may provide summary information about the route such as, for example, distance, rating, creation date, location, comments, notes, and/or other relevant information.

Figure 45:
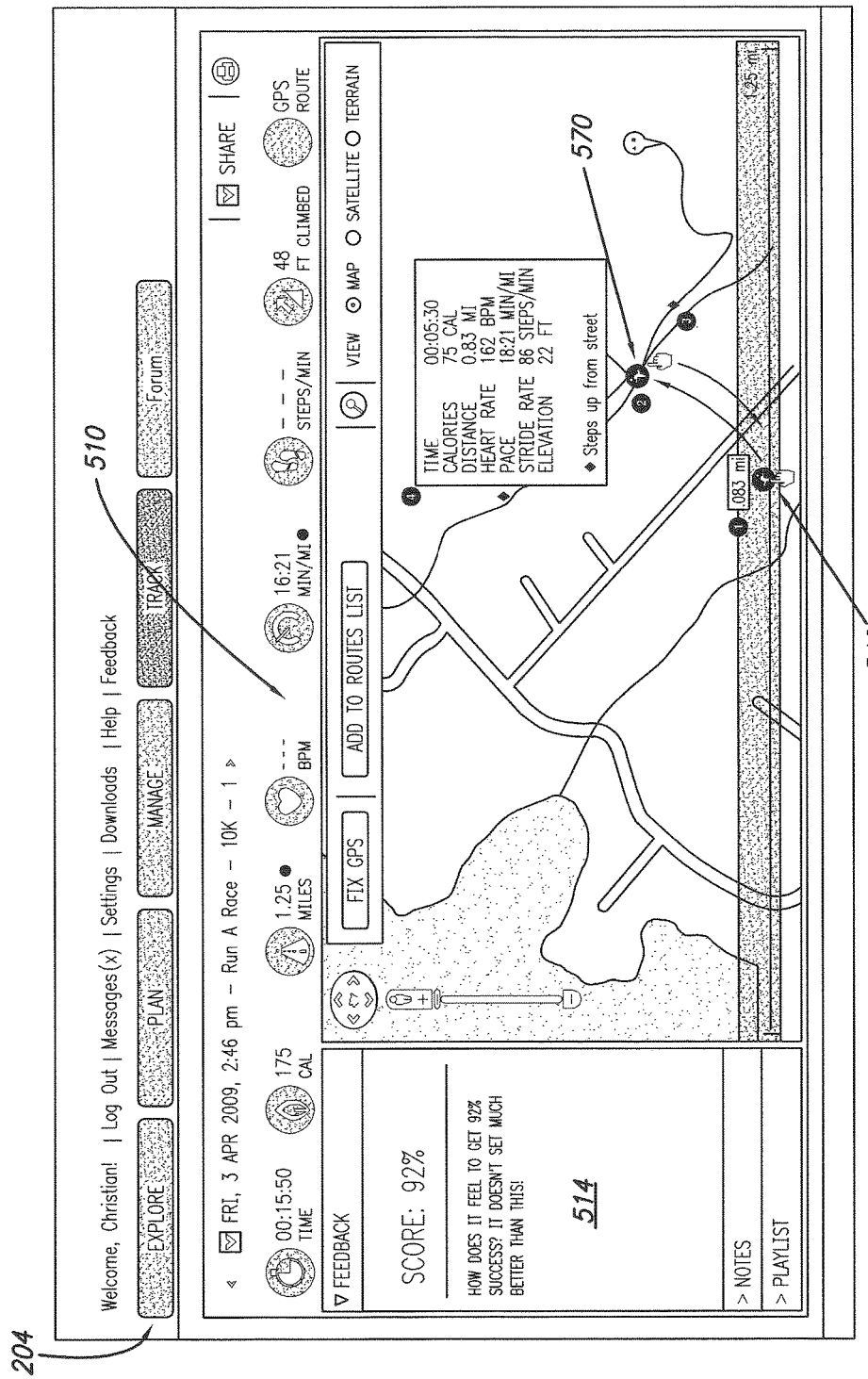
FIG. 45 is an exemplary GUI window according to an embodiment of the present invention.

In one embodiment, a user interested in viewing instantaneous performance statistics throughout the workout may be able to select and drag a scrollbar 542 with their cursor along the x-axis. As the user drags the scrollbar 542 across the x-axis, an icon 570 may travel along the route path plotted. In addition, a pop-up window displaying additional instantaneous performance data may appear and move across the screen along with the moving icon 570. FIG. 45 is an illustration of an icon 570 and pop-up window containing instantaneous performance parameter information being moved across a GUI screen by means of a scrollbar 542. Thus, scrollbar 542 may function in a similar way to scrollbar 516 described above. In an embodiment, the scrollbar 542 and/or the icon 570 may take the form of an active figure, such as a runner. In one embodiment, the user may be able to customize the images used for the scrollbar 542 and/or the icon 570 such as, for example, replacing the default icon with a personal avatar or other desired image.

Figure 46:
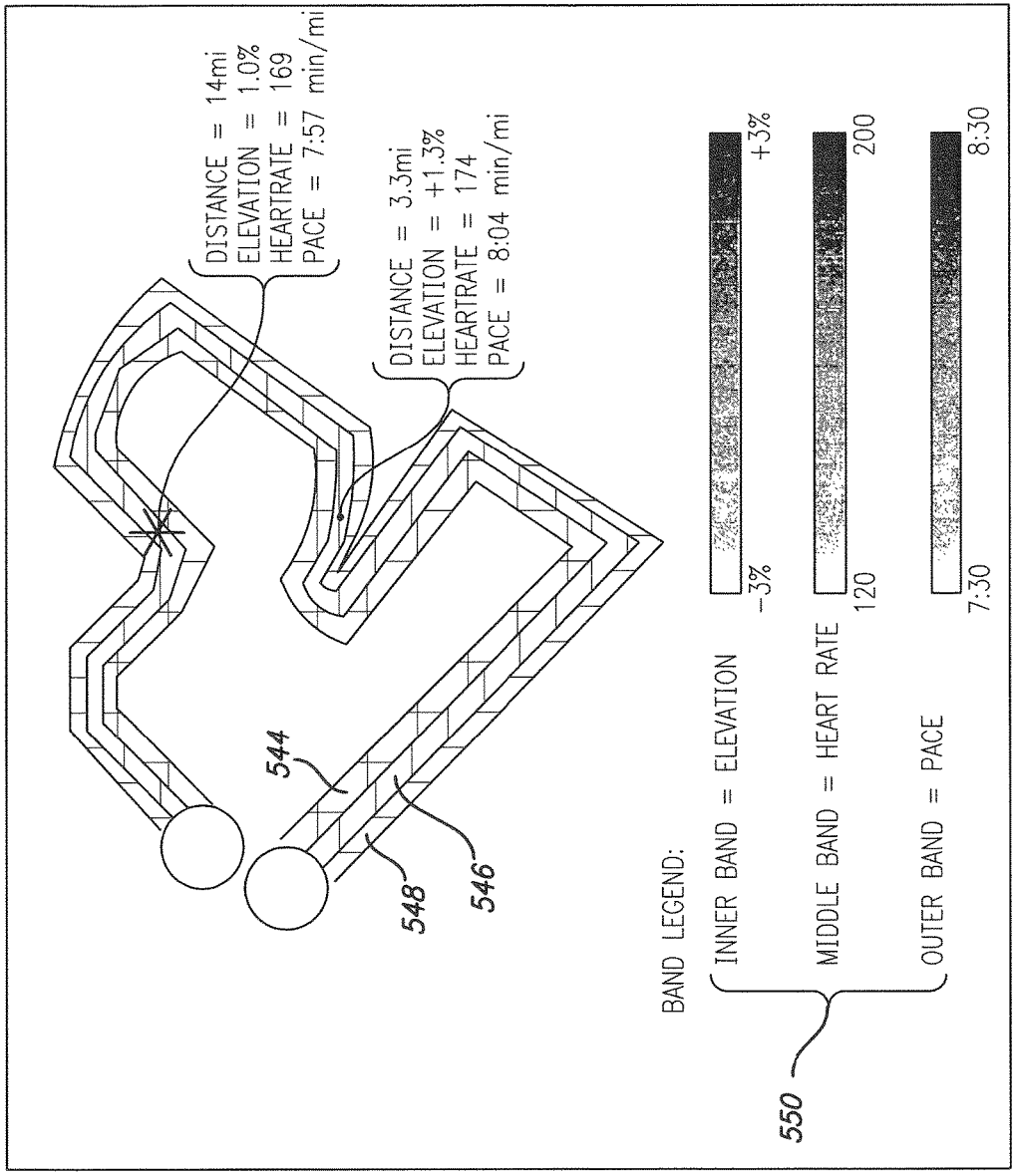
FIG. 46 is an exemplary GUI window according to an embodiment of the present invention.

As illustrated in FIG. 46, in another embodiment, the user may be provided with a route view in which multiple performance parameters are concurrently graphically presented in a banded format along a route path. Like the embodiments of FIGS. 44 and 45, the user's route path may be overlaid on a map, and performance parameters may be associated with particular points along the route. In contrast the embodiments of FIGS. 44 and 45, however, the route path may comprise a plurality of bands, each of which represents a performance parameter quantified at the GPS waypoints recorded along the route.

In an embodiment, the value of the respective performance parameter may be charted along route path utilizing color shade variation to represent the instantaneous quantity of the performance parameter at each point along the route. Thus, in FIG. 46, the different hatching applied to each of the inner band 544, middle band 546, and outer band 548 represents a different color and a varying spacing between the hatches represents the display of the colors at varying levels of intensity along the route path, depending upon the value of the parameters at each point along the path. The value associated with each shade of color is generally graphically represented in an accompanying legend 550.

In one embodiment, instantaneous performance parameter data at any point along the route path is presented in response to hovering over the point with a cursor, or in response to the user actuating a scrollbar, such as scrollbar 542 described above with respect to FIG. 45.

A user may be able to manually add markers to locations along the route path. In one embodiment, after the user adds two markers at two different locations along the route path, the user may be able to "lock" the markers. When markers are locked, actuating the scrollbar 542 may cause synchronized movement of the markers. "Synchronized movement" may refer to a situation where each of the markers advances a set number of GPS waypoints in response to a particular actuation of the scrollbar 542. In this manner, the user may be able to graphically and intuitively define an interval over which performance parameter information may be viewed. For example, a pop-up window displaying performance information corresponding to the interval defined by the two markers may appear and move across the screen along with the scrollbar 542.

In one embodiment of the present invention, the route map may display the location of annotations provided by the athlete 100 during the route, as previously described. Various icons or symbols corresponding to the locations of the annotations may be selected by the user. In the case of audio annotations, the user may click on or otherwise select an icon corresponding to the location of the audio annotation to play the audio annotation back to the user. Likewise, for photo- or video-based annotations, the user may click on or otherwise select the appropriate icon to play the video clip or display the photo.

In another embodiment, in addition to or instead of allowing athletes 100 to annotate a route during the activity, the user may be able to add annotations to the route while reviewing it after the activity has been completed. Based on the user's knowledge of the route, the user may add annotations corresponding to the locations of, for example, drinking fountains, bathrooms, or other interesting features along the route. These annotations may consist of text, symbols, audio recordings, video clips, and/or photos.

In an embodiment, the user may be able to manually correct any recorded GPS data that they know is inaccurate. Inaccuracies may be due to, for example, GPS receiver timing, positional, and/or other errors, such as those disclosed in commonly owned U.S. patent application Ser. No. 12/569,492, titled "Program Products, Methods, and Systems for Providing Location-Aware Fitness Monitoring Services," which is incorporated herein by reference in its entirety.

In embodiments where a predetermined route was assigned to the workout prior to undertaking the activity, as described above with reference to FIG. 16, the route module 1500 may have had access to an elevation database to obtain elevation corresponding to a particular route. This information may be used to supply elevation information for the route when conducting post-workout analysis. Accordingly, the elevation information supplied by the route module 1500 may be able to assist or replace any elevation information provided by positioning system receiver 126 of the portable fitness monitoring device 102. Thus, in the case of a GPS system, if less than four GPS satellites are acquired, or if the GPS receiver is not designed to process elevation information, the portable fitness monitoring device 102 can still determine elevation-dependent route and performance data regarding a route traversed by athlete 100. Even if the route module 1500 did not have had access to an elevation database prior to the workout, such a database may be accessed after the workout to supply the necessary information.

In another embodiment, the route tools sub-module of the application software may allow the athlete 100 to create, store, share, and find route plans of interest. The route plan, which may or may not be associated with a particular workout routine, may be created or selected that specifies a particular route for the athlete 100 to travel. In an embodiment, the route plan may be downloaded to the portable fitness monitoring device 102. Athletes 100 may use route plans they themselves have created and stored on the sever 112. In one embodiment, other users may post and share route plans with others via the server 112. Thus, a plurality of users 100 may be able to create, store, share, find, edit, rate, and comment on route plans of interest.

In one embodiment, the user may save and name a route or route plan using the route tools sub-module. In the embodiment of FIG. 44, as shown in the sidebar 514, the user has named and saved a plurality of routes or route plans to the server 112. In the event that a particular route or route plan has not been automatically assigned to a given workout record, the user may wish to select a route or route plan with the cursor to associate with their workout.

Saved routes or route plans may be displayed in primary display 512 if the user selects an appropriate icon. Route details such as the route name, distance, and location may be provided in a route details box 552 GUI pop-up window. The user may also be able to assign a subjective rating and include notes about the route. These features may be analogous to the user rating and user notes features described above.

While these route-related features have been described primarily in the context of presentation from the server 112 to a user stationed at a personal computer 114 such as a desktop or laptop computer, in an embodiment of the present invention, GUIs providing information and functionalities similar to those provided by the GUIs depicted in FIGS. 44-46 may be provided to the athlete 100 via the portable fitness monitoring device 102.

Figure 47A:
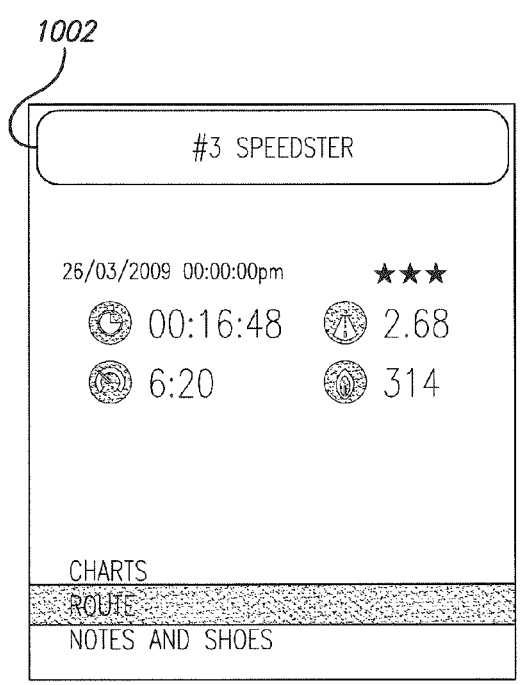
FIGS. 47A and 47B are exemplary GUI windows according to an embodiment of the present invention.

For example, FIG. 47A is an exemplary GUI window according to an embodiment of the present invention that may be displayed when the athlete 100 carrying a portable fitness monitoring device 102 selects an individual workout from a workout list, such as that depicted in FIG. 42A. As illustrated in FIG. 47A, a drop down menu may be provided that allows the athlete 100 to request additional information regarding routes.

Figure 47B:
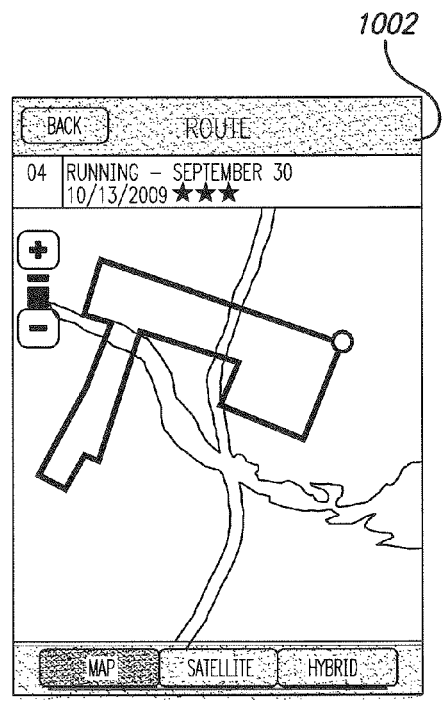

FIG. 47B illustrates an exemplary GUI window according to an embodiment of the present invention that may be displayed when the athlete 100 requests additional information regarding routes. The workout history sub-module of the track module 1200 may display a window including a depiction of the route traversed by the athlete 100 during the workout.

In one embodiment, a route map similar to that illustrated in FIG. 44 may be presented. In another embodiment, route map presented may convey information similar to that conveyed by the route map of FIG. 44, but the route map may be relatively less complex and more suitable for a smaller display screen of a portable fitness monitoring device 102.

In one embodiment, athletes 100 using portable fitness monitoring devices 102 may share routes directly between their devices 102 (i.e. not via the route selection feature of the website, as described above). For example, one athlete 100 may send a route to another athlete 100 via a text message or email message, regardless of the athletes' 100 locations. Alternatively, if the athletes 100 and their portable fitness monitoring devices 102 are in close proximity to one another, they may be able to share routes via WPAN transceivers and/or infrared transmission systems. Thus, an athlete 100 may share a favorite route with a friend.

Other route-related functionalities may be supported by the application software of the server 112 for use with the portable fitness monitoring services of the present invention. For example, in an embodiment, the portable fitness monitoring device 102 may be able to guide the athlete 100 along a route, based on the route plan and, for example, the athlete's 100 current position based on GPS readings. For example, as the athlete 100 is traversing a route, the portable fitness monitoring device 102 may audibly or visually command the athlete 100 to "turn right in 10 meters" or "turn right on Main St."

Figure 48:
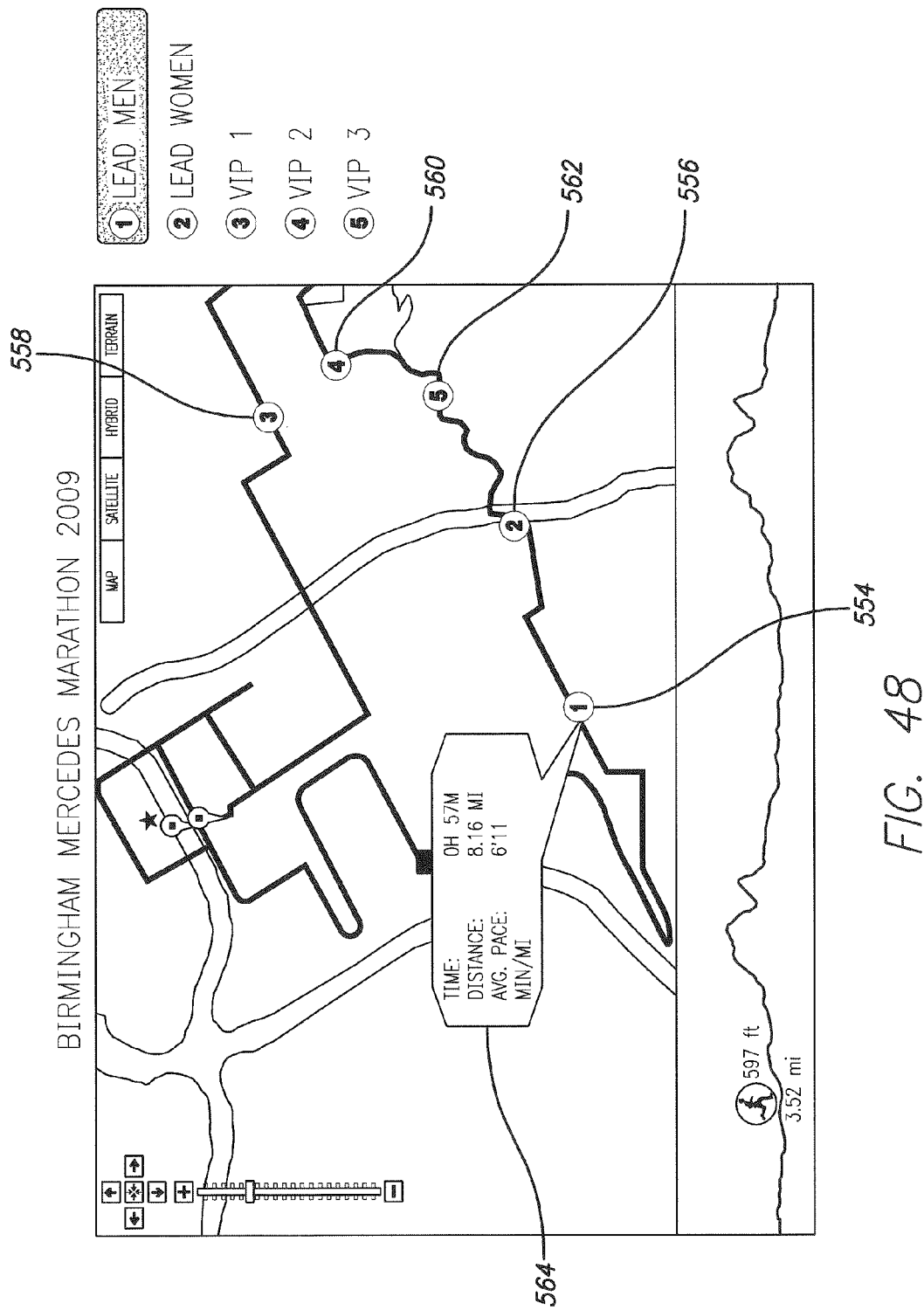
FIG. 48 is an exemplary GUI window according to an embodiment of the present invention.

In another embodiment, the route-related functionalities of the server 112 may be utilized to support the "live tracking" options described above. "Live tracking" refers to the ability of a remote user other than the athlete 100 to track the athlete's 100 location in substantially real time during the activity. As explained in further detail elsewhere, in an embodiment, the portable fitness monitoring device 102 may be able to wirelessly communicate location-based information to the server 112 via the network 110 in real-time via the WWAN 128 or WPAN 130 transceiver. Thus, users with access to this data on the server 112 may be able to view the athlete's 100 location, for example, superimposed on a map. In an embodiment, as depicted in FIG. 48, a plurality of athletes 100 competing in a race and each utilizing GPS-enabled portable fitness monitoring devices 102 may be tracked in substantially real-time and their positions (554, 556, 558, 560, and 562) may be superimposed over a route on a map. Users may be able to hover over or otherwise select an icon associated with a particular athlete, such as icon 554, and display an information box 564 that displays current performance parameter information for that athlete 100.

Returning to the presentation of information from the server 112 to a user stationed at a personal computer 114 such as a desktop, laptop, or tablet computer, in an embodiment of the present invention, summary information about the athlete's 100 workouts and training program may be presented to the user.

Figure 49:
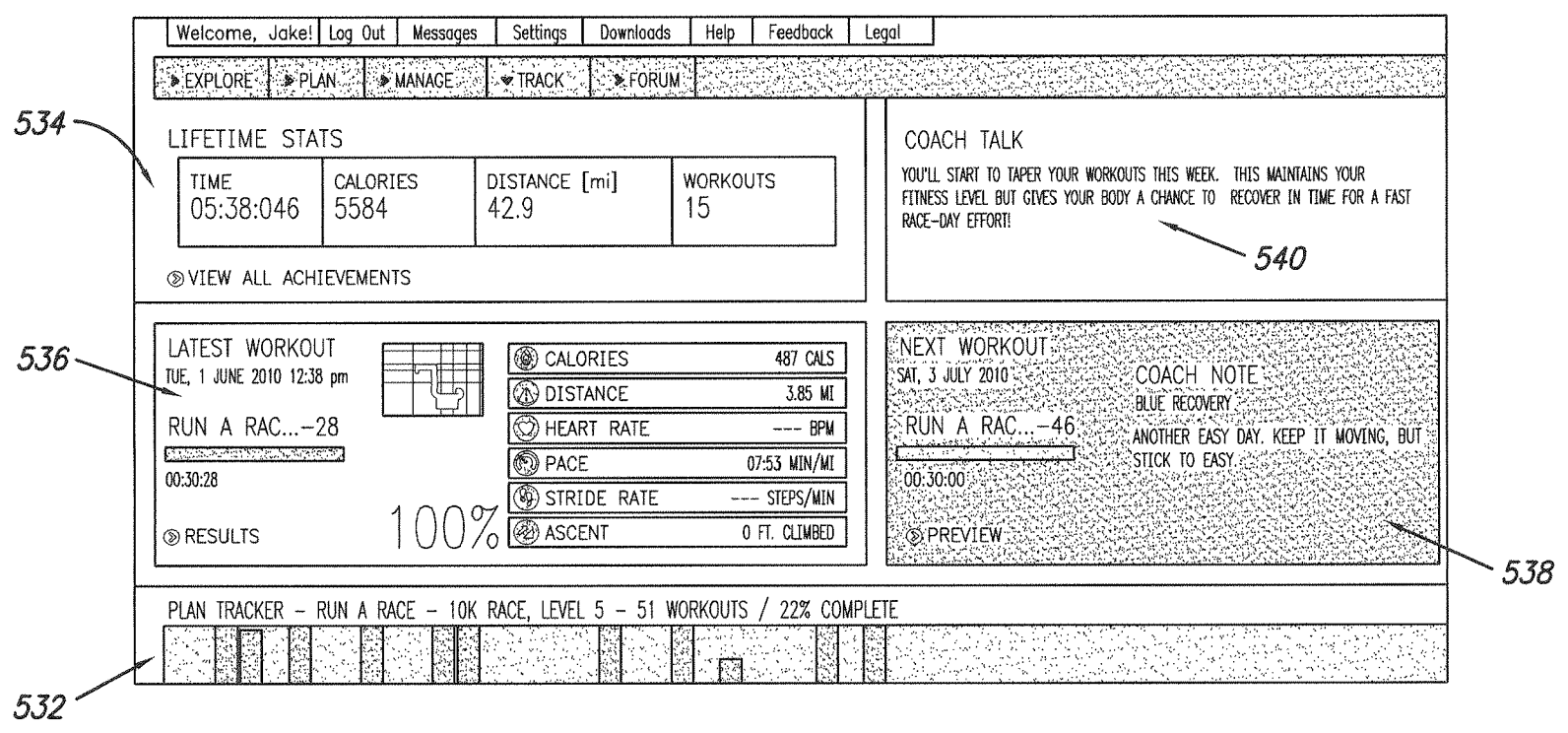

More specifically, the track module 500 of the application software of the server 112 may provide a front page sub-module. FIG. 49 is an exemplary GUI window that may be displayed by the front page sub-module to a user stationed at a personal computer 114. The front page GUI may include plan tracker 532, lifetime stats 534, last workout 536, next workout 538, and coach talk 540 sections. In an embodiment, the contents of the front page may be customized and reordered similarly to customizable web portals such as, for example, the iGoogle web portal.

The lifetime stats section 534 may provide text and/or icons that are correlated to particular cumulative or average lifetime performance parameters. In this way information displayed by the lifetime stats section 534 on the front page may be somewhat similar to information displayed by the dashboard 510 of the other history pages. The particular information displayed in the lifetime stats section 534 may be set by the system or customized by the user. Various information may be added or removed by the user as desired.

In an embodiment, the last workout section 536 displays stats for the last workout completed by the athlete 100, and the next workout section 538 displays information about upcoming planned workouts. The information provided by the lifetime stats 534, last workout 536, and next workout 538 sections may be similar to information provided to the user by other modules and sub-modules, but may conveniently be provided on a single page. The coach talk section 540 may provide motivation, point out a particular area of focus, or otherwise provide guidance to the athlete 100 related to the ultimate goal of their particular plan or workout.

In one embodiment, the front page includes a plan tracker 532 section. The plan tracker 532 may graphically display an athlete's 100 planned workouts, the number of planned workouts completed, and the number of planned workouts remaining to be completed. For example, as shown in FIG. 49, the plan tracker 532 could include a series of icons or hash marks that are each representative of an individual workout. Completed, and uncompleted workouts maybe differentiated by color-coding, shading, or other visual indicia. The plan tracker 532 may provide indication(s) about whether the athlete 100 is meeting the specified goals for the completed workouts.

The particular information displayed in the plan tracker 532 section may be set by the system or customized by the user. Various information may be added or removed by the user as desired. An athlete 100 engaged in multiple plans simultaneously (e.g. a running based plan and a non-running based plan) may choose to display multiple plan trackers 532 at once. In an embodiment, other trackers may be provided that display information similarly to the plan tracker 532. For example, an athlete 100 with a goal to lose weight may chose to display a weight tracker that tracks their progress towards a weight loss goal.

While these workout summary features have been described primarily in the context of presentation from the server 112 to a user stationed at a personal computer 114 such as a desktop, laptop, or tablet computer, in an embodiment of the present invention, GUIs providing information and functionalities similar to those provided by the GUIs depicted in FIG. 49 may be provided to the athlete 100 via the portable fitness monitoring device 102. In another embodiment, rewards awards, achievements, and/or advertisements may also be provided.

As explained above, the track module 1200 of the application software may include an achievements sub-module. As explained in further detail below, certain aspects of the achievements sub-module of the track module 1200 of the portable fitness monitoring device 102 may be similar to aspects of the front page sub-module of the track module 500 of the server 112, as described above.

Figures 50A, 50B:
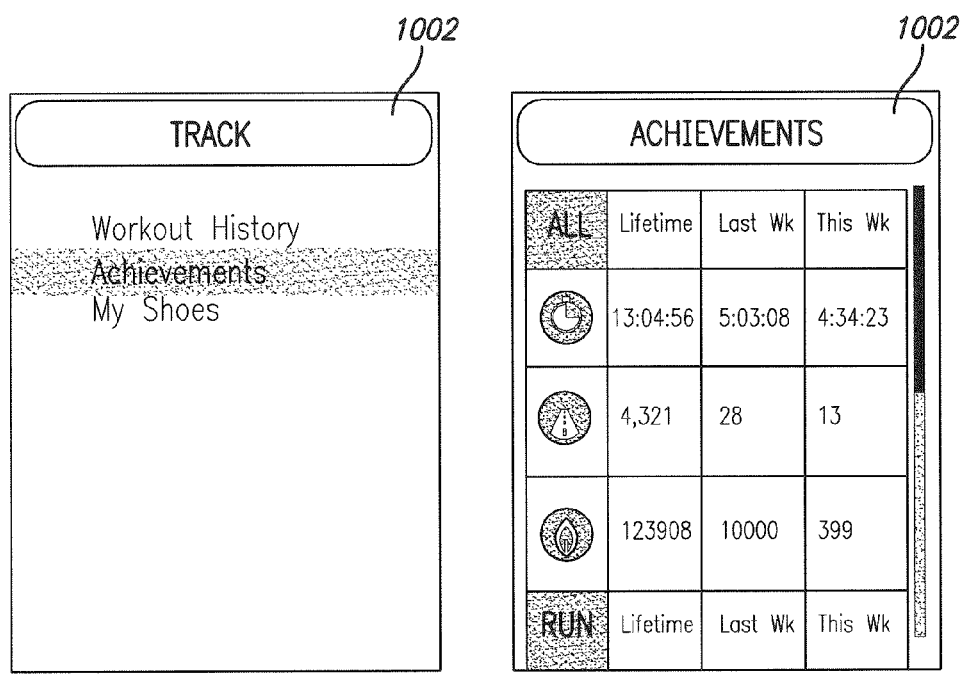
FIGS. 50A and 50B are exemplary GUI windows according to an embodiment of the present invention.

As explained above, in one embodiment, the track module 1200 may present the athlete 100 with the option of receiving additional information regarding workout histories, achievements, or shoes, as illustrated in FIG. 50A. When the athlete 100 indicates that they would like to receive additional information regarding achievements, the workout history sub-module may present a GUI such as the exemplary GUI window shown in FIG. 50B.

In one embodiment, summary information similar to that illustrated in FIG. 49 may be presented at the portable fitness monitoring device 102. In another embodiment, summary information presented may convey information similar to that conveyed by the FIG. 49, but the summary information may be relatively less complex and more suitable for a smaller display screen of a portable fitness monitoring device 102. As illustrated in FIG. 50B, in one embodiment, the a display similar to the lifetime stats section 534 discussed above may be presented on the portable fitness monitoring device 102.

As explained above, the track module 1200 may further include a shoes sub-module. Using this sub-module, the athlete 100 may be able to associate a particular pair of shoes that the athlete 100 wore during the workout with the workout.

In one embodiment, after an appropriate prompt from the track module 1200, the athlete 100 may manually associate a particular pair of shoes with the workout using the user interface controls 124 of the portable fitness monitoring device 102. In another embodiment, the portable fitness monitoring device 102 may be able to automatically detect which pair of shoes were being worn during the activity by detecting the presence of a specific identifier, such as a radio frequency identification (RFID) chip in one or both of the shoes, as described in further detail above.

In an embodiment where the athlete 100 manually enters information about their shoes into the system, the athlete 100 may be prompted to enter the shoe brand and style. Options for brand names and styles may be provided in a drop-down menu. The athlete 100 may further be prompted to enter a nickname for the pair of shoes, and may be asked to estimate how many miles (or kilometers) they have already covered while wearing the shoes. In another embodiment, this information may be detected automatically.

At a later time, a listing of each pair of shoes the athlete 100 has associated with one or more workouts, along with a cumulative distance that the athlete 100 has traversed while wearing each pair of shoes, may be presented. Athletes 100 may advantageously use this information to determine when a particular pair may need to be replaced, or to determine how particular pairs of shoes have affected the athlete's 100 performance.

In one embodiment of the present invention, when the athlete 100 logs a predetermined number of miles (or kilometers) in a pair of shoes, the server 112 may send a message to the athlete 10 to suggest that the athlete 100 purchase a replacement pair of shoes. The message may provide information about the effects of wear on the performance of shoes. The message may be, for example, a text message, an email, or post to the athlete's social networking site page. The message may also suggest a particular pair of shoes to the athlete. In an embodiment, the message may provide a link to an online retailer's website where the athlete 100 could purchase the suggested pair of shoes, and may provide the athlete with a coupon toward the purchase of the new pair of shoes.

F. OTHER FEATURES

According to some embodiments of the present invention, users may interact with the portable fitness monitoring device 102 and/or the computer server 112 system before, during, and/or after the physical activity in various other ways while utilizing the fitness monitoring services of the present invention.

As explained above, in one embodiment, the application software of the server 112 includes a library module 700 and a forum module 800. Accordingly, the menu bar 204 of certain GUI windows may include several icons or indicia corresponding to the library 700 and forum 800 modules. While the description that follows primarily describes the presentation of library and forum information in the context of presentation from the server 112 to a user stationed at a personal computer 114 such as a desktop, laptop, or tablet computer, information may also be presented via the portable fitness monitoring device 102 itself to the athlete 100.

The library module 700 may be capable of displaying GUI windows for photos, illustrations, videos and articles. The photos, illustrations, videos and articles may provide the athlete 100 with additional resources for planning, preparing for, and executing their workouts.

The library module 700 may include a videos section that provides short animations and/or videos teaching the athlete 100 proper stretching, warm-up, cool-down, and other exercising techniques. The athlete 100 may select a video icon with a cursor to display the video. A pop-up window may appear in response to the athlete 100 selecting a particular video. The pop-up window may include the animation and/or video, a suggested number of repetitions or time period for the activity, and other notes or comments about the activity. Additionally or alternatively, the pop-up window may include a photo, illustration, or other image that relates to the activity.

In an embodiment, the athlete 100 may be able to download videos from the server 112 to a portable fitness monitoring device 102 having a video screen so that they may be viewed remotely. This may allow the athlete 100 to view instructions regarding preparing for or executing their workouts at the site of their workout prior to or during their exercise routine.

The library module 700 may include an articles section that provides articles information the athlete 100 about various health and fitness topics. Articles may focus on topics such as strength training, cardiovascular exercise, biking, running, inline skating, golfing, or a variety of other topics. The articles may not all relate directly to fitness activities. For example, some articles may be related to diet and nutrition.

The forum module 800 may be capable of displaying GUI windows for user forums. In one embodiment, the forum module 800 may employ a social networking application, such as, for example, Facebook or Twitter. The social networking application may utilize an application programming interface that allows the social networking application, such as Facebook or Twitter, to be embedded into the GUI windows of the present invention. In another embodiment, the social networking site provides a feed that can be transmitted and displayed via the GUI windows of the present invention.

The forum page may be a place where users can exchange updates regarding their fitness planning and progress using the system of the present invention. Users may also exchange information regarding the website, the particular training equipment and devices they are using, the athletic events or races they are participating in, and information giving and/or requesting coaching or other advice.

While library and forum have been described primarily in the context of presentation from the server 112 to a user stationed at a personal computer 114 such as a desktop, laptop, or tablet computer, in an embodiment of the present invention, GUIs providing information and functionalities similar to those provided by at a personal computer 114 may be provided to the athlete 100 via the portable fitness monitoring device 102. For example, the explore module 1300 of the application software of the portable fitness monitoring device 102 may be capable of providing such features.

As described in detail above, a user stationed at the remotely located personal computer 114 may be able to use a website to plan and schedule a prospective physical activity. In one embodiment of the present invention, the website may enable a user who is a coach to provide training information, guidance, and/or feedback to one or more athletes 100.

As illustrated in FIG. 8, the application software of server 112 may include a coaching group module 1600. Among other things, the coaching group module 1600 may support one or more GUIs that are capable of being presented to coaches and/or athletes 100 at personal computers 114 and/or portable fitness monitoring devices 102.

Coaches and/or athletes 100 may be able to utilize certain features supported by the coaching group module 1600 by accessing a fitness monitoring service website provided by the server 112, as described in detail elsewhere. Upon accessing the website, a coach and/or athlete may login to an account of the fitness monitoring service provided by the server 112.

In one embodiment of the present invention, a user-coach may have previously created and logged into a stand-alone coaching account. The stand-alone coaching account may enable the user-coach to utilize certain coaching features, as described in further detail below, but may not allow the user-coach to utilize one or more of the fitness monitoring features described above (e.g. the user-coach may not be able to monitor and analyze their own fitness and workouts using the stand-alone coaching account).

In another embodiment, upon accessing the website, the user-coach may log into their general account that allows the user-coach to utilize one or more of the fitness monitoring features described above (e.g. the user-coach may be able to monitor and analyze their own fitness and workouts using the general account). In this case, while logged into their general account, the user-coach may be able to create a coaching account that is part of their general account. For example, in an embodiment, a menu bar 204, such as that depicted in FIG. 9, may include an icon or indicum corresponding to the coaching group module 1600. Upon selecting this icon or indicium, the user-coach may be prompted to create a coaching account.

Once the user-coach has logged into their coaching account, the coaching group module 1600 of the application software may present the user-coach with a GUI that allows the user-coach to create coaching group. A coaching group may be a group of linked accounts of the fitness monitoring service where one user—the coach—is responsible for providing training information, guidance, and/or feedback to one or more other users—the athletes 100. Athletes 100 in a coaching group may conduct activities using portable fitness monitoring devices 102 that are capable of communicating information with a sever 112 that provides fitness monitoring services, as described above. Features of the coaching group may implemented and provided by a website, as described in further detail below.

When creating the coaching group, the coach may be prompted to determine certain parameters for the group. For example, in one embodiment, the coach may name the coaching group and provide a brief description of the goals for members of the group. In another embodiment, the coach may limit members of the group to, for example, members who live in a certain geographical area, belong to a certain athletic club or sports team, are in a certain age range, or have certain other common interests or characteristics.

When the coach creates a coaching group, the menu bar 204 may be updated to include an icon corresponding to the coaching group. The coach may then select the coaching group icon to access certain features of the coaching group described below.

In one embodiment, athletes 100 may join the coaching group after receiving an invitation, such as an invitation from the coach or from an existing member-athlete 100 of the coaching group. In another embodiment, the coaching group module 1600 may provide a search feature on the website so that athletes 100 may search for a coaching group that they may like to join. The coach may be able to control the ability of athletes 100 to search for and find their coaching group by deciding whether to publish their coaching group to the general user community of the fitness monitoring service.

When an athlete 100 joins a coaching group (after requesting to join the group and/or after accepting an invitation to join the group), the athlete's 100 general fitness monitoring account may be linked to the coach's coaching account. If the athlete 100 does not already have a fitness monitoring account, the athlete may be prompted to open one. Once the coach's and athlete's 100 accounts are linked, a menu bar 204 that may be displayed as part of the GUI of the athlete's account may be updated to include an icon corresponding to the coaching group. The athlete 100 may then select the coaching group icon to access certain features of the coaching group described below.

At any time after the coach's and athlete's 100 accounts are linked, the coach may be able to remove an athlete 100 from the coaching group, thus un-linking their accounts. Similarly, at any time the athlete 100 maybe able to quit the coaching group, thus un-linking the athlete's and coach's accounts.

Figure 51:
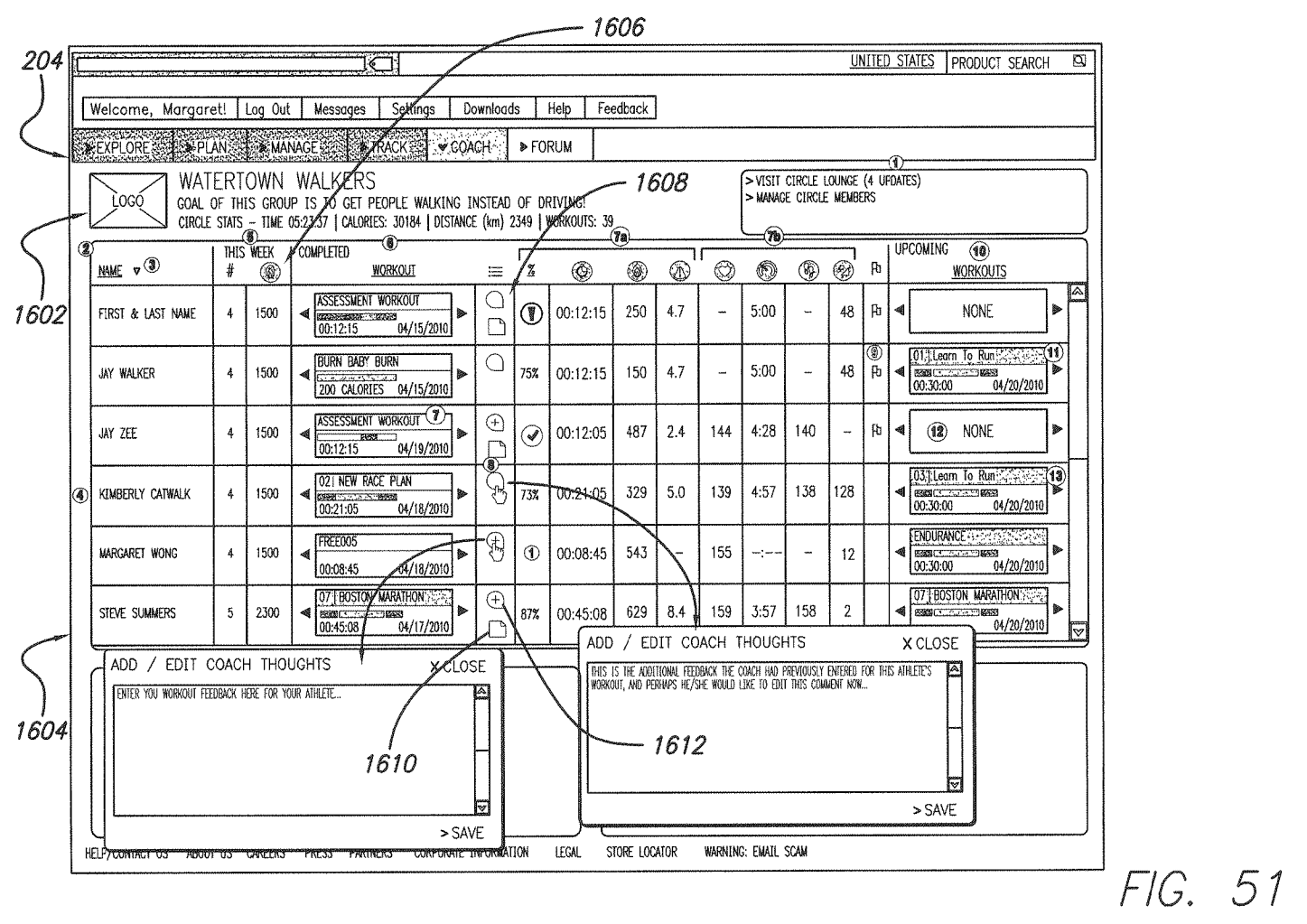

The coach may select the coaching group icon to access certain features of the coaching group described below. FIG. 51 is an exemplary GUI window that may be displayed to the coach by the coaching group module 1600. This GUI window may display a coaching dashboard that includes a variety of information about the coaching group, its members, and their performance.

As shown in FIG. 51, the coaching dashboard may include a header 1602 and a member information section 1604. The header 1602 may include a coaching group name and description. For example, the group "Watertown Walkers" may have a stated goal of getting people of the city of Watertown to walk more instead of driving. The header 1602 may also include a total stats line that provides cumulative statistical totals for all members of the coaching group. For example, as illustrated in FIG. 51, the Watertown Walkers have collectively been active for a total of 5 days, 23 hours, and 37 seconds, have burned 30,184 calories, have covered 2,349 kilometers, and have conducted a total of 39 individual workouts. In this way, the statistical group information provided by the header 1602 may be similar to the achievement information provided to an individual athlete 100, as described above with respect to FIGS. 49 and 50.

The member information section 1604 may include a table that lists the names of the member-athletes 100 in rows and provides categories for scheduling and/or performance information associated with the athletes 100 in columns. For example, as illustrated in FIG. 51, for a given athlete 100, the table may provide the athlete's 100 name, a snapshot 1606 of their performance for the current week, information regarding the last workout the athlete completed, and information about the next workout that the athlete 100 has scheduled.

In one embodiment, as illustrated in FIG. 51, the snapshot 1606 may list the number of workouts the athlete 100 has completed and the number of calories the athlete 100 has burned in the current week. In other embodiments, weekly totals or averages for other performance information categories, such as those described below, may be provided by the snapshot 1606. For example, in an embodiment, the athlete's 100 average pace, speed, or heart rate for the current week may be provided.

Information regarding the last workout the athlete completed may include the name or type of workout completed (e.g. plan workout, custom workout, free workout, or assessment workout), the date the workout was completed, and/or the total workout time. A zone bar indicator 320, such as those described above and those depicted in FIG. 51, may also be provided. Other information regarding the last workout provided by the coaching group module 1600 may also include, for example, the elapsed time of the workout, the calories the athlete 100 burned during the workout, the distance traveled during the workout, the athlete's 100 average heart rate during the workout, the athlete's average pace during the workout, the athlete's 100 average stride rate during the workout, and the degree of the athlete's 100 elevational ascent during the workout. Each time the coach accesses the coaching dashboard, the dashboard may sync with the member-athlete's 100 accounts so that all of the data provided in the member information section 1604 is up to date.

In one embodiment of the present invention, a feedback column 1608 may provided a place where icons may be displayed to indicate that the athlete 100 or the coach has provided notes or other feedback about a workout. For example, as illustrated by FIG. 51, a note icon 1610 may indicate that the athlete 100 has provided a note for the workout, as described above with reference to FIGS. 33C, 33D. As further illustrated by FIG. 51, a feedback icon 1612 may indicate that the coach has provided feedback regarding the workout. The feedback associated with the feedback icon 1612 may be, for example, a congratulatory or critical comment on the athlete's 100 performance during the workout. In an embodiment, the coach may provide feedback to the athlete by, for example, a text message, an email message, or post to the athlete's 100 social networking site page, and a feedback icon 1612 may appear on the dashboard in the feedback column 1608 in response to this.

The member information section 1604 table may also include information about the next workout that the athlete 100 has scheduled. Information regarding the next workout the athlete 100 has scheduled may include the name or type of workout to be completed (e.g. plan workout, custom workout, free workout, or assessment workout), the date the workout is scheduled to be completed, and/or the total estimated workout time. A zone bar indicator 320, such as those described above and those depicted in FIG. 51, may also be provided.

In one embodiment, in response to the coach clicking on one of the various graphical elements of the dashboard, the coaching group module 1600 may provide the coach with a GUI that includes more detailed information about an individual athlete's 100 workout, such as a GUI similar to those capable of being provided by the history sub-module of the track module 500, as depicted in FIGS. 36-40. In this way, the coach may review and analyze the athlete's workout performance in greater detail. In an embodiment, the athlete 100 may adjust their coaching group setting so that the coach has limited access to certain portions of their athletic performance data.

In another embodiment, in response to the coach clicking on, for example, the athlete's 100 name or an icon corresponding to the athlete's 100 next scheduled workout, the coaching group module 1600 may provide the coach with a GUI that includes a calendar 402 of the athlete's 100 scheduled workouts, such as a GUI similar to those capable of being provided by the schedule module 400, as depicted in FIG. 14.

With regard to the planning and scheduling aspects of the coaching group features of embodiments of the present invention, a coach may have different levels of involvement in the providing workouts for the member-athletes 100.

In one embodiment, the coach may have the authority to select a training plan and schedule the plan workouts of the training plan on the athlete's 100 calendar, as described above with respect to FIGS. 12-14. In another embodiment of the present invention, the coach may have the authority to build, select, and/or schedule custom workouts on the athlete's 100 calendar, as described above with respect to FIG. 14.

Workout routines associated with the scheduled workouts may be sent to the athlete's 100 portable fitness monitoring device 102 prior to the athlete 100 engaging in the workout, as described above.

As a specific example of an embodiment of the present invention, an athlete 100 may be granted access to a general account with the fitness monitoring service described above. Among other things, the fitness monitoring service may be capable of maintaining a schedule of workouts for the athlete 100 to complete in association with the account. This may be accomplished, for example using the plan module 300 and schedule module 400 software application modules, as described above.

The athlete 100 may chose to join a coaching group that was set up by a coach in the coaches own account utilizing the coaching group module. Once the coach and athlete's 100 accounts are linked, the coach may be able to provide a new workout for the athlete 100. When the system receives that new workout from the coach, the new workout may be added to the schedule of the athlete's 100 workouts. Then, at the appropriate time, a workout routine corresponding to the new workout may be sent to the athlete's 100 portable fitness monitoring device 102, such as a mobile phone. After the athlete 100 completes the workout, the portable fitness monitoring device 102 may send athletic performance information associated with the workout back to the server 112 for additional processing.

In one embodiment, the coach may be able to provide the new workout for the athlete 100 by interacting with a GUI that includes a graphical representation of the athlete's 100 schedule of workouts, such as a workout calendar 402. The coach may associate the new workout with particular day on the athlete's 100 calendar. For example, in an embodiment, the coach may select an icon corresponding to a custom workout from a GUI sidebar 514 and drag the custom workout icon to another icon representing a particular day on the calendar 402. The system thus schedules the new workout on the athlete's 100 calendar for the athlete 100 to complete at a later date.

As described in detail above, the new workout may have a performance parameter target such as, for example, a target time, distance, speed, pace, and/or heart rate. The workout may consist of a series of intervals each having a target intensity, such a target speed, pace, and/or heart rate. In an embodiment, as described above, the target intensity may be a range of intensities or a zone, such as the color-coded zones described above with reference to FIGS. 10 and 11.

As described in detail above, in one embodiment of the present invention, the fitness monitoring system may utilize an "assessment workout" to assess the relative fitness level of the athlete 100, and/or to establish or modify the athlete's 100 performance zones for one or more parameters. This feature may be enabled by the go module 1100 of the portable fitness monitoring device and/or the support module 600 of the server 112.

As illustrated in FIG. 8, the application software of server 112 may include an assessment workout module 1700. Among other things, the assessment workout module 1700 may be capable of generating workout routines for athletes 100 who have not yet created an account with the fitness monitoring service.

An athlete 100 who possesses a portable fitness monitoring device 102, such as a mobile phone, may be interested in testing out fitness monitoring services, such as those described according to embodiments of the present invention. However, the athlete 100 may be reluctant to sign up for an account with the fitness monitoring service via a website. In an embodiment of the present invention, an athlete 100 with a compatible portable fitness monitoring device 102, such as a mobile phone, may be able to test out the portable fitness monitoring service by utilizing their portable fitness monitoring device 102 and providing the fitness monitoring service with minimal information, but without initially creating an account with the fitness monitoring service.

In one embodiment, the athlete 100 may power on their portable fitness monitoring device 102 if it is not already in a powered on state. In some embodiments, it may be necessary for the athlete 100 to manipulate user input controls 124 to enter a portable fitness monitoring mode to access the application software. In other embodiments, it may be necessary for the athlete 100 to download the application software.

Upon launch of the portable fitness monitoring application, the start module 1000 may prompt the athlete 100 and determine whether the athlete 100 wishes to proceed as a guest who does not have an account with the fitness monitoring service. If the athlete 100 indicates via activation of the user input controls 124 that the athlete 100 does not have and/or does not want to create an account with the fitness monitoring service, the start module 1000 may present a personal information wizard that may allow the athlete 100 to enter personal information such as, for example, the athlete's 100 age, the athlete's 100 gender, the athlete's 100 weight, and/or the athlete's 100 height. As explained in further detail above, the personal information wizard may also allow the athlete 100 to enter preferred unit preferences and/or preferred voice training options.

As described above with respect to FIG. 26, in an embodiment, the portable fitness monitoring device 102 may provide the athlete 100 with instructions for conducting the assessment workout, may begin the assessment workout, may monitor the athlete's 100 performance, and may end the assessment workout.

For example, verbal or visual instructions may be provided to the athlete 100 that tell the athlete 100 to run as fast as possible for two minutes. During the two minute activity, the portable fitness monitoring device 102 may measure and record performance information associated with the athlete 100 such as, for example, the athlete's 100 heart rate and/or speed. In an embodiment, the portable fitness monitoring device 102 may measure and record the athlete's 100 maximum heart rate and/or maximum speed during the activity.

Alternatively, the assessment workout may prompt the athlete 100 to, for example, run at certain percentages of their maximum speed for set periods of time, as subjectively estimated by the athlete 100. For example, the assessment workout may prompt the athlete 100 to try to consistently run at 50%, 75%, and 100% of their maximum speed for consecutive 1 minute periods. During this three minute activity, the portable fitness monitoring device 102 may measure and record performance information associated with the athlete 100 such as, for example, the athlete's 100 heart rate and/or speed.

Upon completion of the specified activity, the portable fitness monitoring device 102 may transmit the performance information to the fitness monitoring service server 112, as described in further detail elsewhere. Either before, along with, or after the transmission of the performance information from the portable fitness monitoring device 102 to the server, the athlete's 100 personal information may also be transmitted to the server 112.

Figure 52:
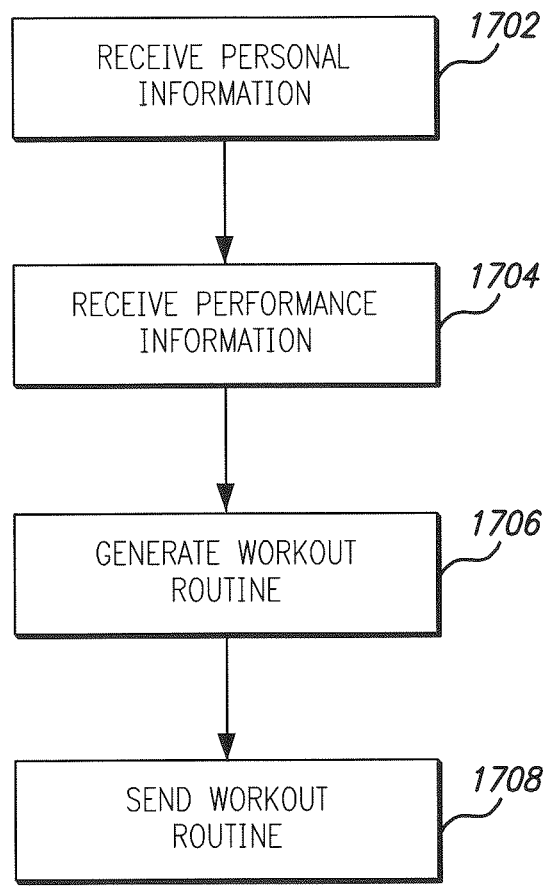
FIG. 52 is a flow chart outlining actions capable of being initiated by software according to an embodiment of the present invention.

The assessment workout module 1700 of the application software of server 112 may be capable of initiating several related actions, as briefly outlined in the flow chart of FIG. 52. At step 1702, the server 112 may receive the personal information associated with an athlete 100 from the portable fitness monitoring device 102. Before, along with, or after step 1702, at step 1704, the server 112 may also receive the performance information associated with the athlete 100 from the portable fitness monitoring device 102. Next, at step 1706, the workout module 1700 may generate a workout routine based on the personal information and the performance information. Finally, at step 1708, the server 112 may send the workout routine to the portable fitness monitoring device 102.

The workout module 1700 may be able to generate a workout routine using one of a variety of algorithms. In one embodiment, one or more of the athlete's 100 age, gender, weight, and/or height may be factored in to increase or decrease the difficulty of the workout routine. In another embodiment, the athlete's 100 heart rate, pace, and/or speed information may be factored in to increase or decrease the difficulty of the workout routine. In some embodiments, look-up tables or performance parameter indices may be consulted.

Other factors may also go into the generation of a workout routine. In one embodiment, the weather forecast for the region where the athlete is located or otherwise desires to conduct a workout could be factored in. For example, if the forecast calls for very hot weather, the intensity of the workout generated may be lowered. In another embodiment, the athlete could indicate that they are training for an upcoming event, such as a specific race. Accordingly, the characteristics of the race route (e.g. distance, elevation, difficulty, etc.) could be factored in to the generation of the workout routine.

In yet another embodiment, to encourage the athlete 100 to continue using the fitness monitoring in the future, along with the workout routine, the athlete 100 may be provided with specific training tips and/or contact information for local trainers or coaches in the athlete's 100 area.

The workout routine may include one or more of a number of different goals, as described with respect to plan and custom workouts elsewhere. For example, the workout module 1700 may be able to generate a workout routine that includes a target time or a target distance. The workout module 1700 may also be able to generate a workout routine that includes a plurality of intervals, where each interval has an intensity goal. The workout module 1700 may further be able to generate a workout routine where the intensity goal is, for example, heart rate, distance, pace, or speed based.

In an embodiment, the portable fitness monitoring device 102 and the server 112 may communicate information via a wireless network, as described above. For example, in one embodiment, the portable fitness monitoring device 102 is adapted to transmit personal and performance information and to receive the workout routine using a wireless transceiver, as described above.

In a further embodiment, the workout module 1700 may be capable of generating a workout based on the user's present location and/or the weather conditions or forecast associated with the user's present or desired location. Location-based information may be determined based on position information derived from a positioning system receiver 126 of the portable fitness monitoring device 102, as described above.

In some embodiments, the workout module 1700 may generate multiple workout routines for an athlete 100 based on a single assessment workout.

As described in detail above, in one embodiment of the present invention, the portable fitness monitoring device 102 may include or communicate with one or more sensors 104 for detecting information used to measure and/or calculate performance parameters. In an embodiment shown in FIG. 1, the portable fitness monitoring device 102 itself may include a sensor 104.

In one embodiment, a positioning system receiver 126, such as that illustrated in FIG. 3, may function as a sensor 104 integrally coupled to the portable fitness monitoring device 102, and may allow the portable fitness monitoring device 102 to detecting information that may be used to measure and/or calculate location, distance traveled, speed, and/or pace. The positioning system receiver 126 may be, for example, a GPS- or Galileo-compatible receiver.

As the portable fitness monitoring device 102 including the positioning system receiver 126 is supported by the athlete 100 during an activity, the positioning system receiver 126 may receive positioning system signals from positioning system satellites, where each positioning system signal may contain a timestamp. From these positioning system signals, the processor 120 of the portable fitness monitoring device 102 may compute a series of time-stamped position points. These time-stamped position points may be subject to at least two types of error, namely, timing error and positional error.

Timing error may be induced by a low performance processor driving the positioning system receiver 126 that does not have sufficient cycles to dedicate to positioning system signal processing. Alternatively or additionally, timing error may be inserted by the use of, for example, assisted GPS (A-GPS), which requires round trip communication over a wireless network to validate a GPS reading, or by local filtering performed by the positioning system receiver 126 and/or the processor 120.

Additional positional error may also be caused by the inherent positional error of commercial (as opposed to military) positioning system signals, which, in the case of GPS, is typically between 3-5 meters. Consequently, when the sampling rate of the positioning system signal causes more than one sample to be taken during time interval required for the athlete 100 to traverse the positional error distance, a "zigzag" positional route may be reported even if a relatively straight path was followed. This distance error may negatively impact any average or instantaneous speed or pace computations that depend on a correct reporting of distance traversed.

Accordingly, positioning system-based speed or pace calculations may be prone to these and other errors. In embodiments of the present invention that rely on positioning system-based speed or pace calculations to provide real-time coaching and/or feedback, as described above, these errors can adversely affect the accuracy of the coaching and/or feedback. For example, some embodiments may provide feedback when the athlete 100 has fallen outside of a desired speed or pace zone. If the portable fitness monitoring device can not accurately detect changes in speed or pace, this feedback may be inaccurate.

As illustrated in FIG. 21, the application software of the portable fitness monitoring device 102 may include a positioning system smoothing module 1800. Among other things, the positioning system smoothing module 1800 may be capable of increasing the accuracy of positioning system-based speed or pace detection and, therefore, the accuracy of the real-time coaching and/or feedback.

In one embodiment of the present invention, the positioning system smoothing module 1800 may employ a buffer system to increase the accuracy of positioning system-based speed or pace detection and, therefore, the accuracy of the real-time coaching and/or feedback.

For example, the portable fitness processing device 102 software may continually add GPS waypoints to the memory 122, and the processor 120 may continually calculate speed points based on the elapsed time and measured distance between consecutive waypoints. The software may then save a predetermined number of speed points in a speed buffer, and may compare the values in the speed buffer to determine a weighted average speed.

Weighting factors may take into account how recently a value was added to the buffer, and may assign a greater weight to more recent values. Weighting factors may also consider how much a recent value deviates from the current average.

Data may be added to the buffer as it is recorded, and the buffer may build up until it reaches a predetermined size. When the buffer becomes full, it may begin discarding the oldest data point each time a new data point is added.

In an embodiment, these weighted average speeds may be the speeds that are displayed to the athlete 100 while the athlete 100 is using the portable fitness monitoring device 102, that are wirelessly transmitted to the server 112, and that are used for feedback and coaching.

A variety of methods may be employed to best determine accurate weighted average speeds. Those methods may include, for example, a standard average method, a cumulative sum method, a cluster average method, a time weighted average method, an inverse speed delta weighted average method, an acceleration adjusted instant speed method, or combinations of one or more of these methods.

Standard average methods may involve calculating mean speeds between two or more consecutive speed points. Cumulative sum methods may involve determining a cumulative sum of the deviation from a target value, such as the sum of all the differences in speed from a particular speed reference point. The reference point could be, for example, the running standard average of speed values. As ongoing cumulative sum values are determined, they may be analyzed by an algorithm to determine if a possible change in speed is valid or not. If the speed change is valid, it is factored in and used to provide feedback and coaching. If the speed change is not valid, it is ignored. Cluster average methods are similar to standard average methods, but instead of averaging only consecutive speed points within the moving buffer, speed points that occurred further apart in time are compared.

Time weighted average methods may take into account how recently a speed value was added to the buffer, and may assign a greater weight to more recent speed values. A weighting coefficient can be determined by various means. For example, in an inverse speed delta weighted average method, the weighting coefficient may have the effect of weighting particular speed points less the further they are away from a particular reference value.

Acceleration adjusted instant speed methods may involve adjusting speed point values based on known real-life human acceleration capabilities. In other words, the point to point difference in instantaneous speed may be limited by a maximum known acceleration. For example, the method may assume a maximum human runner's acceleration to be 1.0 miles per hour per second. Thus, the system would limit a recorded and/or output speed change of 10 miles per hour to a period of 10 seconds.

In one embodiment, the positioning system smoothing module 1800 may employ a combination of the inverse speed delta weighted average and acceleration adjusted instant speed methods. For example, instantaneous calculated speeds may first be adjusted using an acceleration adjustment formula, and then they resulting values may be feed into an inverse speed delta weighted average formula.

In another embodiment of the present invention, the GPS smoothing module 1800 may employ an additional method to increase the accuracy of GPS-based speed and pace detection and, therefore, the accuracy of the real-time coaching and/or feedback.

In the above described scenario, there may be significant lag time in reporting an updated speed of the athlete 100 in real time during the activity. For example, an athlete 100 may be running at a speed of eight miles per hour when the portable fitness monitoring device 102 informs the athlete 100 that their workout routine calls for them to enter a new performance zone interval that will bring their speed up to ten miles per hour. Assuming the athlete 100 quickly accelerates to ten miles per hour, a significant amount of time may pass before the weighted average speed settles in around ten miles per hour, because it may be weighted down with a plurality of eight mile per hour data points in the buffer.

As a result, if an incorrect speed is output to the athlete 100 and the athlete 100 recognizes this, the athlete 100 may lose confidence in the accuracy of the system. Alternatively, the athlete 100 may attempt to speed up even more in response to observing a speed that appears too low, even if the athlete 100 has in reality already achieved the proper speed. Similarly, the portable fitness monitoring software may provide an additional coach prompt for the athlete 100 to speed up when the athlete 100 has in reality already achieved the proper speed.

In one embodiment, in an attempt to remedy these issues, the buffer may periodically discard all of its data points in response to an anticipated change in speed by the athlete 100. For example, if the portable fitness monitoring device 102 informs the athlete 100 that their workout routine calls for them to enter a new performance zone interval, the GPS smoothing module 1800 may cause the buffer to discard all of its data points so that the new weighted average speed is not affected by values that are known to be outdated. In other words, the portable fitness monitoring device 102 may be capable of adjusting the buffer based on known or anticipated speed changes, based on the device's knowledge of the workout routine.

Figure 53:
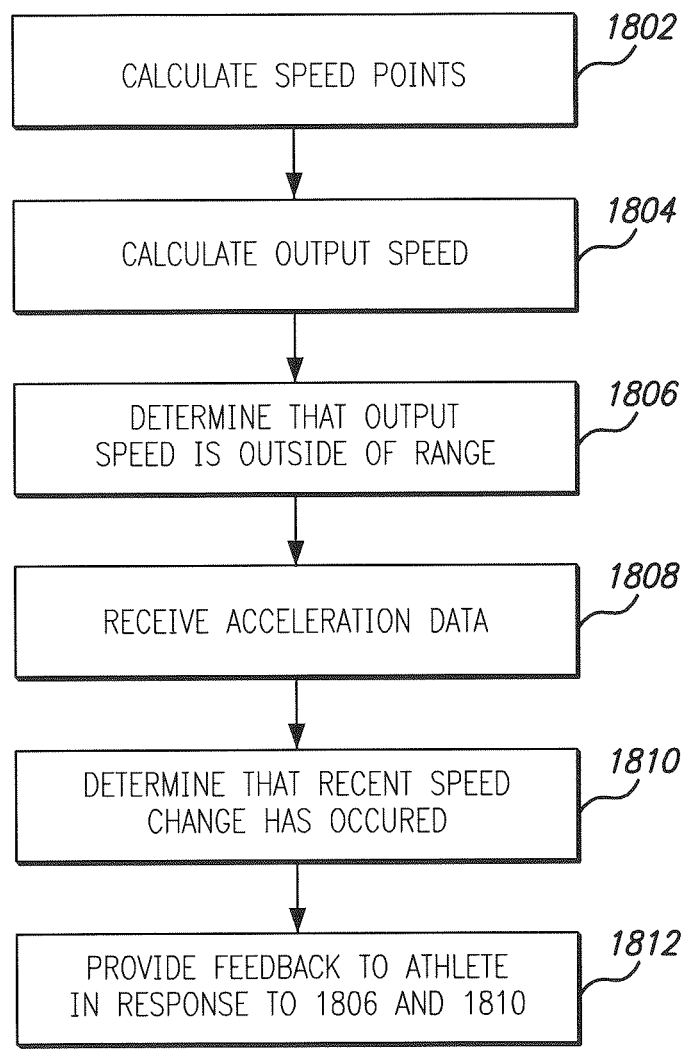
FIG. 53 is a flow chart outlining actions capable of being initiated by software according to an embodiment of the present invention.

In one embodiment of the present invention, the GPS smoothing module 1800 may employ an yet another additional method to increase the accuracy of GPS-based speed and pace detection and, therefore, the accuracy of the real-time coaching and/or feedback, as outlined in FIG. 53.

At step 1802, a plurality of speed points may be calculated from a plurality of time-stamped position points. At step 1804, an output speed may be calculated based on at least some of the plurality of speed points. At step 1806, a determination may be made that the output speed is outside of a predetermined speed range. At step 1808, acceleration data may be received from an accelerometer. At step 1810, a determination may be made that a recent speed change has occurred based on the acceleration data. Finally, at step 1812, feedback may be provided to the athlete 100 via the portable fitness monitoring device 102. In an embodiment, the feedback may be provided in response to the determination that the output speed is outside of the predetermined speed range, and in response to the determination that the recent speed change has occurred. In one embodiment, these steps need not be performed in the order listed.

The plurality of time-stamped position points may be, for example, GPS position points collected by the portable fitness monitoring device 102 at the athlete 100 engages in an activity and traverses a route, as described above. In an embodiment, the processor 120 of the portable fitness monitoring device 102 may receive the plurality of time-stamped position points for further processing.

A plurality of speed points may be calculated from the plurality of time-stamped position points. In some embodiments, as described above, speed point calculation may involve factoring in the distances between consecutive pairs of time-stamped position points and factoring in the time periods between consecutive pairs of time-stamped position points.

An output speed may be calculated based on at least some of the plurality of speed points. In one embodiment, the output speed may be calculated averaging two or more of the plurality of speed points. As described above, weighted or other averaging may be employed. In another embodiment, also as described above, the positioning system smoothing module 1800 may maintain at least some of the plurality of speed points in a speed buffer. In such an embodiment, the step of calculating the output speed include calculating an output speed based only on the plurality of speed points in the speed buffer. As explained above, the speed buffer may be useful for conducting averaging to determine an output speed.

In an embodiment, an accelerometer may be contained within a housing of the portable fitness monitoring device. For example, the portable fitness monitoring device 102 may be a mobile phone having both a GPS receiver and an accelerometer contained within the mobile phone housing. In another embodiment, the accelerometer may be physically separate from the portable fitness monitoring device 102 and may communicate wirelessly with it, as described above.

A determination that a recent speed change has occurred may be based on acceleration data provided by the accelerometer. The accelerometer data may provide acceleration data in response to movements of the portable fitness monitoring device 102 and/or the athlete's 100 body during an activity. In an embodiment, certain changes in the accelerometer signal may generally suggest that the athlete 100 has changed speeds.

In one embodiment, the acceleration data may take the form of a plurality of acceleration points having varying magnitudes. For example, the accelerometer may be periodically sampled and may provide consecutive data points registering 1 G, 1 G, and 2 Gs. In this case, the determination that a recent speed change has occurred may include analyzing the differences in the magnitudes of the acceleration points. For example, it may be determined that a speed change did not occur between the 1 G and 1 G data points, but that a speed change did occur between the 1 G and 2 Gs data points.

In another embodiment, the acceleration data may take the form of an acceleration signal having oscillations. For example, an accelerometer signal may have a generally sinusoidal output that corresponds to a repetitive motion, such as running. In this case, the determination that a recent speed change has occurred may include analyzing the changes in the oscillations of the acceleration signal. For example, changes in the amplitude or frequency of the sinusoidal output may suggest that a speed change has occurred.

In an embodiment of the present invention where a speed buffer is used, the positioning system smoothing module may initiate discarding the plurality of speed points in the speed buffer in response to the determination that a recent speed change has occurred, based on the accelerometer data. For example, if the portable fitness monitoring device 102 detects a recent speed change via the accelerometer, the positioning system smoothing module 1800 may cause the speed buffer to discard all of its speed points so that a new output speed calculation is not affected by values that are likely to correspond to a speed the athlete 100 is no longer maintaining. In other words, the portable fitness monitoring device 102 may be capable of adjusting the speed buffer based on the accelerometer data. This may increase the accuracy of positioning system-based speed detection and, therefore, the accuracy of the real-time coaching and/or feedback.

Feedback may be provided in response to the determination that the output speed is outside of the predetermined speed range, and in response to the determination that the recent speed change has occurred (via the accelerometer). As described in detail throughout the specification, feedback may include, for example, audio, visual, and/or tactile feedback. Feedback may be generated as part of a planned or custom workout routine that the portable fitness monitoring device 102 is executing. Feedback may inform the athlete 100 that they have fallen below or risen above a desired intensity level for a particular portion of a workout.

In an embodiment, the predetermined speed range may be associated with a color-coded intensity zone, as described above with respect to the color-coded zone system depicted in FIGS. 10 and 11. In such an embodiment, the feedback may audibly or visually convey a color to the athlete in accordance with the color-coded zone system.

For example, an athlete 100 may be engaged in an activity utilizing a portable fitness monitoring device 102 executing a workout routine. The workout routine may presently call for the athlete to maintain a speed corresponding to the green zone (i.e. the predetermined speed range corresponds to the green zone). If the portable fitness monitoring device 102 determines that the output speed is below the green zone speed range and further determines that a recent speed change has occurred based on the accelerometer data, the portable fitness monitoring device 102 may announce "your intensity is only at a blue zone level, increase your intensity to enter the green zone."

In certain situations, determining that a recent speed change has occurred based on accelerometer data may increase the accuracy of positioning system-based speed detection and, therefore, the accuracy of the real-time coaching and/or feedback, as compared to a situation where such information is not considered.

For example, in the situation described above where the workout routine presently calls for the athlete to maintain a speed corresponding to the green zone, the green zone may range from seven to eight miles per hour. As the athlete 100 is conducting the activity, the output speed derived from the positioning system data, which may suffer from some degree of inaccuracy, may indicate that the athlete's 100 speed has fallen to 6.5 miles per hour. In this case, the portable fitness monitoring device 102 would normally provide a feedback prompt to speed up, such as "your intensity is only at a blue zone level, increase your intensity to enter the green zone." However, in a situation where the feedback additionally depends on a determination that a recent speed change has occurred based on accelerometer data, unless such a determination is made, the feedback may be withheld. For example, the accelerometer data may indicate a relatively steady pattern of acceleration that indicates that the athlete 100 has not recently changed speeds. Of course, if the accelerometer data indicated that a recent speed change had occurred, the feedback would still be provided.

Thus, the various embodiments described above with respect to the positioning system smoothing module may increase the accuracy of positioning system-based speed detection and, therefore, the accuracy of the real-time coaching and/or feedback.

In another embodiment of the present invention, one or more of the various smoothing methods described may be used and may result in a series of speed and/or pace output values. Sometimes the output values may vary once every second or two, but only by small amounts. For example, pace output values of, for example, 8:57, 9:03, 9:01, 8:55, 9:02, 9:04, 9:06, and 8:59 may be calculated. If these individual values were displayed to the athlete 100 during an activity, the athlete may become distracted by having their attention drawn to constantly varying values that essentially reflect static performance.

In an embodiment, to minimize the potential for such distraction, a minimum deviation may be calculated and employed. If the difference between consecutive calculated output values is less than the minimum deviation value, the value actually displayed to the athlete 100 will not change. For example, with regard to the pace-based example provided above, if a minimum deviation of 8 seconds is used, after the first pace output value of 8:57 is displayed, the display would continue to output 8:57 even as values of 9:03, 9:01, 8:55, 9:02, and 9:04 are received, because each of these values is less that 8 seconds different from 8:57. However, when the value of 9:06 is received, 9:06 would be displayed because it is greater than 8 seconds different from 8:57. From this point on, 9:06 would be displayed until another value greater than 8 seconds different from 9:06 is received. This has the effect of removing micro variations from the pace output without changing the overall macro changes.

Using such a system, however, it would be possible for the display to remain constant for a long stretch of time if received values continually remain within the minimum deviation. An athlete 100 observing such a display may begin to assume that the display is frozen or that the device is otherwise not working. Accordingly, it may be desirable to limit the maximum duration of a content display. In an embodiment, a cap may be placed such that the display must be allowed to change after a given period of time, such as, for example, eight seconds. Thus regardless of the degree of deviation or lack thereof from the reference point, a new received value may be displayed after eight seconds.

In one embodiment of the present invention, acceleration data may be used to predict speed data in the event that a GPS signal is lost in the middle of an athlete's 100 activity. For example, as described above, prior to the point that a GPS signal is lost, the GPS data may have been used to determine the output speed. Rather than reporting the output speed as zero once the GPS signal is lost, the device may look to the accelerometer data.

For example, during the GPS outage, if the accelerometer data shows a relatively steady pattern that indicates that the athlete 100 has not recently changed speeds, the device may continue to report a consistent output speed until the GPS signal is restored again. On the other hand, during the GPS outage, if the accelerometer data shows a steadily increasing or decreasing pattern that indicates that the athlete 100 was in the course of speeding up or slowing down, the device may continue to report a steadily increasing or decreasing speed until the GPS signal is restored again.

In some embodiments of the present invention, the positioning system receiver 126 of the portable fitness monitoring device 102 may advantageously be used to trigger certain functionalities, as is described in further detail below.

Figure 54:
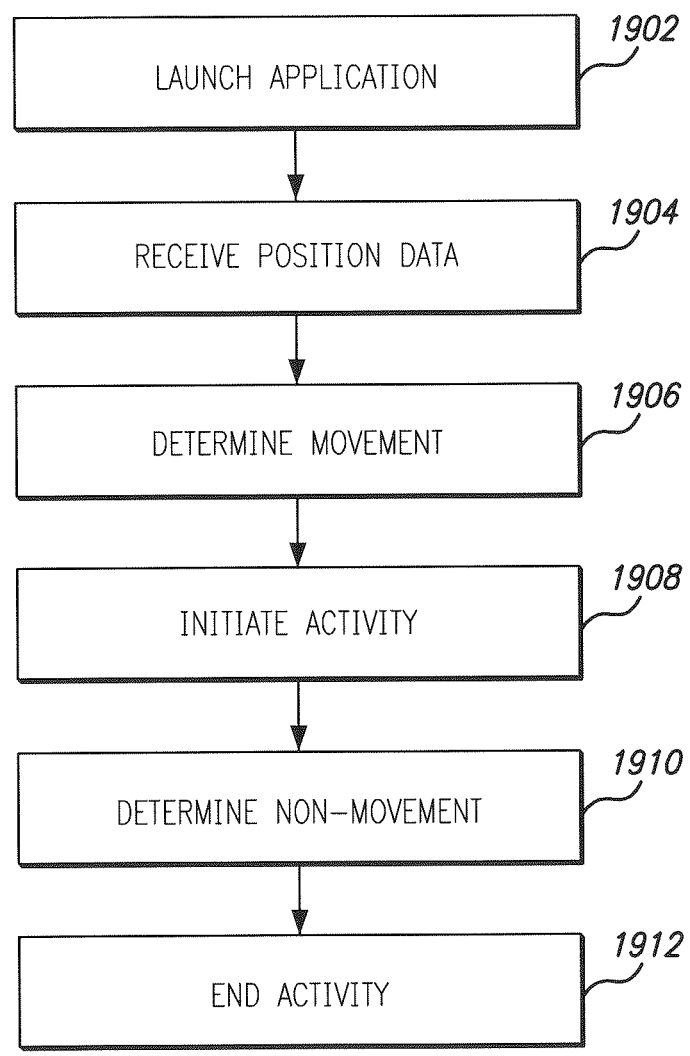
FIG. 54 is a flow chart outlining actions capable of being initiated by software according to an embodiment of the present invention.

With reference to FIG. 54, in one embodiment, at step 1902, a portable fitness monitoring application may be launched on the portable fitness monitoring device 102. Next, at step 1904, position data may be received from a satellite positioning system receiver 126 of the portable fitness monitoring device 102. Then, at step 1906, the application may determine that the position data indicates that the portable fitness monitoring device 102 is moving. At step 1908, an activity may be initiated in response to the determination that the portable fitness monitoring device 102 is moving. Next, at step 1910, the application may determine that the position data indicates that the portable fitness monitoring device 102 is not moving. Finally, at step 1912, the activity may end in response to the determination that the portable fitness monitoring device 102 is not moving.

Such features may be employed by a portable fitness monitoring device 102, for example, in the form of a mobile phone. The portable fitness monitoring application may be an application having features such as those described above with reference to FIG. 21. For example, the application may execute workout routines a portable fitness monitoring device 102 supported by an athlete 100 while an athlete 100 engages in an activity.

Position data, such as a plurality of position points, may be received from a satellite positioning system receiver 126 of the portable fitness monitoring device 102, as described above. For example, a GPS receiver of the portable fitness monitoring device 102 may provide a plurality of time-stamped GPS position points to the processor 120 of the portable fitness monitoring device 102.

Eventually, after the athlete 100 decides to begin their activity (e.g. running, biking, inline skating, skiing, golfing, etc.) and begins moving, the application may determine that the position points indicate that the portable fitness monitoring device 102 is moving. Such a determination may not always be straightforward due to inherent GPS errors and uncertainties, such as those described above.

In one embodiment, this determination may be based on a determination that the distance between two consecutive position points exceeds a predetermined threshold. For example, the application may determine that two consecutive GPS position points indicate that the portable fitness monitoring device 102 (and thus the athlete 100) is moving because the locations associated with the position points are more than five meters apart.

In another embodiment, the determination that the position points indicate that the portable fitness monitoring device 102 is moving may be based on a determination that the distance between two consecutive position points exceeds a predetermined threshold for at least a predetermined period of time. For example, the application may determine that two consecutive GPS position points indicate that the portable fitness monitoring device 102 (and thus the athlete 100) is moving because the locations associated with the position points are more than five meters apart for several consecutive sets of position points for five seconds.

In a further embodiment, the determination that the position points indicate that the portable fitness monitoring device 102 is moving may be based on a determination that a series of a minimum number of position points are each at least a minimum distance from a starting point. If the minimum number of position points and the minimum distance are large enough, it would be highly likely that the athlete 100 is moving if this test is met. However, making these values too large increases the lag time in making the movement determination.

In one embodiment, the determination that the position points indicate that the portable fitness monitoring device 102 is moving may be based on a determination that similar to that just described, but modified to reflect a known position point uncertainty. Specifically, if the uncertainty of a particular position point is known or can be calculated and expressed as a function of distance, the minimum distance described above can be modified as a function of the uncertainty. In other words, position points associated with high uncertainties will be less likely to be relied upon.

In another embodiment, the determination that the position points indicate that the portable fitness monitoring device 102 is moving may be based on a determination that a minimum number of position points are ever increasing in distance from the starting point (i.e. a concentric circle method). This method advantageously does not require the athlete 100 to have covered a minimum distance, but alone in a noisy signal environment the test may be difficult to satisfy. In an embodiment, an accelerometer signal may be used to reduce the minimum number of position point required. Specifically, if the accelerometer signal indicates a change in speed, as described above, the concentric circle test may only need to employ a reduce number of position points to make a determination.

In a further embodiment, the determination that the position points indicate that the portable fitness monitoring device 102 is moving may be based on a combination of the concentric circle method and one of the minimum distance methods described above. Specifically, the portable fitness monitoring device 102 may first employ the concentric circle method, while still collecting and analyzing data according to the minimum distance method in parallel. If the concentric circle method is satisfied, the athlete 100 is considered to be moving. If the concentric circle test fails, the device falls back on the minimum distance method to determine whether the athlete 100 is moving.

In one embodiment, the concentric circle test may be modified by analyzing bearings (i.e. directional headings). Specifically, as each new position point is received, a bearing from the starting point to the new point may be calculated. The test is not satisfied if the bearing for a new point differs from any previous bearing by a set number of degrees, such as, for example, 90 degrees.

In another embodiment, position points may be collected in a set and analyzed by known statistical methods to determine the randomness of the position points. For example, the randomness of the latitudes of the points, the longitudes of the points, or both may be analyzed.

An activity may be initiated by the application in response to the determination that the portable fitness monitoring device 102 is moving.

In one embodiment the activity may be the execution of a workout routine, such that the portable fitness monitoring device 102 may begin to execute a workout routine in response to the determination that the portable fitness monitoring device 102 is moving. Workout routines are described in detail throughout the specification. For example, in one embodiment, the workout routine may include a plurality of intervals, where each interval has an intensity goal. The intensity goal may be, for example, a target heart rate range, a target speed range, or a target pace range. As described above, the target performance parameter intensity goal ranges may be associated with a color-coded zone system. Thus, embodiments of the present invention may advantageously be used to trigger the initiation of workouts without requiring the athlete 100 to take an affirmative action beyond initiating motion, such as, for example, actuating a button on the portable fitness monitoring device 102.

In another embodiment the activity may be the playback of music, such that the portable fitness monitoring device 102 may begin to playback music in response to the determination that the portable fitness monitoring device 102 is moving. In one embodiment, the playback of music may not begin until an additional determination is made that workout routine execution has begun. Music playback is described in detail above.

For example, in one embodiment, the music played back to the athlete 100 during the activity may be associated with a playlist. Once music playback is initiated, the application may consult a playlist, which may indicate a group of music tracks to be played and the order they should be played in. The music tracks and/or a playlist file corresponding to the playlist may be save in the memory 122 of the portable fitness monitoring device. Alternatively, the music tracks and/or a playlist file corresponding to the playlist may be remotely accessible, for example, via a wireless network. In an embodiment, the music tracks and/or a playlist file may be downloaded to the portable fitness monitoring device 102 along with a workout routine. Thus, embodiments of the present invention may advantageously be used to trigger the playing of a playlist without requiring the athlete 100 to take an affirmative action beyond initiating motion, such as, for example, actuating a button on the portable fitness monitoring device 102.

Eventually, after the athlete 100 decides to end their activity (e.g. running, biking, inline skating, golfing, etc.) and ceases moving, the application may determine that the position points indicate that the portable fitness monitoring device 102 is not moving. The determination that the portable fitness monitoring device 102 is not moving may be made in a variety of ways similar to those described above with respect to determining that the portable fitness monitoring device 102 is moving.

In one embodiment, this determination may be based on a determination that the distance between two consecutive position points is less than a predetermined threshold. For example, the application may determine that two consecutive GPS position points indicate that the portable fitness monitoring device 102 (and thus the athlete 100) is not moving because the locations associated with the position points are less than five meters apart.

In another embodiment, the determination that the position points indicate that the portable fitness monitoring device 102 is not moving may be based on a determination that the distance between two consecutive position points is less than a predetermined threshold for at least a predetermined period of time. For example, the application may determine that two consecutive GPS position points indicate that the portable fitness monitoring device 102 (and thus the athlete 100) is not moving because the locations associated with the position points are less than five meters apart for several consecutive sets of position points for five seconds.

In a further embodiment, the determination that the position points indicate that the portable fitness monitoring device 102 is not moving may be based on first determining speed points. If the speed points suggest that the speed has dropped below a predetermined level, for example one mile per hour, the athlete 100 may be considered to be stopped.

In an embodiment, an accelerometer signal may be used to that the portable fitness monitoring device 102 is not moving. Specifically, if the accelerometer signal indicates a change in speed, as described above (i.e. that the speed has dropped to zero), it may be assumed that the athlete 100 is no longer moving.

Regardless of whether the activity is the execution of a workout routine or the playback of music, the activity may be ended by the application in response to the determination that the portable fitness monitoring device 102 is not moving. Thus, embodiments of the present invention may advantageously be used to end the execution of a workout routine and/or end the playback of music without requiring the athlete 100 to take an affirmative action beyond ceasing motion, such as actuating a button on the portable fitness monitoring device 102. In an embodiment, the system may pause music in response to a stop in motion and then restart it when the user is moving again. When the user us finally stopped, the system may stop the music and the workout routine.

As described above with respect to the GUIs provided to a user at a personal computer 114 via the server 112, in an embodiment of the present invention, the history sub-module of the track module 500 may provide a playlist section in a sidebar 514. If the athlete 100 conducted a workout while listening to music on a music-enabled portable fitness monitoring device 102, the playlist section may provide a listing of the musical audio tracks that the athlete 100 listened to during their workout. In an embodiment, the musical audio tracks that the athlete 100 listened to during their workout may be correlated to performance information collected during the workout.

As described above, a portable fitness monitoring device 102 may be supported by an athlete 100 during a workout. The portable fitness monitoring device 102 may be associated with one or more sensors 104 that are capable of detecting information used to measure and/or calculate performance parameters, such as location, distance covered, speed, pace, and/or heart rate. The portable fitness monitoring device 102 may include an audio unit 134. In one embodiment, the audio unit 134 may be responsible for managing the storage and playback of music tracks, which may involve the use of a playlist. Other music track and/or playlist features may also be included, such as those disclosed in commonly owned U.S. patent application Ser. No. 11/857,862, titled "Location-aware fitness training device, methods, and program products that support real-time interactive communication and automated route generation," which is incorporated herein by reference in its entirety.

When the portable fitness monitoring device 102 detects, measures, and/or calculates parameter information, including the locations of time-stamped position points encountered by the athlete 100 while traversing a route (e.g. via a positioning system receiver 126), instantaneous performance parameters may be correlated with the position points encountered at roughly the same time the performance parameters were collected. This correlated performance parameter information may be transmitted to the server 112, for example, via the WWAN 128 or WPAN 130 transceiver in substantially real-time during the workout or after the workout has been completed, as described in detail above.

In another embodiment, a music track that was played for the athlete 100 may be correlated with the position points encountered and/or performance parameter information collected at roughly the same time that the music track was played for the athlete 100 by the portable fitness monitoring device 102. In this way, the system of the present invention may advantageously be able to provide the athlete 100 with information regarding the relationship between the music they listened to and their performance during the workout.

In one embodiment of the present invention, the history sub-module of the track module 500 may initiate the display of a GUI window that includes performance parameter information regarding an athlete's 100 performance during a workout as a function of time. The GUI window may also include the title of a music track that was played for the athlete 100 by a portable fitness monitoring device 102 during the workout. In an embodiment, the display of the title of a music track may occur in response to a user specifying a particular point in time during the workout.

For example, as described above and as illustrated in FIGS. 38 and 39, performance information for one or more performance parameters may be displayed in the primary display 512 of a GUI window on a line graph whose x-axis is either time or distance based, and whose y-axis is correlated to the value of the measured performance parameter. For example, in FIGS. 38 and 39, a line graph charts heart rate and pace information, respectively, as a function of time during the workout.

As illustrated in FIG. 40, a user interested in viewing instantaneous performance statistics throughout the athlete's 100 workout may be able to select and drag a scrollbar 516 with their cursor along the x-axis. As the user drags the scrollbar 516 across the x-axis, an icon may travel along the line graph plotted for the performance parameter of interest. In addition, a pop-up window displaying additional instantaneous performance data may appear and move across the screen along with the moving icon. In addition to the information displayed in FIG. 40, in an embodiment, as the user drags the scrollbar 516 across the x-axis, the title of a music track that was played for the athlete 100 by the portable fitness monitoring device 102 at a particular point in time may be displayed. This may be possible because, as described above, a music track that was played for the athlete 100 may be correlated with the position points encountered and/or performance parameter information collected at roughly the same time that the music track was played for the athlete 100 by the portable fitness monitoring device 102.

In another embodiment, the user may be able to specify the particular point in time during the workout for which they would like the corresponding music track title to be displayed by other mechanisms besides the scrollbar. For example, in an embodiment, the user may be able to specify the particular point in time during the workout for which they would like the corresponding music track title to be displayed by hovering their cursor directly over a portion of the line graph that corresponds to the particular point in time.

In one embodiment, the athlete 100 could conduct their workout using a GPS-enabled portable fitness monitoring device 102 capable of recording their geographic position points along the geographical route traversed. Either during traversal of the route or after the route has been completed, the GPS data could then be uploaded to the server 112 and associated with other performance monitoring information collected and/or music played during traversal of the route. Then, as illustrated in FIG. 44 and described above, an illustration of the athlete's 100 geographical route may be displayed to a user at a computer 114.

As illustrated in FIG. 45, a user interested in viewing instantaneous performance statistics throughout the workout may be able to select and drag a scrollbar 542 with their cursor along the bottom of the screen. As the user drags the scrollbar 542 across the bottom of the screen, an icon may travel along the geographical route path plotted. In addition, a pop-up window displaying additional instantaneous performance data may appear and move across the screen along with the moving icon. In addition to the information displayed in FIG. 45, in an embodiment, as the user drags the scrollbar 542 across the bottom of the screen, the title of a music track that was played for the athlete 100 by the portable fitness monitoring device 102 at a particular point along the route may be displayed. This may be possible because, as described above, a music track that was played for the athlete 100 may be correlated with the position points encountered and/or performance parameter information collected at roughly the same time that the music track was played for the athlete 100 by the portable fitness monitoring device 102.

In another embodiment, the user may be able to specify the particular point along the route during the workout for which they would like the corresponding music track title to be displayed with respect to the geographical route path by other mechanisms besides the scrollbar. For example, in an embodiment, the user may be able to specify the particular point along the route during the workout for which they would like the corresponding music track title to be displayed by hovering their cursor directly over a portion of the illustration of the geographical route path that corresponds to the particular point along the route. In another embodiment, the system may play a designated highly motivational song based on track characteristics (e.g. when the user encounters an uphill section).

In an embodiment, the illustration of the geographical route may also be overlaid on a map, as described above with respect to FIG. 44. In other embodiments, in response to the user specifying a particular point in time during the workout, the name of a band or artist associated with the music track may also be displayed along with the title of the music track.

Figure 55:
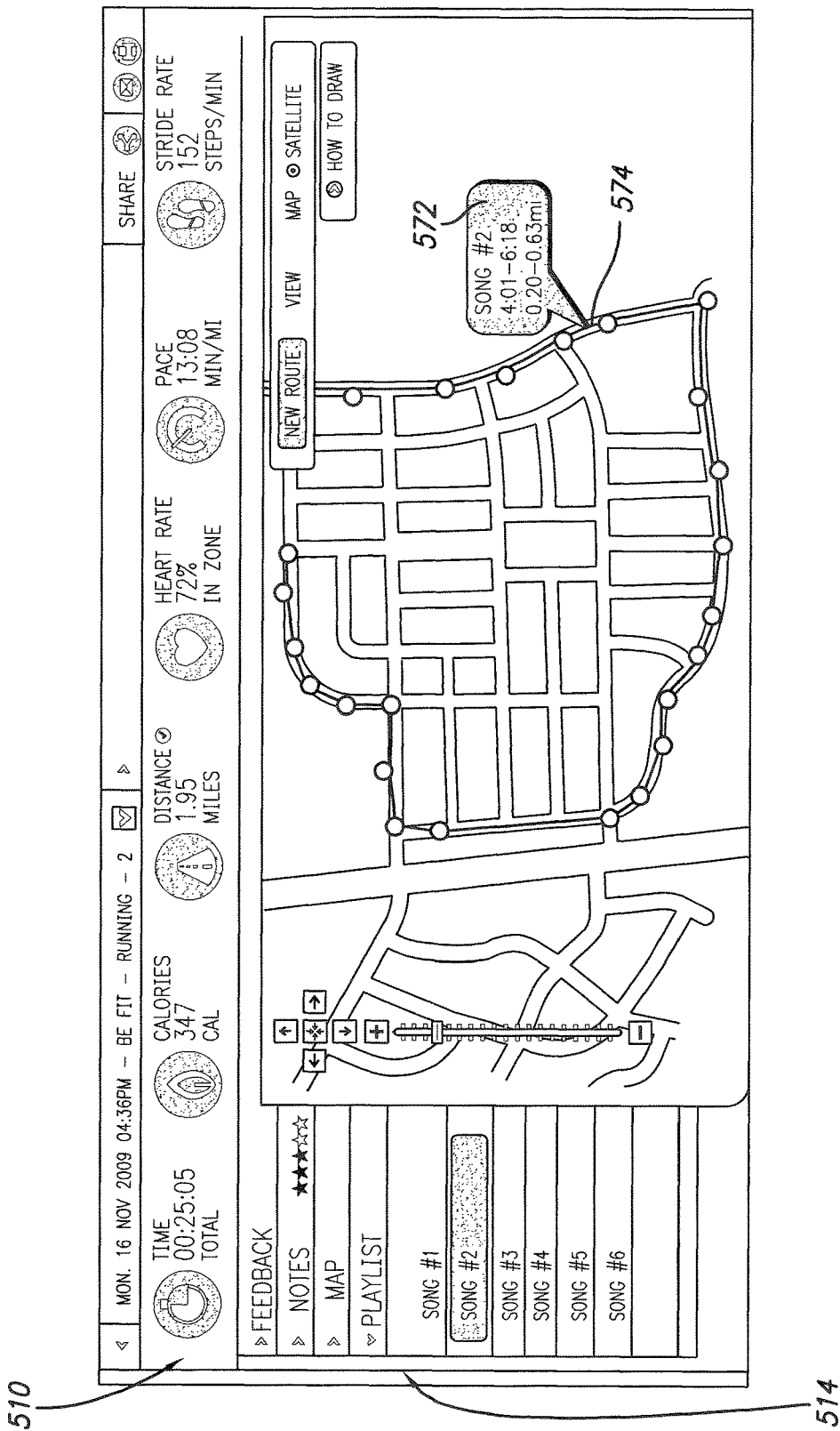
FIG. 55 is an exemplary GUI window according to an embodiment of the present invention.

In one embodiment, as illustrated in FIG. 55, when a user hovers their cursor over a particular song on a playlist, a pop-up balloon 572 may appear near a highlighted portion of the route 574 that corresponds to the segment of the route that the athlete 100 was traversing while listening to the particular song (in the illustrated case, Song #2). As further illustrated, the pop-up balloon 572 indicates that Song #2 was played from the 4:01 to 6:18 time periods of the activity, which correspond to the 0.20-0.63 mile segments of the activity (i.e. route portion 574).

While the above described embodiments relating to the display of music track title information relied on display correlated to heart rate or position information, the displays may alternatively be correlated to any other performance parameter such as, for example, speed or pace. Furthermore, while the display was discussed as being with respect to time, the display may also be with respect to distance.

In addition to providing feedback regarding a particular music track that was played at a particular time and/or location during a workout, the playlist section may provide a listing of the musical audio tracks that the athlete 100 listened to during their workout.

In one embodiment, based on the correlation between music tracks played and performance information collected during a workout, the server 112 software may be able to analyze the music tracks played to determine how the athlete's 100 performance related to particular songs. For example, the software could determine which songs corresponded to the athlete's 100 highest heart rate, pace, and/or speed. In an embodiment, a listing of music tracks available to the athlete 100 could be provided in order based on which tracks were associated with the highest heart rates, paces, or speeds, and/or the music tracks could be grouped into various categories.

In another embodiment, based on this information, the server 112 software may be able to assist in the creation of suitable playlists for particular workouts. For example, as described above, in some embodiments, a playlist and/or the music tracks listed by the playlist may be transmitted to the portable fitness monitoring device 102 along with a workout routine. If a workout routine includes a series of heart rate, speed, or pace-based intervals with varying intensities, it may be advantageous to provide the athlete 100 with an accompanying playlist that provides music tracks that have, in the past, been shown to correlate well with given intensities for the athlete 100. For example, if the software has previously determined that three particular music tracks are associated with paces of around seven minutes per mile for a particular athlete 100 and that athlete is scheduled to engage in a workout that calls for a yellow zone interval where the yellow zone corresponds to paces of six to eight minutes per mile, then it may be advantageous to provide the athlete 100 with a playlist that indicates that these three music tracks should be played during the athlete's 100 yellow zone interval.

G. CONCLUSION

Various aspects of the present invention, or any parts or functions thereof, may be implemented using hardware, software, firmware, tangible computer readable or computer usable storage media having instructions stored thereon, or a combination thereof and may be implemented in one or more computer systems or other processing systems.

Program products, methods, and systems for providing fitness monitoring services of the present invention can include any software application executed by one or more computing devices. A computing device can be any type of computing device having one or more processors. For example, a computing device can be a workstation, mobile device (e.g., a mobile phone, personal digital assistant, tablet computer, or laptop), computer, server, compute cluster, server farm, game console, set-top box, kiosk, embedded system, a gym machine, a retail system or other device having at least one processor and memory. Embodiments of the present invention may be software executed by a processor, firmware, hardware or any combination thereof in a computing device.

In this document, terms such as "computer program medium" and "computer-usable medium" may be used to generally refer to media such as a removable storage unit or a hard disk installed in hard disk drive. Computer program medium and computer-usable medium may also refer to memories, such as a main memory or a secondary memory, which can be memory semiconductors (e.g., DRAMs, etc.). These computer program products provide software to computer systems of the present invention.

Computer programs (also called computer control logic) may be stored on main memory and/or secondary memory. Computer programs may also be received via a communications interface. Such computer programs, when executed, may enable computer systems of the present invention to implement embodiments described herein. Where embodiments are implemented using software, the software can be stored on a computer program product and loaded into a computer system using, for example, a removable storage drive, an interface, a hard drive, and/or communications interface.

Based on the description herein, a person skilled in the relevant art will recognize that the computer programs, when executed, can enable one or more processors to implement processes described above, such as the steps in the methods illustrated by the figures. In an embodiment, the one or more processors can be part of a computing device incorporated in a clustered computing environment or server farm. Further, in an embodiment, the computing process performed by the clustered computing environment may be carried out across multiple processors located at the same or different locations.

Software of the present invention may be stored on any computer-usable medium. Such software, when executed in one or more data processing device, causes the data processing device to operate as described herein. Embodiments of the invention employ any computer-usable or -readable medium, known now or in the future. Examples of computer-usable mediums include, but are not limited to, primary storage devices (e.g., any type of random access or read only memory), secondary storage devices (e.g., hard drives, floppy disks, CD ROMS, ZIP disks, tapes, magnetic storage devices, optical storage devices, MEMS, nanotechnological storage devices, memory cards or other removable storage devices, etc.), and communication mediums (e.g., wired and wireless communications networks, local area networks, wide area networks, intranets, etc.).

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

While many of the exemplary embodiments discussed above make reference to a color-coded heart rate zone-based system, color-coded zone systems based on zones of other parameters including, but not limited to, speed, pace, stride rate, calories, respiration rate, blood oxygen level, blood flow, hydration status, or body temperature may also be employed. The present invention is therefore not to be limited to only heart rate based zone systems.

Furthermore, while many of the exemplary embodiments discussed above make reference to a color-coded heart rate zone-based system where the zones may be defined as ranges of percentages of an athlete's maximum heart rate, heart rate zones may be defined based on other parameters as well.

The present invention has been described above by way of exemplary embodiments. Accordingly, the present invention should not be limited by any of the above-described exemplary embodiments, but should be defined only in accordance with the following claims and their equivalences.

What is claimed is:

1. A method for execution by a portable fitness monitoring device comprising:
   launching a portable fitness monitoring application on the portable fitness monitoring device;
   receiving a first set of position points from a satellite positioning system receiver of the portable fitness monitoring device;
   determining that the first set of position points indicates that the portable fitness monitoring device is moving;
   beginning execution of a workout routine in response to the determination that the portable fitness monitoring device is moving;
   receiving a second set of position points from the satellite positioning system receiver of the portable fitness monitoring device;
   determining that the second set of position points indicates that the portable fitness monitoring device is not moving, wherein the determination that the portable fitness monitoring device is not moving is based on a determination that a distance between two consecutive position points of the second set of position points is less than a predetermined threshold;
   ending execution of the workout routine in response to the determination that the portable fitness monitoring device is not moving;
   receiving a third set of position points from the satellite positioning system receiver of the portable fitness monitoring device;
   determining that the third set of position points indicates that the portable fitness monitoring device has resumed moving; and
   starting execution of the workout routine in response to the determination that the portable fitness monitoring device has resumed moving,
   wherein execution of the workout routine comprises providing feedback to a user of the portable fitness monitoring device during a physical activity,
   wherein ending execution of the workout routine comprises temporarily ceasing providing the feedback,
   wherein the workout routine includes a plurality of intervals, each interval having an intensity goal, and
   wherein each intensity goal is associated with a color-coded zone system.

2. The method of claim 1, wherein the portable fitness monitoring device is a mobile phone.

3. The method of claim 1, wherein the determination that the portable fitness monitoring device is moving is based on a determination that the distance between two consecutive position points of the first set of position points exceeds a predetermined threshold for at least a predetermined period of time.

4. The method of claim 1, wherein the determination that the portable fitness monitoring device is not moving is based on a determination that the distance between two consecutive position points of the second set of position points is less than a predetermined threshold for at least a predetermined period of time.

5. The method of claim 1, wherein the determination that the portable fitness monitoring device is moving is based on a determination that the distance between two consecutive position points of the first set of position points exceeds a predetermined threshold.

6. The method of claim 1, wherein execution of the workout routine comprises the recording of performance parameter information, and wherein ending execution of the workout routine comprises temporarily ceasing recording.

7. The method of claim 6, wherein starting-execution of the workout routine comprises resuming recording.

8. The method of claim 1, wherein starting execution of the workout routine comprises resuming providing feedback.

9. The method of claim 1, wherein determining that the first set of position points indicates that the portable fitness monitoring device is moving is based on a determination that distances between a reference position point and a plurality of position points are increasing.

10. The method of claim 9, wherein the determination that the distance between the reference position point and the plurality of position points is increasing is further based on at least one directional heading relative to the reference position point.

11. A method for execution by a portable fitness monitoring device comprising:
    launching a portable fitness monitoring application on the portable fitness monitoring device;
    receiving a first set of position data from a satellite positioning system receiver of the portable fitness monitoring device;
    determining that the first set of the position data indicates that the portable fitness monitoring device has moved from a first geographical location to a second geographical location that is different than the first geographical location;
    beginning music playback in response to the determination that the portable fitness monitoring device has moved from the first geographical location to the second geographical location;
    receiving a second set of position data from a satellite positioning system receiver of the portable fitness monitoring device;
    determining that the second set of position data indicates that the portable fitness monitoring device has remained at a third geographical location; and
    ending music playback in response to the determination that the portable fitness monitoring device has remained at a third geographical location,
    wherein the first set of position data comprises a plurality of position points, and
    wherein the determination that the portable fitness monitoring device has moved from the first geographical location to the second geographical location is based on a determination that a distance between two consecutive position points of the first set of position data exceeds a predetermined threshold for at least a predetermined period of time.

12. The method of claim 11, wherein the portable fitness monitoring device is a mobile phone.

13. The method of claim 11, wherein the determination that the portable fitness monitoring device has remained at the third geographical location is based on a determination that the distance between two consecutive position points of the second set of position data is less than a predetermined threshold.

14. The method of claim 13, wherein the determination that the portable fitness monitoring device has remained at the third geographical location is based on a determination that the distance between two consecutive position points of the second set of position data is less than a predetermined threshold for at least a predetermined period of time.

15. The method of claim 11, wherein the music played back is associated with a playlist.

16. The method of claim 11, wherein the determination that the portable fitness monitoring device has moved from the first geographical location to the second geographical location is further based on a known position point uncertainty of at least one of the plurality of position points.

17. A method for execution by a portable fitness monitoring device comprising:
    launching a portable fitness monitoring application on the portable fitness monitoring device;
    receiving a first set of position data comprising a plurality of position points from a satellite positioning system receiver of the portable fitness monitoring device;
    determining that the first set of position data indicates that the portable fitness monitoring device has moved from a first geographical location to a second geographical location that is different than the first geographical location;
    wherein the determination that the portable fitness monitoring device has moved from the first geographical location to the second geographical location is based on a determination that the distance between two consecutive position points of the first set of position data exceeds a predetermined threshold for at least a predetermined period of time;
    beginning music playback in response to the determination that the portable fitness monitoring device has moved from the first geographical location to the second geographical location;
    receiving a second set of position data from a satellite positioning system receiver of the portable fitness monitoring device;
    determining that the second set of position data indicates that the portable fitness monitoring device has remained at a third geographical location;
    pausing music playback in response to the determination that the portable fitness monitoring device has remained at a third geographical location; and
    restarting music playback in response to a determination that the portable fitness monitoring device has resumed moving,
    wherein the music played back is associated with an ordered playlist.

18. The method of claim 17, further comprising:
    receiving a third set of position data from the satellite positioning system receiver of the portable fitness monitoring device; and
    wherein the determination that the portable fitness monitoring device has resumed moving is based on the third set of position data.

19. The method of claim 17, wherein the portable fitness monitoring device is a mobile phone.

20. The method of claim 17, wherein the determination that the portable fitness monitoring device has remained at the third geographical location is based on a determination that the distance between two consecutive position points of the second set of position data is less than a predetermined threshold.

21. The method of claim 20, wherein the determination that the portable fitness monitoring device has remained at the third geographical location is based on a determination that the distance between two consecutive position points of the second set of position data is less than a predetermined threshold for at least a predetermined period of time.

22. The method of claim 17, wherein the ordered playlist comprises a plurality of music tracks.

23. The method of claim 22, wherein the music tracks are grouped based on previously received athletic performance information of the user.

24. The method of claim 17, wherein the ordered playlist comprises a plurality of music tracks saved in a memory of the portable fitness monitoring device.

25. The method of claim 17, wherein the ordered playlist comprises a plurality of music tracks remotely accessible via a wireless network.

26. The method of claim 17, wherein the ordered playlist comprises a plurality of music tracks downloaded to the portable fitness monitoring device.

\* \* \* \* \*